US008524899B2

(12) United States Patent
Dervan et al.

(10) Patent No.: US 8,524,899 B2
(45) Date of Patent: Sep. 3, 2013

(54) ALTERNATIVE HETEROCYCLES FOR DNA RECOGNITION

(75) Inventors: Peter B. Dervan, San Marino, CA (US); Christoph A. Briehn, Obertshausen (DE); Dorte Renneberg, Bern (CH); Philipp Weyermann, Siassach (CH); Raymond Doss, Pasadena, CA (US); Michael Marques, San Mateo, CA (US)

(73) Assignee: California Institute of Technology, Pasadena, CA (US)

( * ) Notice: Subject to any disclaimer, the term of this patent is extended or adjusted under 35 U.S.C. 154(b) by 1119 days.

(21) Appl. No.: 10/794,584

(22) Filed: Mar. 4, 2004

(65) Prior Publication Data

US 2005/0026174 A1    Feb. 3, 2005

Related U.S. Application Data

(60) Provisional application No. 60/452,180, filed on Mar. 4, 2003, provisional application No. 60/452,039, filed on Mar. 4, 2003.

(51) Int. Cl.
*C07D 235/18* (2006.01)
*C07D 471/14* (2006.01)
*C07D 471/04* (2006.01)

(52) U.S. Cl.
USPC ...... 544/184; 546/118; 548/303.1; 548/306.1

(58) Field of Classification Search
USPC .............. 548/306.1; 435/6.1, 6.12; 544/183, 544/269
See application file for complete search history.

(56) References Cited

U.S. PATENT DOCUMENTS

| | | | |
|---|---|---|---|
| 3,854,480 | A | 12/1974 | Zaffaroni |
| 4,452,775 | A | 6/1984 | Kent |
| 4,675,189 | A | 6/1987 | Kent et al. |
| 5,075,109 | A | 12/1991 | Tice et al. |
| 5,133,974 | A | 7/1992 | Paradissis et al. |
| 5,407,686 | A | 4/1995 | Patel et al. |
| 5,624,898 | A | 4/1997 | Frey, II |
| 5,736,152 | A | 4/1998 | Dunn |
| 6,180,603 | B1 | 1/2001 | Frey, II |

FOREIGN PATENT DOCUMENTS

| | | |
|---|---|---|
| EP | 1 491 534 | 12/2004 |
| GB | 1088096 | * 11/1967 |
| JP | 09-323996 | * 12/1997 |
| WO | WO 91/97947 | 6/1991 |
| WO | WO 98/37066 | 8/1998 |
| WO | WO 98/45284 | 10/1998 |
| WO | WO 00/33813 | 6/2000 |
| WO | WO 00/40605 | 7/2000 |
| WO | WO 01/41782 | 6/2001 |
| WO | WO 02/101073 A2 | * 12/2002 |
| WO | WO 03/076412 | 9/2003 |

OTHER PUBLICATIONS

Fabian et al., Journal of Luminescence (1999), 85 (1-3), 137-148.*
Arcamone, et al., "Structure and Synthesis of Distamycin A" *Nature* 203:1064-1065 (1964).
Baird and Dervan, "Solid Phase Synthesis of Polyamides Containing Imidazole and Pyrrole Amino Acids" *J. Am. Chem. Soc.* 118:6141-6146 (1996).
Behrens, et al., "Synthesis of a Hoechst 32258 Analogue Amino Acid Building Block for Direct Incorporation of a Fluorescent, High-Affinity DNA Binding Motif into Peptides" *Bioconjugate Chem.* 12:1021-1027 (2001).
Belitsky, et al., "Solid-Phase Synthesis of DNA Binding Polyamides on Oxime Resin" *Bioorg. Med. Chem.*10:27677-2774 (2002).
Briehn, et al., "Alternative Heterocycles for DNA Recognition: The Benzimidazole/Imidazole Pair" *Chem. Eur. J.* 9:2110-2112 (2003).
Church, et al., "N-(2-Chloroethyl)-N-Nitrosoureas Covalently Bound to Nonionic and Monocationic Lexitropsin Dipeptides, Synthesis, DNA Affinity Binding Characteristics, and Reactions with $^{32}$P-End-Labeled DNA" *Biochemistry* 29:6827-6838 (1990).
Clanton, et al., "Novel Sulfonated and Phosphonated Analogs of Distamycin Which Inhibit the Replication of HIV" *Antiviral Res.* 27:335-354 (1995).
Dervan, et al., "Sequence-Specific DNA Recognition by Polyamides" *Current Opinion in Chemical Biology*, 3:688-693 (1999).
Gottesfeld, et al., "Regulation of Gene Expression by Small Molecules" *Nature* 387:202-205 (1997).
Graham and Prevec, "Manipulation of Adenovirus Vectors" Methods in Mol. Biol.: *Gene Transfer and Expression Protocols* 7:109-128 (1991).
He, et al., "Microgonotropens and Their Interactions with DNA. 1. Synthesis of the Tripyrrole Peptides Dien-Microgonotropen-a, -b, and -c and Characterization of Their Interactions with dsDNA" *J. Am. Chem. Soc.* 115:7061-7071 (1993).
Ji, et al., "Tris-Benzimidazole Derivatives: Design, Synthesis and DNA Sequence Recognition" *Bioorg. Med. Chem.* 9:2905-2919 (2001).
Kielkopf, etal., "Structural Basis for G-C Recognition in the DNA Minor Groove" *Nature Struct. Biol.* 5:104-109 (1998).
Kumar, et al., "Sequence Specific Molecular Recognition and Binding by a GC Recognizing Hoechst 33258 Analogue to the Decadeoxyribonucleotide d-[CATGGCCATG]: Structural and Dynimic Aspects Deduced from High Field $^1$H-NMR Studies" *J. Biomot Struct. Dyn.* 8:331-357 (1990).

(Continued)

*Primary Examiner* — Joseph K. McKane
*Assistant Examiner* — Amanda L. Aguirre
(74) *Attorney, Agent, or Firm* — Foley & Lardner LLP

(57) ABSTRACT

Methods and compositions are provided for forming complexes between dsDNA and novel oligomers comprising fused six-membered rings. By appropriate choice of target sequences and oligomers, complexes comprising oligomer-DNA are obtained with high association constants. The formation of complexes can be used for identification of specific dsDNA sequences, for inhibiting gene transcription, and as a therapeutic for inhibiting proliferation of undesired cells or modulation of expression of specific genes.

13 Claims, 17 Drawing Sheets

(56) References Cited

OTHER PUBLICATIONS

Lombardy, et al., "Synthesis and DNA Interactions of Benzimidazole Dications Which Have Activity Against Opportunistic Infections" *J. Med. Chem.* 39:1452-1462 (1996).

Marques, et al., "Toward an Understanding of the Chemical Etiology for DNA Minor-Groove Recognition by Polyamides" *Helvetica Chimica Acta* 85:4485-4517 (2002).

Matsuba, et at, "A Novel Synthetic DNA Minor Groove Binder, MS-247: Antitumor Activity and Cytotoxic Mechanism" *Cancer Chemother. Pharmacol.* 46:1-9 (2000).

Melander, et al., "Discrimination of A/T Sequences in the Minor Groove of DNA Within a Cyclic Polyamide Motif" *Chem. Eur. J.* 24:4487-4497 (2000).

Minehan, et al., "Molecular Recognition of DNA by Hoechst Benzimidazoles: Exploring Beyond the Pyrrole-Imidazole-Hydroxypyrrole Polyamide-Pairing Code" *Helvetica Chimica Acta* 83:2197-2213, 2000.

Nguyen, et at, "Alternate Hetercycles for DNA Recognition: An N-Methylpyrazole/N-Methylpyrrole Pair Specifies for A•T/T•A Base Pairs" *Bioorg. & Med. Chem.* 9:7-17 (2001).

Pelton and Wemmer, "Structural Characterization of a 2:1 Distamycin a$\cdot $d(CGCAAATTGGC) Complex by Two-Dimensional NMR" *Proc Natl Aced Sci USA* 86:5723-5727 (1989).

Pjura, et al., "Binding of Hoechst 33258 to the Minor Groove of B-DNA" *J. Mol. Biol.* 197:257-271 (1987).

Renneberg and Dervan; "Imidazopyridine/Pyrrole and Hydroxybenzimidazole/Pyrrole Pairs for DNA Minor Groove Recognition" *JACS* 125:5707-5716 (2003).

Satz and Bruice, "Recognition of Nine Base Pairs in the Minor Groove of DNA by a Tripyrrole Peptide-Hoechst Conjugate" *J. Am. Chem. Soc.* 123:2469-2477 (2001).

Teng, et al., "The Molecular Structure of the Complex of. Hoechst 33258 and the DNA Dodecamer d(CGCGAATTCSCS)" *Nucleic Acids Res.* 16:2671-2690 (1988).

Trauger, and Dervan, "Footprinting Methods for Analysis of Pyrrole-Imidazole Polyamide/DNA Complexes" *Methods Enzymol.* 340:450-466 (2001).

Wang, et al., "Evaluation of the Influence of Compound Structure on Stacked-Dimer Formation in the DNA Minor Groove" *Biochemistry* 40:2511-2521 (2001).

Wurtz, et al., "Inhibition of DNA Binding by ND-$_k$B with Pyrrole-Imidazole Polyamides" *Biochemistry* 41:7604-7609 (2002).

Zhang, W. et al., A novel dicationic polyamide ligand binds in the DNA minor groove as a dimmer. *FEBS Lett.*, 509: 85-89, (2001).

*Communication pursuant to Article 94(3) EPC* dated Nov. 13, 2009 from the EPO for EPO Patent Application No. 04 717 463.6-1521.

Supplementary European Search Report for EPO Application No. EP 04 71 7463, Jul. 23, 2007.

\* cited by examiner

| Oligomer | Representative Six-Membered Heterocyclic Oligomers of the Invention | Oligomer | Related Five-Membered Heterocyclic Oligomers |
|---|---|---|---|
| A | | N | |
| B | | Q | |

Fig. 1a

| | Oligomer | Representative Six-Membered Heterocyclic Oligomers of the Invention | Oligomer | Related Five-Membered Heterocyclic Oligomers |
|---|---|---|---|---|
| | E | | S | |
| | F | | V | |

Fig. 1c

| Polyamide | 5'-cTGTATAt-3' | 5'-cTGTTTAt-3' | 5'-cTGTGTAt-3' | 5'-cTGTCTAt-3' |
|---|---|---|---|---|
| A | $3.7 \times 10^9$ (±0.4) [3] | $2.3 \times 10^9$ (±0.4) [5] | $1.2 \times 10^{10}$ (±0.2) | $5.4 \times 10^9$ (±1.5) [2] |
| N | $5.5 \times 10^8$ (±0.3) [4] | $2.9 \times 10^8$ (±0.2) [8] | $2.3 \times 10^9$ (±0.3) | $2.7 \times 10^8$ (±0.4) [9] |
| B | $3.1 \times 10^7$ (±0.9) [18] | $5.7 \times 10^8$ (±0.4) | $\leq 7 \times 10^6$ [≥80] | / |
| Q | $\leq 2 \times 10^7$ [≥20] | $4.1 \times 10^8$ (±1.4) | / | / |
| C | $7.8 \times 10^9$ (±0.8) [2] | $1.1 \times 10^{10}$ (±0.1) | $1.4 \times 10^9$ (±0.3) [8] | $2.6 \times 10^9$ (±0.3) [4] |
| P | $3.3 \times 10^9$ (±1.1) [2] | $6.9 \times 10^9$ (±0.8) | $\leq 3 \times 10^8$ [≥23] | $8.6 \times 10^8$ (±0.7) [8] |

*Fig. 4*

Specificity Of Bi, Hz, and Ip Pairings[a]
| pair  | T·A | A·T | G·C | C·G |
|-------|-----|-----|-----|-----|
| Bi/Py | +   | +   | −   | −   |
| Hz/Py | +   | −   | −   | −   |
| Ip/Py | −   | −   | +   | −   |
[a] Favored (+), disvafored (−)
*Fig. 5*
Benzimidazole-Pyrrole Polyamide D
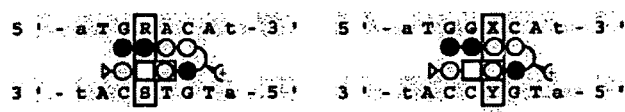
Benzimidazole-Imidazole Polyamide E
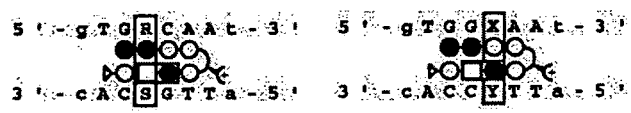
Benzimidazole-Hydroxypyrrole Polyamide F
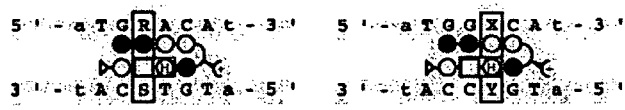
*Fig. 6*

| Polyamide on pPWF2 | 5'-aTGAACAt-3' | 5'-aTGTACAt-3' | 5'-aTGGACAt-3' | 5'-aTGCACAt-3' |
|---|---|---|---|---|
| R | 4.4 (± 1.2) x $10^8$ [61] | ≤ 1.0 x $10^8$ [≥270] | 2.7 (± 0.5) x $10^{10}$ | ≤ 1.0 x $10^8$ [≥270] |
| D | 3.9 (± 0.2) x $10^9$ [13] | 3.3 (± 0.3) x $10^9$ [15] | 4.9 (± 0.1) x $10^{10}$ | 9.0 (± 0.5) x $10^8$ [54] |
| T | ≤ 3 x $10^7$ [?127] | ≤ 1 x $10^7$ [?380] | 3.8 (± 0.2) x $10^9$ | ≤ 1.0 x $10^7$ [≥380] |
| F | 3.3 (± 0.7) x $10^8$ [76] | 2.4 (± 0.4) x $10^8$ [104] | 2.5 (± 0.4) x $10^{10}$ | 1.0 (± 0.3) x $10^8$ [250] |
| Polyamide on pCAB1 | 5'-gTGAACAt-3' | 5'-gTGTACAt-3' | 5'-gTGGACAt-3' | 5'-gTGCACAt-3' |
| S | ≤ 1.0 x $10^8$ [≥52] | ≤ 1.0 x $10^7$ [≥520] |  | ≤ 1.0 x $10^7$ [≥520] |
| E | 7.9 (± 1.4) x $10^8$ [39] | 6.2 (± 1.4) x $10^8$ [50] | 3.1 (± 0.5) x $10^{10}$ | 4.0 (± 0.7) x $10^8$ [78] |

*Fig. 9*

| Polyamide on pAU2 | 5'-aTGGACAt-3' | 5'-aTGGTCAt-3' | 5'-aTGGGCAt-3' | 5'-aTGGCCAt-3' |
|---|---|---|---|---|
| R | 4.9 (± 1.8) x $10^{10}$ | 4.9 (± 0.2) x $10^{10}$ | 2.0 (± 0.5) x $10^9$ [25] | 4.5 (± 0.8) x $10^9$ [11] |
| D | 2.7 (± 1.0) x $10^{10}$ [13] | 3.6 (± 0.9) x $10^{10}$ | 3.4 (± 0.6) x $10^9$ [11][e] | 5.7 (± 0.5) x $10^9$ [6][e] |
| T | 8.9 (± 1.3) x $10^9$ | 1.3 (± 0.1) x $10^9$ [7] | 1.8 (± 0.4) x $10^8$ [49] | 1.7 (± 0.6) x $10^8$ [52] |
| F | 1.8 (± 0.7) x $10^{10}$ | 2.5 (± 0.3) x $10^9$ [7] | 5.8 (± 1.8) x $10^8$ [31] | 7.0 (± 0.6) x $10^8$ [25] |
| Polyamide on pCAB1 | 5'-gTGGACAt-3' | 5'-gTGGTCAt-3' | 5'-gTGGGCAt-3' | 5'-gTGGCCAt-3' |
| S | ≤ 1.0 x $10^8$ [≥350] | ≤ 1.0 x $10^7$ [≥35] | ≤ 1.0 x $10^7$ [≥350] | 3.5 (± 0.5) x $10^9$ |
| E | ? 1.0 x $10^8$ [≥190] | 1.62 (± 0.1) x $10^9$ [12] | 2.8 (± 0.3) x $10^8$ [68] | 1.9 (± 0.3) x $10^{10}$ |

*Fig. 10*

Hydroxypyrrole and Hydroxybenzimidaxole Hairpins: $K_a [M^{-1}]^{a,b}$

| Polyamide Oligomer | A·T | T·A | G·C | C·G |
|---|---|---|---|---|
| G | $5.7 (\pm 0.4) \times 10^8$ | $5.5 (\pm 0.2) \times 10^9$ | ? $1.0 \times 10^7$ | ? $1.0 \times 10^7$ |
| J | $1.4 (\pm 0.3) \times 10^9$ | $3.2 (\pm 0.6) \times 10^8$ | ? $1.0 \times 10^7$ | ? $1.0 \times 10^7$ |

Multiple hydroxypyrrole and hydroxybenzimidazole ring pairings: $K_a$ [M$^{-1}$]$^{a,b}$

| Polyamide Oligomer | 5'-aGTACt-3' | 5'-aGAACt-3' | 5'-aGATCt-3' |
|---|---|---|---|
| H | 4.6 (± 0.8) × 10$^8$ | 3.2 (± 0.4) × 10$^7$ | 1.7 (± 0.5) × 10$^7$ |
| K | 4.5 (± 0.7) × 10$^8$ | 3.3 (± 0.7) × 10$^8$ | 4.4 (± 0.9) × 10$^8$ | a) Values reported are the mean values at least three DNase I footprinting titration experiments, with the standard deviation given in parenthesis. b) Assays were performed at 22 °C in a buffer of 10 mM Tris·HCl, 10mM KCl, 10 mM MgCl$_2$, and 5 mM CaCl$_2$ at pH 7.0.

*Fig. 17*

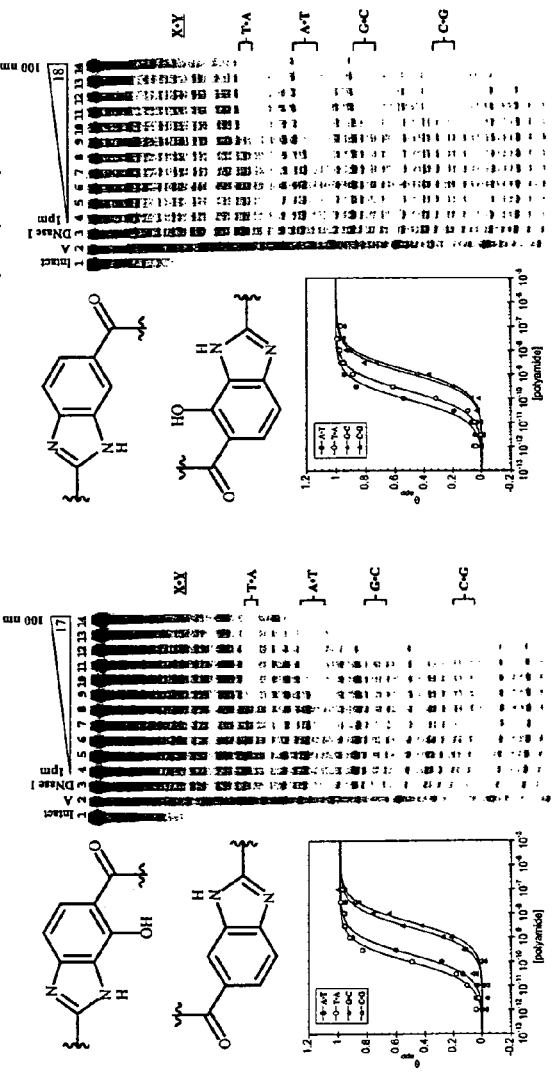

*Fig. 18*

Hydroxybenzimidole/Benzimidazole Pairings: $K_a$ [$M^{-1}$]$^{a,b}$

| Polyamide Oligomer | A·T | T·A | G·C | C·G |
|---|---|---|---|---|
| I | 4.1 (± 0.4) x 10$^9$ | 1.0 (± 0.3) x 10$^{10}$ | 2.4 (± 0.7) x 10$^8$ | 3.2 (± 0.5) x 10$^8$ |
| L | 1.1 (± 0.4) x 10$^{10}$ | 4.5 (± 0.4) x 10$^9$ | 8.1 (± 0.8) x 10$^8$ | 1.0 (± 0.7) x 10$^9$ |

*Fig. 19*

SEQUENCE LISTING

<160> NUMBER OF SEQ ID NOS: 10

<210> SEQ ID NO 1
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gatcaggctg tctatggacg gctgctgtgt atggacggct gctgtttatg gacggctgct    60
gtatatggac ggctgggcga                                                80

<210> SEQ ID NO 2
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
agcttcgccc agccgtccat atacagcagc cgtccataaa cagcagccgt ccatacacag    60
cagccgtcca tagacagcct                                                80

<210> SEQ ID NO 3
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cccggggatc atgaacatcg atctctatgt acatgctatg cgatggacat atcagctatg    60
cacattcgat ctctatgcta t                                              81

<210> SEQ ID NO 4
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cccggggatc agtgacaatc gatctctgtg tcaatgatat gcggtggcaa tatgagctgt    60
gccaattcga tctctatgat a                                              81

<210> SEQ ID NO 5
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cccggggatc atggacatcg atctctatgg tcatgctatg cgatgggcat atcagctatg    60
gccatagctt ggcgtaatca t                                              81

```
<210> SEQ ID NO 6
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cccggggatc agtggaaatc gatctctgtg gtaatgatat gcggtgggaa tatgagctgt      60
ggcaattcga tctctatgat a                                                81

<210> SEQ ID NO 7
<211> LENGTH: 103
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tagctgtgta atcatggcca tagctgtgta atcatgggca tagctgtgta atcatggaca      60
tagctgtaag cttggcgtaa tcatggtcat agctgtttcc tgt                       103

<210> SEQ ID NO 8
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tggatgctgg ttagtacttg gatgctggtt agaacttgga tgctggttag atcttggatg      60
ctaa                                                                   64

<210> SEQ ID NO 9
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cgcaaattgg c                                                           11

<210> SEQ ID NO 10
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gaagcttggc gta                                                         13
```

ALTERNATIVE HETEROCYCLES FOR DNA RECOGNITION

CROSS-REFERENCE TO RELATED PATENT APPLICATIONS

This application claims the benefit of U.S. Provisional Application No. 60/452,039, filed Mar. 4, 2003, and U.S. Provisional Application No. 60/452,180, also filed Mar. 4, 2003, the entire contents of both of which are incorporated herein by reference.

STATEMENT REGARDING FEDERAL FUNDING

Support for the research disclosed herein may have been provided by the National Institutes of Health under Grant No. NIH GM 27681. Accordingly, the United States may have certain rights in the invention.

FIELD OF THE INVENTION

The present invention relates to oligomers comprising fused six-membered cyclic monomers, wherein such oligomers are capable of binding to predetermined sequences on double stranded DNA. This invention is also related to detection of specific DNA sequences and modulation of transcription of target genes.

BACKGROUND OF THE INVENTION

The information provided herein and references cited are provided solely to assist the understanding of the reader, and does not constitute an admission that any of the references or information are prior art to the present invention.

With the explosion of techniques for the synthesis, analysis and manipulation of nucleic acids, numerous new opportunities have arisen in diagnostics and therapeutics. In research there is substantial interest in being able to identify DNA sequences, which may be associated with specific organisms, alleles, mutations, and the like, to understand particular genetic processes, to identify diseases, for forensic medicine, etc. Also, for many purposes, one may wish to modulate the expression of a target gene, so as to identify the function of such gene, or the cellular changes brought about by changes in the expression of such gene. In therapeutics, one may wish to inhibit the proliferation of cells, such as bacterial, fungal and chlamydia cells, which may act as pathogens, of viruses, of mammalian cells, where proliferation results in adverse effects on the host, or other situations. In vivo, one may provide for reversible or irreversible knock out, so that information can be generated on fetal development, or the effect on the organism of reduced levels of one or more genetic products.

Polyamide oligomers of nitrogen-containing five-membered heterocycles can be used to bind predetermined sequences on double stranded DNA (dsDNA). DNA recognition by polyamide oligomers depends on a code of side-by-side amino acid pairings that are oriented in the amino to carboxyl direction with respect to the 5'-3' direction of the DNA helix. Thus, polyamide oligomers bind dsDNA in an antiparallel fashion and in a stoichiometric ratio of 1:2, oligomer to DNA (Dervan et al., "Sequence-Specific DNA Recognition by Polyamides," *Current Opinion in Chemical Biology*, Vol. 3: 688, 1999). Antiparallel pairs of certain five-membered heterocycles preferentially bind to specific base pairs on duplex DNA. These antiparallel pairs have proven useful for the recognition of hundreds of predetermined DNA sequences by polyamide oligomers. Listed below in Table 1 are representative polyamide pairs of five-membered heterocycles and the DNA pairs that they preferentially bind to, referred to herein as the "pairing rules."

TABLE 1

Pairing Rules for Five-Membered Heterocyles

| Polyamide Pair* | DNA base pair recognition |
|---|---|
| Im/Py | G·C |
| Py/Im | C·G |
| Hp/Py | T·A |
| Py/Hp | A·T |

*Im = N-methyl imidazole; Py = N-methyl pyrrole; Hp = 3-hydroxypyrrole

The five-membered heterocycles described thus far in DNA-binding polyamide oligomers are analogues of the pyrrole ring. Their chemical design mimics the natural products netropsin and distamycin A, molecules which bind the minor groove of DNA (Arcamone, F. et al., "Structure and Synthesis of distamycin A, *Nature*, Vol. 203: 1064, 1964; Pelton, J. G. et al., "Structural characterization of a 2:1 distamycin-A-D(CG-CAAATTGGC) (SEQ ID NO: 9) complex by two-dimensional NMR," *Proc Natl Acad Sci USA*, Vol. 86: 5723-5727, 1989).

Efforts have been devoted to extend the ensemble of five-membered heterocycles that are capable of cooperatively pairing with each other to recognize specific DNA base pairs. These efforts have, in part, been motivated by the instability of the Hp heterocycle towards acids and free radicals. Polyamide oligomers containing Hp are susceptible to such degradation, and a robust replacement for use in biological applications is desired.

A search for new five-membered heterocycles and new five-membered heterocycle pairs for sequence determination was recently attempted with little success (Marques, M. et al., "Toward an Understanding of the Chemical Etiology for DNA Minor-Groove Recognition by Polyamides," *Helvetica Chimica Acta*, Vol. 85: 4485-4517, 2002). Using molecular modeling from an X-ray crystallography structure of a polyamide oligomer bound to duplex DNA, analogs of the existing five-membered heterocycles were designed to optimize binding to the curvature and twist of minor-groove DNA. Analogs of Py (1-methyl-1H-pyrazole (Pz) and 1H-pyrrole (Nh)), Im (5-methylthiazole (Nt) and furan (Fr)), and Hp (3-hydroxythiopene (Ht)) were synthesized and investigated in polyamide pairs. Additional sulfur containing pyrrole analogs (4-methylthiazole (Th), 3-methylthiophene (Tn), and thiophene (Tp)) were also studied. The chemical structures of these analogs are shown below:

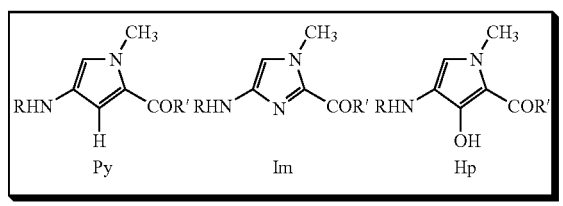

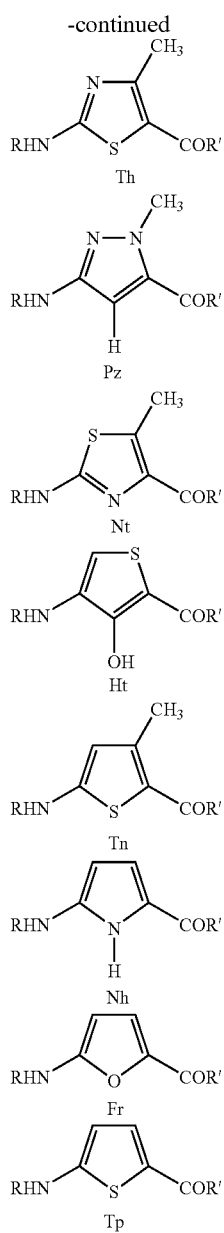

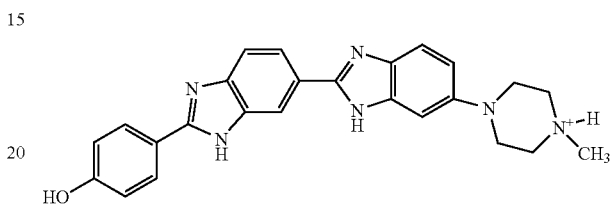

These eight analogs of the five-membered heterocycles Py, Im, and Hp and their corresponding pairs did not result in new sequence discrimination. These findings imply that DNA recognition by the existing pairs, namely Im/Py, Py/Im, Hp/Py, and Py/Hp, may be facilitated within a narrow structural window; thus, a search for new five-membered heterocycles may be of limited value.

Six-membered heterocycles represent a new class of heterocycles that may be employed in oligomers which bind DNA. Certain small molecule ligands known to bind the minor groove of DNA with relatively high affinities contain six-membered heterocycles and fused heterocycles, such as benzimidazole, imidazopyridines, and indoles (R. L. Lombardy, et al., *J. Med. Chem.*, 39: 1452-1462, 1996; Minehan, T. G. et al. *Helv. Chim. Acta*, 83: 2197-2213, 2000; Wang, L. et al., *Biochemistry*, 40: 2511-2521, 2001; Zhang, W. et al., *FEBS Lett.*, 509: 85-89, 2001; Ji, Y.-H. et al., *Bioorg. Med. Chem.*, 9: 2905-2919, 2001; Satz, A. L. et al., *J. Am. Chem. Soc.*, 123: 2469-2477, 2001; Behrens, C. et al., *Bioconjugate Chem.*, 12: 1021-1027, 2001; Matsuba, Y. et al., *Cancer Chemother. Pharmacol.*, Vol. 46: 1-9, 2000).

Hoechst 33258, which comprises a bis-benzimidazole, an N-methylpiperazine, and a phenol moiety, is an example of a fused six-membered cyclic derivative (P. E. Pjura, K. Grzeskowiak, R. E. Dickerson, *J. Mol. Biol.*, 197: 257-271, 1987; M. Teng, N. Usman, C. A. Frederick, A. Wang, *Nucleic Acids Res.*, 16: 2671-2690, 1988; S. Kumar, B. Yadagiri, J. Zimmermann, R. T. Pon, J. W. Lown, *J. Biomol. Struct. Dyn.*, 8: 331-357, 1990). The chemical structure of Hoechst 33258 is shown below:

Hoechst 33258 is a highly fluorescent dye which binds the minor groove of DNA at A•T rich tracks. Oligomers of the Hoechst benzimidazoles have been synthesized and studied for DNA recognition (Minchan, T. G. et al., "Molecular Recognition of DNA by Hoechst Benzimidaoles: Exploring Beyond the Pyrroe-Imidazol-Hydroxypyrrole Polyamide-Pairing Code," *Helvetica Chimica Acta*, Vol. 83: 2197-2213, 2000). These benzimidazole oligomers also show preference for A•T rich sequences, as well as for 5'-WGWWW-3' and 5'-WCWWW-3', where W=A or T.

While Hoechst 33258 and its corresponding benzimidazole oligomers bind A•T rich DNA in a 1:1 ratio, such compounds do not recognize specific nucleotide base pairs across the duplex, such as in the pairing rules described above for five-membered heterocyclic polyamide oligomers. Other six-membered heterocyclic DNA binding ligands reported thus far also do not recognize specific mononucleotide base pairs across the duplex.

SUMMARY OF THE INVENTION

In accordance with the present invention, there are provided novel oligomers comprising fused six-membered cyclic monomers which bind specific base pairs on dsDNA in a 1:2 ratio of oligomer to DNA nucleotide. These oligomers represent a novel class of DNA binding ligands which are capable of binding to predetermined target sequence on dsDNA.

Oligomeric compounds presented herein are capable of forming a specific complex at targeted sequences within dsDNA. Oligomeric compounds presented herein may also be used to detect the presence of a specific nucleotide sequence in dsDNA. Additionally, oligomeric compounds herein can be used to isolate target dsDNA from a sample comprising a mixture of dsDNA. Furthermore, oligomeric compounds herein are applicable in modulating transcription of a target gene in a cell. Effective amounts of oligomeric compounds herein may be administered to a subject as a means of treating cancer by reducing the level of transcription of a target oncogene.

Thus, in a first aspect, the present invention provides novel oligomers comprising monomers corresponding to Formula (I):

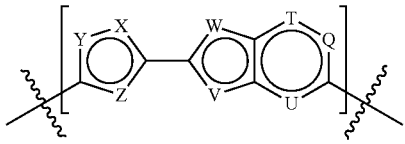
(I)

or a pharmaceutically acceptable salt thereof, wherein:
each of Q, T, and U is independently —$CR_1$ or N;
each of V, W, X, Y and Z is independently —$CR_2$, N, —$NR_3$, O, or S;
each $R_1$ is independently H, halogen, —OH, —OMe, —OAc, —$NH_2$, —NHAc, —$CH_3$, —SH, —$NO_2$, —CHO, —$SO_2H$, —S(O)$NH_2$, —(C≡C)(CN)$_3$, —CN, acetyl, $C_1$-$C_6$-alkyl, $C_1$-$C_6$-alkylamino; and
each of $R_2$ and $R_3$ is independently H, halogen, —OH, —OMe, —SH, —CN, —OAc, —$NH_2$, —NHAc, $C_1$-$C_6$-alkyl, $C_1$-$C_6$-alkylamino, $C_2$-$C_6$-alkenyl, $C_2$-$C_6$-alkynyl.

The present invention provides oligomers of Formula (I) corresponding to Formula (II):

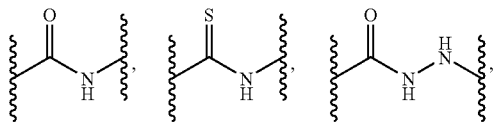
(II)

or a pharmaceutically acceptable salt thereof, wherein:

each $R_4$ is independently selected from the group consisting of H, halogen, NO, N-acetyl, CHO, benzyl, $C_1$-$C_6$-alkyl, $C_2$-$C_6$-alkenyl, $C_2$-$C_6$-alkynyl, $C_1$-$C_6$-alkylamino, $C_1$-$C_6$-alkyldiamino, $C_1$-$C_6$-alkylcarboxylate, and

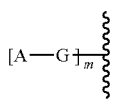

wherein m is 0-11;

each $R_5$ is independently selected from the group consisting of H, halogen, NO, N-acetyl, CHO, benzyl, $C_1$-$C_6$-alkyl, $C_2$-$C_6$-alkenyl, $C_2$-$C_6$-alkynyl, $C_1$-$C_6$-alkylamino, $C_1$-$C_6$-alkyldiamino, $C_1$-$C_6$-alkylcarboxylate, and

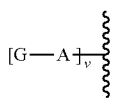

wherein v is 0-11;

each A is independently

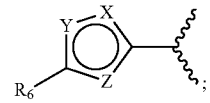

each $R_6$, is independently H, halogen, NO, N-acetyl, CHO, benzyl, $C_1$-$C_{12}$-alkyl, $C_2$-$C_{12}$-alkenyl, $C_2$-$C_{12}$-alkynyl, $C_1$-$C_{12}$-alkylamino, $C_1$-$C_{12}$-alkyldiamino, $C_1$-$C_{12}$-alkylamido, $C_1$-$C_{12}$-alkyldiamido, $C_1$-$C_{12}$-aminoalkylamido, $C_1$-$C_{12}$-aminoalkyldiamido, or $C_1$-$C_{12}$-alkylcarboxylate, with the proviso that when either m>1 or v>1, $R_6$ is a covalent bond;

each G is independently

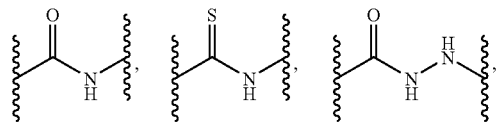

-continued

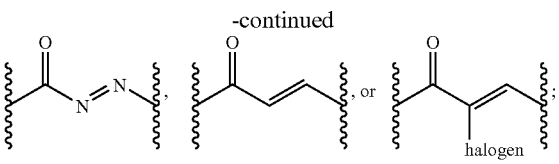

L is selected from the group consisting of $C_1$-$C_6$-alkyleneamino, $C_1$-$C_6$-alkylenediamino, $C_1$-$C_6$-alkyleneamido, $C_1$-$C_6$-alkylenecarboxylene, $C_1$-$C_6$-alkylene, $C_2$-$C_6$-alkenylene, and $C_2$-$C_6$-alkynylene;
n is 0-11;
p is 0-11;
q is 0-11; and
t is 0-11;
wherein either n or t is at least 1; and
wherein m+n+p=v+q+t and 20≧m+n+p≧2.

As used herein, reference to a certain element such as hydrogen or H is meant to include all isotopes of that element. For instance, if a group is defined to include hydrogen or H, it also can include deuterium and/or tritium.

Compounds of the present invention may have asymmetric centers and may occur, except when specifically noted, as mixtures of stereoisomers or as individual diastereomers, or enantiomers, with all isomeric forms being included in the present invention. Compounds of the present invention embrace all conformational isomers, including, for example, cis- or trans-conformations. Compounds of the present invention may also exist in one or more tautomeric forms, including both single tautomers and mixtures of tautomers.

Oligomers of the present invention may be substituted with various atoms as noted. The phrase "substitution" refers to an atom or group of atoms that has been replaced with another substituent. The phrase "substituted" includes all levels of substitution, e.g. mono-, di-, tri-, tetra-, or penta-substitution, where such substitution is chemically permissable. Substitutions can occur at any chemically accessible position and on any atom, such as substitution(s) on carbon and any heteroatom, preferably oxygen, nitrogen, or sulfur. For example, substituted oligomers are those where one or more bonds to a hydrogen or carbon atom(s) contained therein are replaced by a bond to non-hydrogen and/or non-carbon atom(s). Substitutions can include, but are not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups.

The phrase "substituted" or "substitution" also includes substitution with an optionally substituted hydrocarbyl moiety containing one or more of the following: —O—, —S—, —NR—, —O—C(O)—, —O—C(O)—O—, —O—C(O)—NR—, —NR—C(O)—, —NR—C(O)—O—, —NR—C(O)—NR—, —S—C(O)—, —S—C(O)—O—, —S—C(O)—NR—, —S(O)—, —S(O)$_2$—, —O—S(O)$_2$—, —O—S(O)$_2$—O—, —O—S(O)$_2$—NR—, —O—S(O)—, —O—S(O)—O—, —O—S(O)—NR—, —O—NR—C(O)—, —O—NR—C(O)—O—, —O—NR—C(O)—NR—, —NR—O—C(O)—, —NR—O—C(O)—O—, —NR—O—C(O)—NR—, —O—NR—C(S)—, —O—NR—C(S)—O—, —O—NR—C(S)—NR—, —NR—O—C(S)—, —NR—O—C(S)—O—, —NR—O—C(S)—NR—, —O—C(S)—, —O—C(S)—O—, —O—C(S)—NR—, —NR—C(S)—, —NR—C(S)—O—, —NR—C(S)—NR—, —S—S(O)$_2$—, —S—S(O)$_2$—O—, —S—S(O)$_2$—NR—, —NR—O—S(O)—, —NR—O—S(O)—O—, —NR—O—S(O)—NR—, —NR—O—S(O)$_2$—, —NR—O—S(O)$_2$—O—, —NR—O—S(O)$_2$—NR—, —O—NR—S(O)—, —O—NR—S(O)—O—, —O—NR—S(O)—NR—, —O—NR—S(O)$_2$—O—; —O—NR—S(O)$_2$—NR—, —O—NR—S(O)$_2$—, —O—P(O)R$_2$—, —S—P(O)R$_2$—, or —NR—P(O)R$_2$—.

The phrase "oligomer" refers to a molecule comprising a plurality of monomer units connected to each other. Monomer units within an oligomer may be the same or different from each other. The number of repeating monomer units can vary depending on the particular application for which the oligomer is employed. Oligomers of the invention can comprise from 2 to 20 monomeric units, such as from 4 to 15 monomeric units, such as from 8 to 12 monomeric units. The connectivity between monomer units can be the same or different throughout the oligomer.

The phrase "halogen" or "halide" refers to —F, —Cl, —Br, or —I.

The phrase "alkyl" refers to straight, branched chain, or cyclic hydrocarbyl groups comprising from 1 to 20 carbon atoms. The phrase "alkyl" includes straight chain alkyl groups such as methyl, ethyl, propyl, butyl, pentyl, hexyl, heptyl, octyl, nonyl, decyl, undecyl, dodecyl, and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, and —CH(CH$_2$CH$_3$)CH(CH$_3$)CH(CH$_3$)(CH$_2$CH$_3$). Thus, alkyl groups includes primary alkyl groups, secondary alkyl groups, and tertiary alkyl groups. Preferred alkyl groups include alkyl groups having from 1 to 10 carbon atoms while even more preferred such groups have from 1 to 5 carbon atoms. Most preferred alkyl groups include straight and branched chain alkyl groups having from 1 to 3 carbon atoms and include methyl, ethyl, propyl, and —CH(CH$_3$)$_2$. Alkyl groups can further be substituted as defined above.

The phrase "alkylene" refers to divalent straight, branched chain or cyclic alkyl groups having 1 up to about 20 carbon atoms, preferably 2-10 carbon atoms. "Substituted alkylene" refers to alkylene groups which can be substituted as defined above.

The phrase "alkenyl" refers to monovalent straight, branched chain or cyclic hydrocarbyl groups having at least one carbon=carbon double bond, and having 2 up to about 20 carbon atoms, preferably 2-10 carbon atoms. Alkenyl groups can further be substituted as defined above.

The phrase "alkenylene" refers to divalent straight, branched, or alkenyl groups, as defined above, having in the range of about 2 up to 20 carbon atoms. "Substituted alkenylene" refers to alkenylene groups which can be substituted as defined above.

The phrase "alkynyl" refers to monovalent straight, branched chain, or cyclic hydrocarbyl groups having at least one carbon=carbon triple bond, and having 2 up to about 20 carbon atoms, preferably 2-10 carbon atoms. Alkynyl groups can further be substituted as defined above.

The phrase "alkynylene" refers to divalent straight, branched, or cyclic alkynyl groups, as defined above, typically having in the range of about 2 up to 20 carbon atoms. "Substituted alkynylene" refers to alkynylene groups which can be substituted as defined above.

The phrase "alkylamino" refers to alkyl groups comprising a nitrogen atom. Alkylamino groups can comprise any level of nitrogen substitution, e.g. primary, secondary, or tertiary. Alkylamino groups may be further substituted as defined above.

The phrase "alkyldiamino" refers to alkyl groups comprising two nitrogen atoms. Alkyldiamines can comprise any level of nitrogen substitution, e.g. primary, secondary, or tertiary. Alkyldiamino groups may be further substituted as defined above.

The phrase "alkylcarboxylate" refers to alkyl groups comprising —C(O)O⁻ or —C(O)OH. Representative alkylcarboxylate groups can be of the formula RCOOH, wherein R is an alkyl group as defined above.

The phrase "alkylamido" refers to alkyl groups comprising an amide functionality of the following formula: —C(O)NRR' wherein R and R' are independently selected from hydrogen, acetyl, alkyl, alkenyl, alkynyl, and the like. Alkylamido groups may be further substituted as defined above.

The phrase "alkyldiamido" refers to alkyl groups comprising two amide functionalities of the following formula: —C(O)NRR' wherein R and R' are independently selected from hydrogen, acetyl, alkyl, alkenyl, alkynyl, and the like. Alkyldiamido groups may be further substituted as defined above.

The phrase "aminoalkylamido" refers to an alkylamino group, as defined above, further comprising an amide functionality of the following formula: —C(O)NRR' wherein R and R' are independently selected from hydrogen, acetyl, alkyl, alkenyl, alkynyl, and the like. Aminoalkylamido groups may be further substituted as defined above. A representative aminoalkylamido group is of the formula —C(O)NH(CH$_2$CH$_2$CH$_2$)N(CH$_3$)$_2$.

The phrase "aminoalkyldiamido" refers to an alkylamino group, as defined above, further comprising two amide functionalities of the following formula: —C(O)NRR' wherein R and R' are independently selected from hydrogen, acetyl, alkyl, alkenyl, alkynyl, and the like. Aminoalkyldiamido groups may be further substituted as defined above. A representative aminoalkyldiamide group is of the formula —C(O)NH(CH$_2$CH$_2$)C(O)NH(CH$_2$CH$_2$CH$_2$)N(CH$_3$)$_2$.

Embodiments of the invention include oligomers of Formula (I) where X is —NR$_3$ wherein R$_3$ is C$_1$-C$_6$-alkyl, such as —CH$_3$; where Z is —CR$_2$ wherein R$_2$ is —OH or H; where Z is N; where V is N; where T is —CR$_1$ wherein R$_1$ is H or —OH; where T is N; where Y is —CR$_1$ wherein R$_1$ is H. Other embodiments includes oligomers of Formula (II) where L is substituted C$_1$-C$_6$-alkylene, such as —CH$_2$CH$_2$CH(NH$_3^+$)—; where L is C$_1$-C$_6$-alkylene, such as —CH$_2$CH$_2$CH$_2$—; where G is

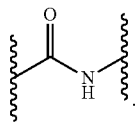 [SMILES: *NC(*)=O]

Further embodiments includes oligomers of Formula (II) where R$_4$ is

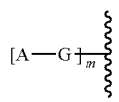

and m≠0; where at least one R$_4$ is hydrogen; where R$_5$ is

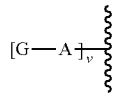

and v≠0; where at least one R$_5$ is C$_1$-C$_{12}$-alkylaminodiamido, such as —C(O)NH(CH$_2$)$_2$C(O)NH(CH$_2$)$_3$N(CH$_3$)$_2$. An embodiment is drawn to oligomers of the invention further comprising a detectable label. The phrase "detectable label" refers to any moiety which can be observed to facilitate detection of oligomers of the invention. Detectable labels include, for example, isotopes, fluorescent moieties, chemiluminescent moieties, magnetic moieities, and dyes.

In an aspect of the invention, oligomers of Formula (II) may be capable of binding to dsDNA in a sequence specific manner under physiological conditions. Such oligomers form high affinity complexes (i.e., K$_a$ ranging from about 10$^7$ to about 10$^{10}$ M$^{-1}$, such as about 10$^7$, 10$^8$, 10$^9$, or 10$^{10}$, with dsDNA at predetermined sequences. The phrase "binding to dsDNA in a sequence specific manner" refers to an oligomer's ability to form at least one complementary pair with at least one DNA specific pair on a dsDNA target sequence.

Oligomers of the invention can comprise two equal length chains of monomeric units connected by a linker, wherein each monomeric unit of each chain binds to a specific nucleotide. Thus, a pair of monomers can bind to a specific, complementary pair of nucleotides. For instance, the Ip/Py pair has sequence specificity for G•C; the Bi/Py pair has sequence specificity for T•A and/or A•T; the Hz/Py pair has sequence specificity for T•A; the Py/Hz pair has sequence specificity for A•T; the Hz/Bi pair has sequence specificity for T•A; the Bi/Hz pair having sequence specificity for A•T. Accordingly, consecutive pairs of monomers of the oligomer can bind to a specific DNA sequence on dsDNA. The amount of pairs of the oligomer that can bind to specific DNA sequence on dsDNA can be from 1 to 20, such as from 2 to 15, such as from to 8. Furthermore, in certain embodiments, oligomers of the invention may bind specific sequences which are located in the minor groove of dsDNA. It is generally understood by those skilled in the art that the basic structure of DNA in a living cell includes both major and minor grooves. For the purposes of describing the present invention, the minor groove is the narrow groove of DNA as illustrated in common molecular biology reference such as Lewin, B., Genes VI, Oxford University Press, New York (1997).

Oligomers of the invention may be brought together with dsDNA under a variety of physiological conditions. Physiological conditions are conditions which occur in vitro, in cell cultures, ex vivo or in vivo. Generally, the pH level in physiological conditions ranges from about 6.5 to 9, and the temperature ranges from about 4° C. to 45° C. Preferable physiological conditions are pH levels of 7-8 and temperatures of 37-42° C.

Another aspect of the invention is drawn to hairpin polyamide oligomers comprising at least one five-membered heterocycle wherein each five-membered heterocycle is independently selected from the group consisting of Py, Im, Hp, Fr, Nt, Pz, Ht, pyrrole, triazole, thiophene, and oxazole; at least one fused six-membered heterocycle independently selected from the group consisting of Ip, Hz, and Bi; and a linker comprising 2 to 12 carbon atoms.

The phrase "hairpin polyamide oligomer" refers to two polyamide chains of monomer units that are linked to each other by a covalent linker comprising 2 to 12 carbon atoms. The phrase "polyamide oligomer" refers to a plurality of monomer units which are connected to each other via an amide bond i.e. —C(O)NH—. In a hairpin polyamide oligomer, the linker which covalently links the two polyamide chains imparts an overall U-turn shape to the polyamide oligomer. Hairpin polyamide oligomers are well known in the art and are described, for example, in Church et al., "N-(2-chloroethyl)-N-nitrosoureas covalently bound to nonionic and monocationic lexitropsin dipeptides," *Biochemistry*, Vol. 29: 6827, 1990 and He et al., "Chemistry of phosphodiesters, DNA and models," *JACS*, Vol. 115: 7061, 1993.

The phrase "five-membered heterocycle" refers to a cyclic ring of five atoms, wherein at least one atom of the ring is a heteroatom. The five-membered heterocycle can be aromatic or non-aromatic. An example of a five-membered heterocycle is

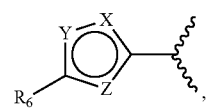

wherein X, Y and Z is independently —CR$_2$, N, —NR$_3$, O, or S and R$_6$, wherein R$_6$ is independently H, halogen, NO, N-acetyl, CHO, benzyl, C$_1$-C$_{12}$-alkyl, C$_1$-C$_{12}$-alkenyl, C$_1$-C$_{12}$-alkynyl, C$_1$-C$_{12}$-alkylamino, C$_1$-C$_{12}$-alkyldiamino, C$_1$-C$_{12}$-alkylamido, C$_1$-C$_{12}$-alkyldiamido, C$_1$-C$_{12}$-aminoalkylamido, C$_1$-C$_{12}$-aminoalkyldiamido, C$_1$-C$_{12}$-alkylcarboxylate, or a covalent bond; and wherein each of R$_2$ and R$_3$ is independently H, halogen, —OH, —OMe, —SH, —CN, —OAc, —NH$_2$, —NHAc, C$_1$-C$_6$-alkyl, C$_1$-C$_6$-alkylamino, C$_1$-C$_6$-alkenyl, or C$_1$-C$_6$-alkynyl. For instance, representative five-membered heterocycles include N-methyl pyrrole (Py), N-methyl imidazole (Im), 3-hydroxypyrrole (Hp), furan (Fr), 5-methylthiazole (Nt), 1-methyl-1H-pyrazole (Pz), 3-hydroxythiopene (Ht), pyrrole, triazole, thiophene, and oxazole.

The phrase "fused six-membered cyclic monomer" or "fused six-membered ring" refers to a ring of six atoms which is fused to another ring structure. Preferably, at least one atom in either ring structure is a heteroatom. Fused six-membered rings include 6-5 ring systems wherein both rings are aromatic. An example of a fused six-membered ring is

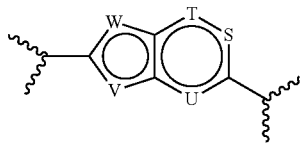

wherein each of S, T, and U is independently —CR$_1$ or N and each of V and W is independently —CR$_2$, N, —NR$_3$, O, or S, wherein each R$_1$ is independently H, halogen, —OH, —OMe, —OAc, —NH$_2$, —NHAc, —CH$_3$, —SH, —NO$_2$, —CHO, —SO$_2$H, —S(O)NH$_2$, —(C≡C)(CN)$_3$, —CN, acetyl, C$_1$-C$_6$-alkyl, or C$_1$-C$_6$-alkylamino; and each of R$_2$ and R$_3$ is independently H, halogen, —OH, —OMe, —SH, —CN, —OAc, —NH$_2$, —NHAc, C$_1$-C$_6$-alkyl, C$_1$-C$_6$-alkylamino, C$_1$-C$_6$-alkenyl, or C$_1$-C$_6$-alkynyl. For instance, representative fused six-membered rings include benzimidazole (Bi), imidazo[4,5-b]pyridine (Ip), and hydroxybenzimidazole (Hz).

The phrase "linker" refers to an aliphatic moiety comprising 2 to 12 carbon atoms which links, joins, attaches, or connects two equal length monomeric chains to form oligomers of the invention. Representative linkers which can be used in the present oligomers include C$_1$-C$_6$-alkylene, C$_1$-C$_6$-alkyleneamino, and aliphatic amino acids (connecting the chains via the amino and carboxyl terminal ends). For instance, exemplary linkers include aminopropylene, —CH$_2$CH$_2$CH$_2$—, beta-alanine, gamma-aminobutyric acid, or diaminobutyric acid (DAB).

The present invention also provides methods for preparing a polyamide oligomer having at least one fused six-membered ring. Methods presented herein comprise attaching an amino protected polyamide monomer to a prepared resin; coupling another amino protected monomer to form a polyamide oligomer; and optionally, repeating the coupling step with another amino protected monomer to form a polyamide oligomer of a desired length. Oligomers of the present invention are prepared by coupling at least one monomer comprising a protected amino group, a reactive carboxyl group, and a fused six-membered ring to the resin.

The phrase "prepared resin" refers to standard resins used in routine peptide coupling procedures which are prepared for use in heterocyclic coupling. Standard resins include, for example, Kaiser's oxime resin, which may be used to prepare oligomers of the invention. Stepwise coupling of amino protected heterocycles to form polyamide oligomers is a well known procedure in the art and is described, for example, in Baird, E. E., "Chemistry of phosphodiesters, DNA and models," *J. Am. Chem. Soc.*, Vol. 118, 6141-6146, 1996.

The phrase "protected amino group" refers to standard moieties used to protect reactive amines, e.g. amino protecting groups. Heterocyclic monomers can be protected with a variety of standard amino protecting groups, such as t-butoxycarbonyl (Boc) and 9-fluorenylmethoxycarbonyl (Fmoc), for instance.

The phrase "reactive carboxyl group" refers to standard moieties used to activate carboxyl groups, e.g. via carboxyl activating agents. Heterocyclic monomers comprising a carboxyl group substituent may be activated by a variety of standard activating agents, such as N,N'-dicyclohexylcarbodiimide (DCC), N,N'-diisopropylcarbodiimide (DIC) or O-benzotriazol-1-yl-N,N,N',N'-tetramethyluronium-hexafluorophosphate (HBTU), with or without 4-dimethylaminopyridine (DMAP), 1-hydroxybenzotriazole (HOBT), benzotriazol-1-yloxy-tris(dimethylamino)phosphonium-hexafluorophosphate (BOP), bis(2-oxo-3-oxazolidinyl) phosphine chloride (BOPCl), and the like.

The present invention also provides methods for forming specific complexes between target dsDNA and a polyamide oligomer comprising at least one fused six-membered ring, such as Ip, Hz, or Bi. By contacting dsDNA with a polyamide oligomer that is capable of binding to a specific sequence on said dsDNA, specific complexes can be formed between the polyamide oligomer and a target sequence on dsDNA. In certain embodiments, polyamide oligomers which form specific complexes with target dsDNA further comprise at least one five-membered heterocycle independently selected from the group consisting of Py, Im, Hp, Fr, Nt, Pz, Ht, pyrrole, triazole, thiophene, and oxazole.

The present invention also provides methods for detecting the presence of a specific sequence in a sample comprising dsDNA by contacting the sample with a polyamide oligomer comprising at least one fused six-membered ring and a detectable label. By contacting dsDNA with a polyamide oligomer that is capable of binding to a specific sequence on said dsDNA, specific complexes can be formed between the polyamide oligomer and a target sequence on dsDNA. The detectable label on the polyamide oligomer can be observed from the specific complexes, indicating the presence of a specific sequence. In certain embodiments, polyamide oligomers which form specific complexes with target dsDNA further comprise at least one five-membered heterocycle.

The present invention also provides methods for isolating target dsDNA from a sample comprising a mixture of dsDNA by contacting the sample with a polyamide oligomer comprising at least one fused six-membered ring. By contacting dsDNA with a polyamide oligomer that is capable of binding to a specific sequence on said dsDNA, specific complexes can be formed between the polyamide oligomer and a target sequence on dsDNA. The target dsDNA can then be isolated from the specific complex. In certain embodiments, polyamide oligomers which form specific complexes with target dsDNA further comprise at least one five-membered heterocycle.

The present invention also provides methods for modulating transcription of a target gene in a cell by contacting the cell with an effective amount of a polyamide oligomer comprising at least one fused six-membered ring. By contacting dsDNA with a polyamide oligomer that is capable of binding to a specific sequence on said target gene, such as sequences on transcriptional regulatory regions of said gene, specific complexes can be formed between the polyamide oligomer and the target gene. Formation of polyamide complexes at sequences on the target gene can modulate transcription of that gene, particularly when complexes are formed at transcriptional regulatory regions of the gene. In certain embodiments, polyamide oligomers which form specific complexes with the target gene further comprise at least one five-membered heterocycle. In certain embodiments, the cell is eukaryotic, such as a mammalian cell, as in a human cell. In other embodiments, the cell is prokaryotic, such as a bacterial cell. In certain embodiments, the target gene is any gene implicated in the manifestation or propogation of a disease state. For example, the target gene is viral or is an oncogene. In certain embodiments, the cell is in a subject, such as a mammal, as in a human.

The phrase "effective amount" refers to an amount of polyamide oligomer that is effective in achieving a desired effect for a particular application. Effective amounts can vary depending upon the specific polyamide oligomer and the accessibility of the sequence on dsDNA. Generally, ranges of amounts of polyamide oligomer effective in reducing transcription of a target gene in a cell are 1 pM-50 mM, such as 1 nM-100 µM, such as about 30 nM.

The present invention also provides methods for treating cancer by reducing the level of transcription of a target oncogene by administering to a subject an effective amount of a polyamide oligomer which comprises at least one fused six-membered ring. By contacting dsDNA with a polyamide oligomer that is capable of binding to a specific sequence on said oncogene, specific complexes can be formed between the polyamide oligomer and a target oncogene on dsDNA. Formation of polyamide complexes at specific sequences on the target oncogene reduces transcription of that oncogene, such as when complexes are formed at transcriptional regulatory regions of the oncogene. In certain embodiments, polyamide oligomers which form specific complexes with the target oncogene further comprise at least one five-membered heterocycle. In certain embodiments, the subject is a mammal, such as a human.

Additional embodiments will be apparent from the Figures, Detailed Description, and claims.

BRIEF DESCRIPTION OF THE FIGURES

FIG. 1a-1c illustrate the structures of representative oligomers of the invention in comparison to five-membered heterocyclic oligomers.

FIG. 4 illustrates the equilibrium association constants $K_a[M^{-1}]$ for Polyamide Oligomers A-C, N, Q, and P. The reported association constants are the average values obtained from three DNase I footprint titration experiments, with the standard deviation for each data set indicated in the experiments. Assays were carried out at 22° C. at pH 7.0 in the presence of 10 mM Tris-HCl, 10 mM KCl, 10 mM $MgCl_2$, and 5 mM $CaCl_2$ with an equilibration time of 12 h. Specificities are give in brackets under the $K_a$ values and calculated as $K_a$ (match)/$K_a$ (mismatch).

FIG. 5 is a table showing specificity of Bi, Hz, and Ip Pairings.

FIG. 6 illustrates the base pairing of polyamide oligomers D, E, and F bound to recognition sequences 5'-TGRACA-3', 5'-TGRCAA-3',5'-TGGXCA-3', and 5'-TGGXAA-3' (R, X. A, T, G or C). Ring pairing-DNA interactions investigated by quantitative DNase I footprint titrations are boxed.

FIG. 9 illustrates the equilibrium association constants $K_a[M^{-1}]$ and specificities for polyamide oligomers D-F, R, S, and V on plasmids pPWF2 and pCAB1 (R•S position).

FIG. 10 illustrates the equilibrium association constants $K_a[M^{-1}]$ and specificities for polyamide oligomers D-F, R, S, and V on plasmids pAU2 and pCAB2 (X•Y position).

```
5'-gAAGCTTGGCGTa-3'        (SEQ ID NO 10).
```

Figure 13:
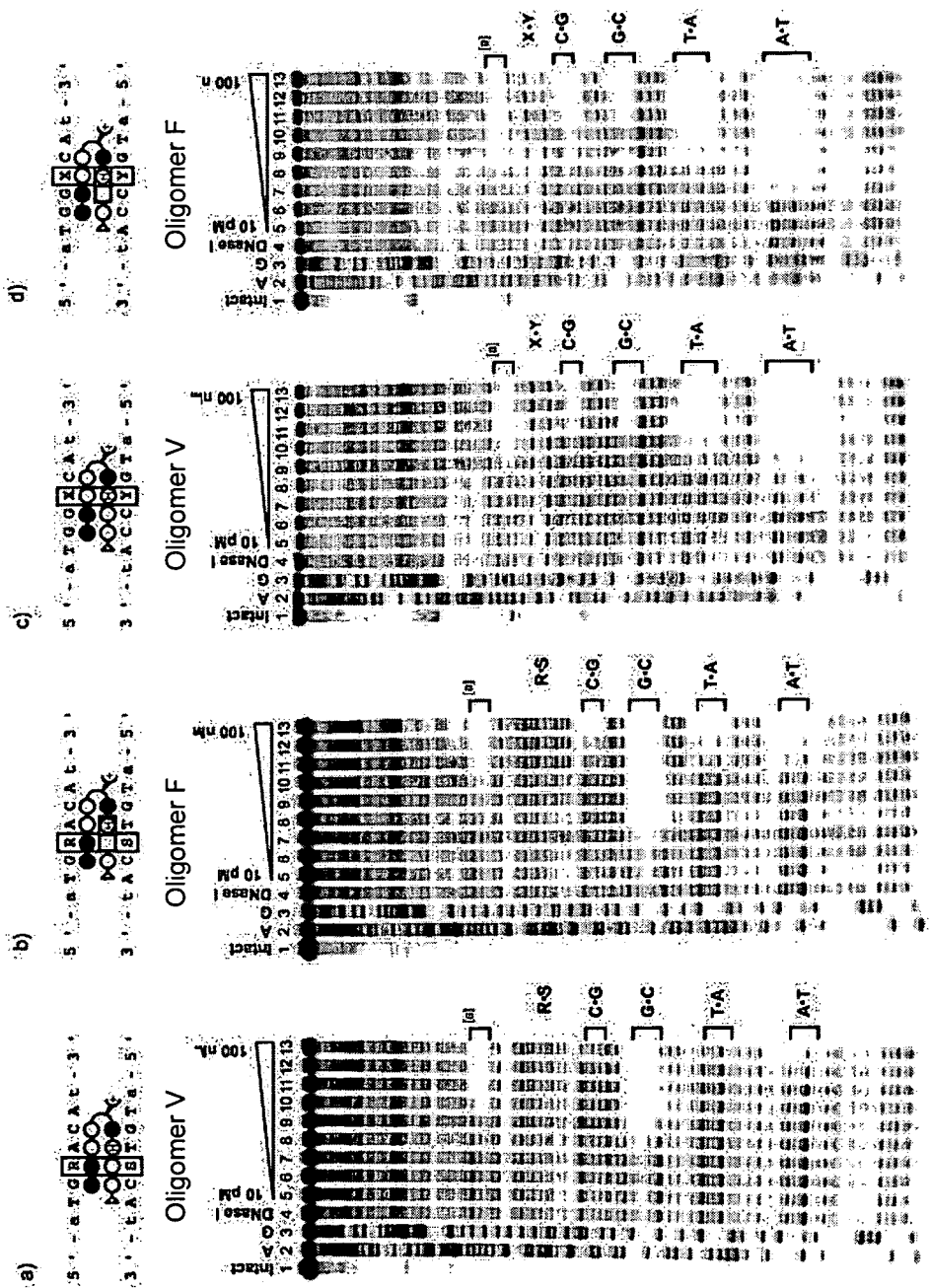

FIG. 13 is the quantitative DNase I footprint titration experiments on the 3'-$^{32}$P-labeled 283-bp and 263-bp EcoRI/PvuII restriction fragments derived from plasmids pPWF2 (a and b) and pAU2 (c and d), respectively. a) and c) polyamide oligomer V: lane 1, intact DNA; lane 2, A-specific reaction; lane 3, G-specific reaction; lane 4, DNase I standard; lanes 5±13: 10, 30, 100, 300 pm and 1, 3, 10, 30, 100 nm polyamide, respectively. b) and d) polyamide oligomer F: lane 1, intact DNA; lane 2, A specific reaction; lane 3, G specific reaction; lane 4, DNase I standard; lanes 5±13: 10, 30, 100, 300 pm and 1, 3, 10, 30, 100 nm polyamide, respectively. The analyzed 6-bp binding site locations are designated in brackets along the right side of each autoradiogram with their respective unique base pairs indicated. Schematic binding models of V and F with their putative binding sites are shown on the top side of the autoradiograms. Flanking sequences are designated in lower case while the binding site is given in capitals. The boxed R•S and X•Y base pairs indicate the positions that were examined in the experiments. [a] Additional 1-bp mismatch site for V and F; sequence 5'-aTGGTCAt-3'.

Figure 14:
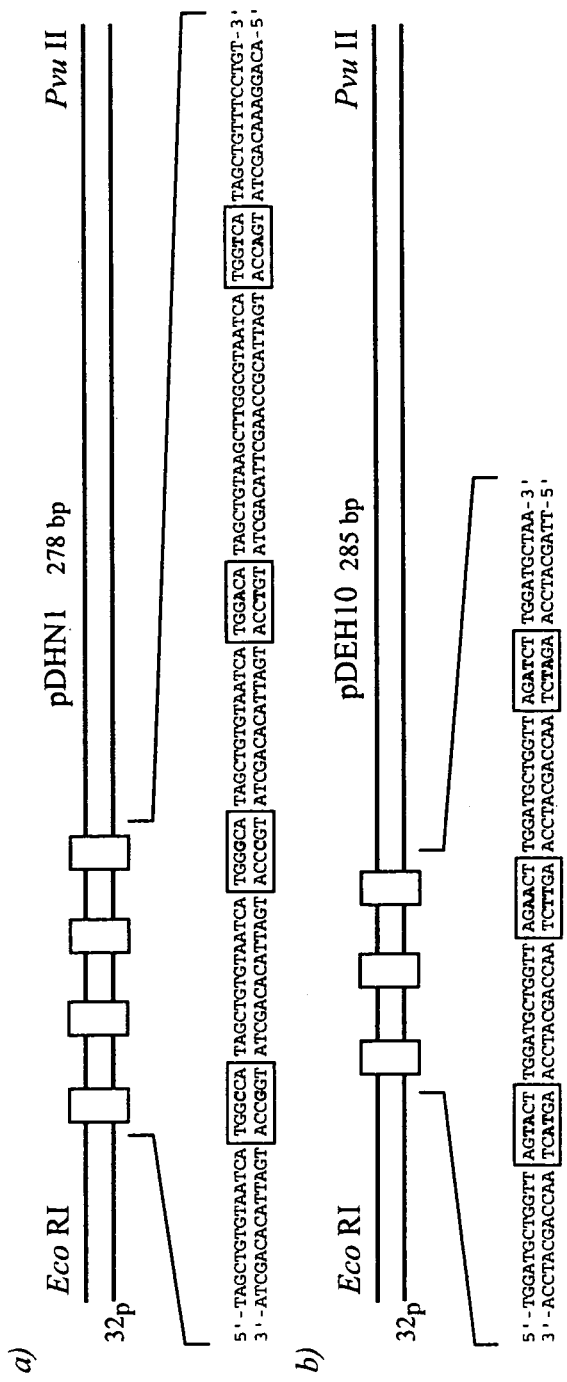
Figures 15, 16:
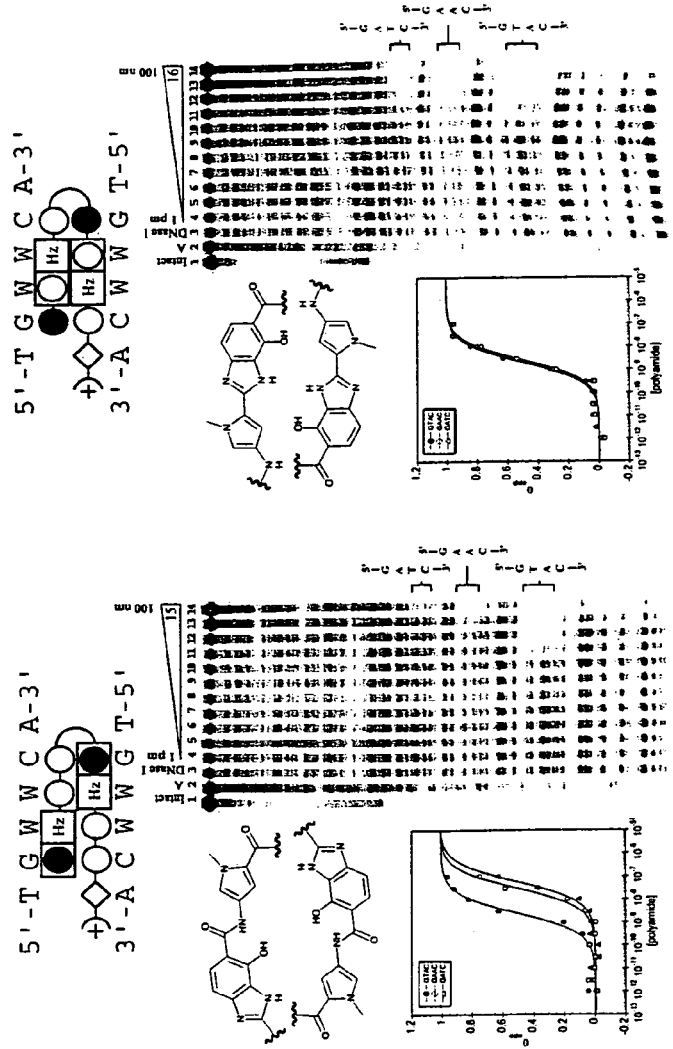

FIG. 14 illustrates a complete sequence of the EcoRI/PvuII restriction fragment derived from plasmids (a) pDHN1 (SEQ ID NO: 7) and (b) pDEH10 (SEQ ID NO: 8). For pDHN1, the four designed 6-base pair binding sites that were analyzed in quantitative DNaseI-footprinting titrations are shown with the variable Watson-Crick base pairs bolded and the binding site boxed. For pDEH10, the three designed 6-base pair binding sites that were analyzed in quantitative DNaseI-footprinting titrations are shown with the variable Watson-Crick base pairs bolded and the binding site boxed FIG. 15 is a table showing the association equilibrium constant $K_a[M^{-1}]$ for polyamide oligomers G and J. The reported association constants are the average values obtained from three DNase I footprint titration experiments, with the standard deviation given in parenthesis. Assays were carried out at 22° C. at pH 7.0 in the presence of 10 mM Tris-HCl, 10 mM KCl, 10 mM MgCl$_2$, and 5 mM CaCl$_2$ at pH 7.0.

FIG. 16 illustrates the quantitative DNase I footprinting experiments in the hairpin motif for polyamides oligomers G and J, respectively, on the 285 bp, 5'-end-labelled PCR product of plasmid DEH10: lane 1, intact DNA; lane 2, A reaction; lane 3, DNase I standard; lanes 4-14, 1 pM, 3 pM, 10 pM, 30 pM, 100 pM, 300 pM, 1 nM, 3 nM, 10 nM, 30 nM, 100 nM polyamide, respectively. Each footprinting gel is accompanied by the following: (left, top) Chemical structure of the pairing of interest; and (bottom left) Binding isotherms for the four designed sites. $\theta_{norm}$ values were obtained according to published methods. A binding model for the hairpin motif is shown centered at the top as a dot model with the polyamide bound to its target DNA sequence. Imidazoles and pyrroles are shown as filled and non-filled circles, respectively; Beta alanine is shown as a diamond; the gamma-aminobutyric acid turn residue is shown as a semicircle connecting the two subunits; the hydroxybenzimidazole residue is indicated by a square containing Hz.

FIG. 17 is a table showing the association equilibrium constant $K_a[M^{-1}]$ for polyamide oligomers H and K. The reported association constants are the average values obtained from three DNase I footprint titration experiments, with the standard deviation given in parenthesis. Assays were carried out at 22° C. at pH 7.0 in the presence of 10 mM Tris-HCl, 10 mM KCl, 10 mM MgCl$_2$, and 5 mM CaCl$_2$ at pH 7.0.

FIG. 18 illustrates quantitative DNase I footprinting experiments in the hairpin motif for polyamide oligomers H and K, respectively, on the 278 bp, 5'-end-labelled PCR product of plasmid DHN1: lane 1, intact DNA; lane 2, A reaction; lane 3, DNase I standard; lanes 4-14, 1 pM, 3 pM, 10 pM, 30 pM, 100 pM, 300 pM, 1 nM, 3 nM, 10 nM, 30 nM, 100 nM polyamide, respectively. Each footprinting gel is accompanied by the following: (left, top) Chemical structure of the pairing of interest; and (bottom left) Binding isotherms for the four designed sites. $\theta_{norm}$ values were obtained according to published methods. A binding model for the hairpin motif is shown centered at the top as a dot model with the polyamide bound to its target DNA sequence. Imidazoles and pyrroles are shown as filled and non-filled circles, respectively; Beta alanine is shown as a diamond; the gamma-aminobutyric acid turn residue is shown as a semicircle connecting the two subunits; the hydroxybenzimidazole residue is indicated by a square containing Hz; the benzimidazole residue is indicated by a square containing Bi.

FIG. 19 is a a table showing the association equilibrium constant $K_a[M^{-1}]$ for polyamide oligomers I and L. The reported association constants are the average values obtained from three DNase I footprint titration experiments, with the standard deviation given in parenthesis. Assays were carried out at 22° C. at pH 7.0 in the presence of 10 mM Tris-HCl, 10 mM KCl, 10 mM $MgCl_2$, and 5 mM $CaCl_2$ at pH 7.0.

DETAILED DESCRIPTION OF THE PREFERRED EMBODIMENTS

Presented herein are novel oligomers corresponding to Formulas (I) and (II), as presented in the Summary of the Invention. Kits comprising oligomers of the invention and compositions comprising oligomers of the invention and a pharmaceutically acceptable carrier are also presented. Oligomers of the invention may be used for detection or isolation of specific sequences in a sample of dsDNA. Furthermore, oligomers of the invention may be used to reduce transcription of a target gene, such as an oncogene, in a cell.

Within this application, unless otherwise stated, definitions of the terms and illustration of the techniques of this application may be found in any of several well-known references such as: Sambrook, J., et al., *Molecular Cloning: A Laboratory Manual*, Cold Spring Harbor Laboratory Press (2000); Goeddel, D., ed., Gene Expression Technology, *Methods in Enzymology*, 185, Academic Press, San Diego, Calif. (1991); "*Guide to Protein Purification*" in Deutshcer, M. P., ed., Methods in Enzymology, Academic Press, San Diego, Calif. (1990); Innis, et al., *PCR Protocols: A Guide to Methods and Applications*, Academic Press, San Diego, Calif. (1997); Freshney, R. I., *Culture of Animal Cells: A Multimedia Guide*, Fourth Edition, Alan Liss, Inc. New York, N.Y. (April 2000); Murray, E. J., ed., "*Gene Transfer and Expression Protocols*", pp. 109-128, The Human Press Inc., Clifton, N.J. and Lewin, B., Genes VI, Oxford University Press, New York (April 1991).

I. Oligomers of the Invention

Presented herein are novel oligomers comprising at least one monomer corresponding to Formula (I) as shown above in the Summary of the invention. Also presented are oligomers corresponding to Formula (II) as shown above in the Summary of the Invention. The invention oligomers of Formula (II) comprise two equal length chains of monomers, wherein either chain comprises at least one fused six-membered ring.

Preferred fused six-membered cyclic monomers include benzimidazole (Bi), imidazo[4,5-b]pyridine (Ip), and hydroxybenzimidazole (Hz), and their structures are shown below:

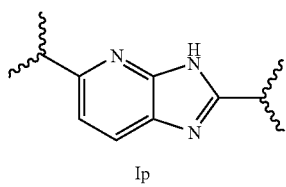
Ip

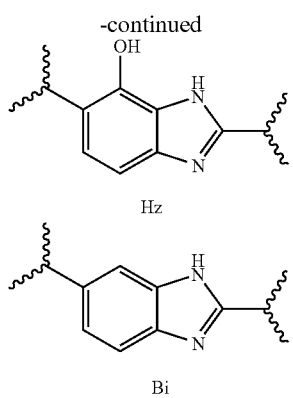
Hz

Bi

In certain embodiments, oligomers of the invention further comprise five-membered heterocyclic monomers. Representative five-membered heterocycles include N-methyl pyrrole (Py), 1-methyl-1H-pyrazole (Pz), 1H-pyrrole (Nh), N-methyl imidazole (Im), 5-methylthiazole (Nt), furan (Fr), 3-hydroxypyrrole (Hp), 3-hydroxythiopene (Ht), 4-methylthiazole (Th), 3-methylthiophene (Tn), and thiophene (Tp). Structures of these exemplary five-membered heterocycles have been presented herein above.

Each heterocyclic monomer can be attached to another monomer by a connectivity denoted as G, wherein G is independently

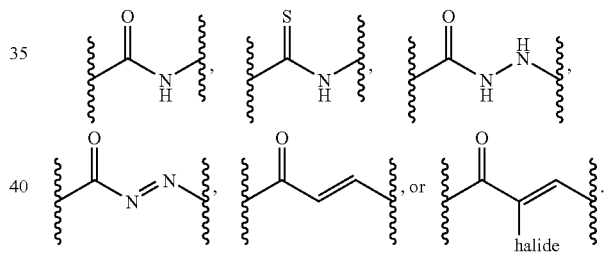

The connectivity between each heterocyclic monomer in the present oligomers may be the same or different throughout the oligomer. A preferable connectivity for oligomers of the invention is the amide bond, —C(=O)NH—, which gives rise to polyamide oligomers.

Chains of heterocyclic monomers are covalently linked together by a linker denoted as L and defined above. Representative linkers comprise 2 to 12 carbon atoms, such as —$CH_2CH_2CH_2$—. In some embodiments, linkers may impart an overall U-turn shape to the oligomer resulting in the formation of a hairpin oligomer. Hairpin turns facilitate binding to dsDNA by positioning both chains of the oligomer around the duplex DNA. Examples of linkers include aliphatic amino acids, such as beta-alanine (β), gamma-aminobutyric acid (γ), and diaminobutyric acid (DAB). Hairpin oligomers, particularly hairpin polyamide oligomers, are well known in the art and are described, for example, in Church et al., supra and He et al., supra. Structures of representative hairpin polyamide oligomers of the invention are shown below in Table 2.

TABLE 2
| Oligomer Name | Oligomer Sequence | Oligomer Structure |
| --- | --- | --- |
| A | Im-Py-Ip-Py-DAB-Py-Py-Py-Py | 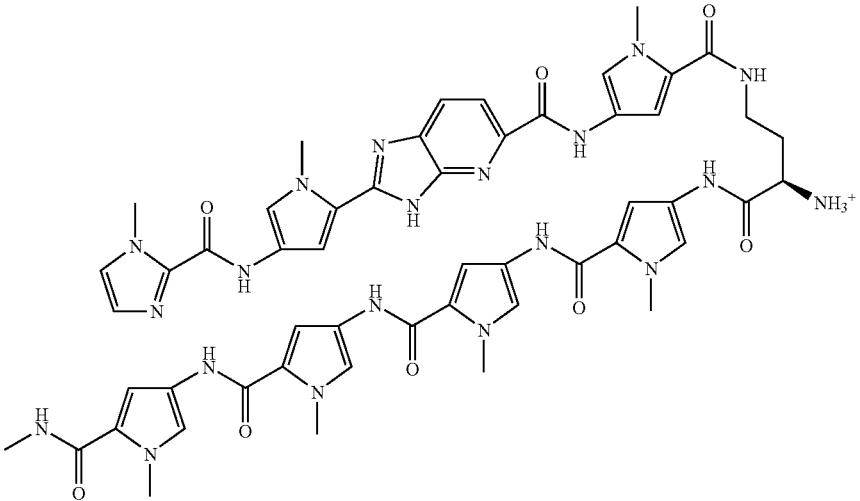 |
| B | Im-Py-Hz-Py-DAB-Py-Py-Py-Py | 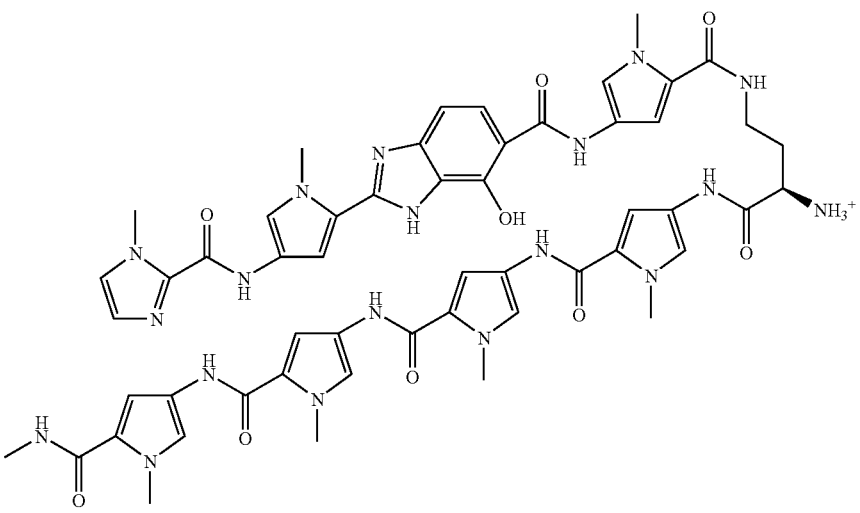 [SMILES: CNC(=O)c1cc(NC(=O)c2cc(NC(=O)c3cc(NC(=O)c4cc(NC(=O)[C@H]([NH3+])CCNC(=O)c5cc(NC(=O)c6ccc7nc(-c8cc(NC(=O)c9nccn9C)cn8C)[nH]c7c6O)cn5C)cn4C)cn3C)cn2C)cn1C] |
| C | Im-Py-Bi-Py-DAB-Py-Py-Py-Py | 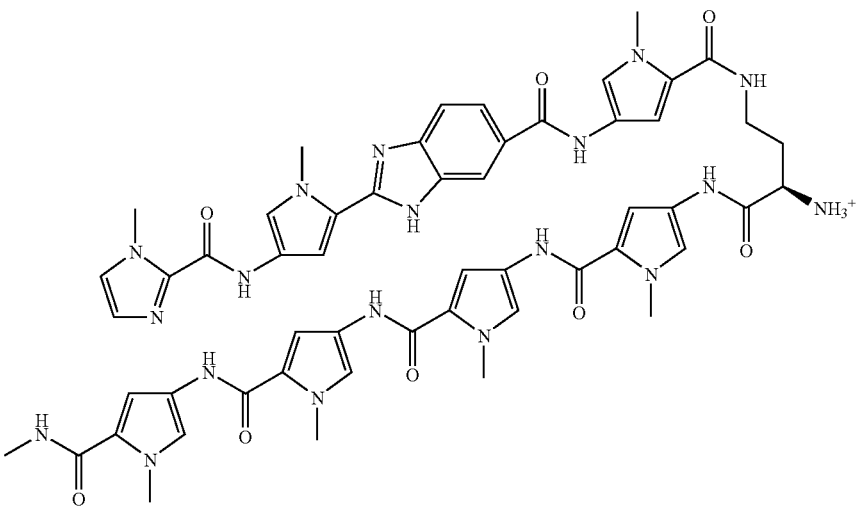 |

| Oligomer Name | Oligomer Sequence | Oligomer Structure |
|---|---|---|
| D | Im-Im-Py-Py-DAB-Im-Py-Bi-Py | 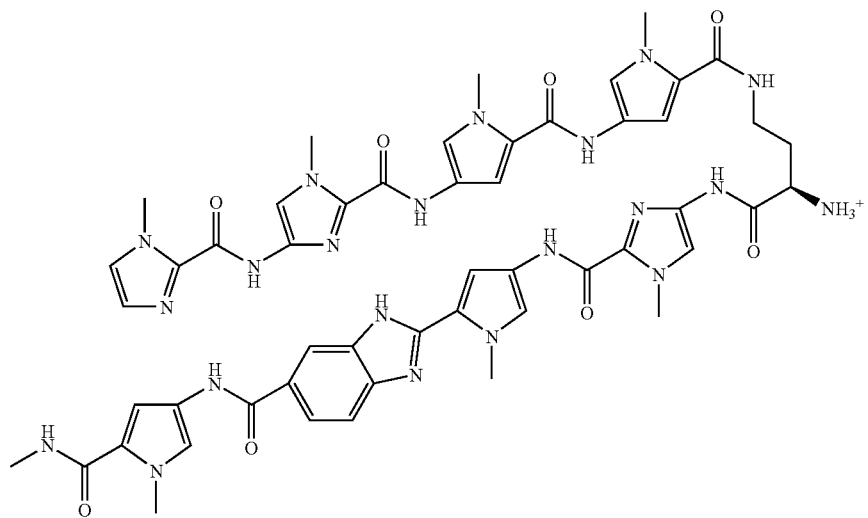 |
| E | Im-Im-Py-Py-DAB-Py-Im-Bi-Py | 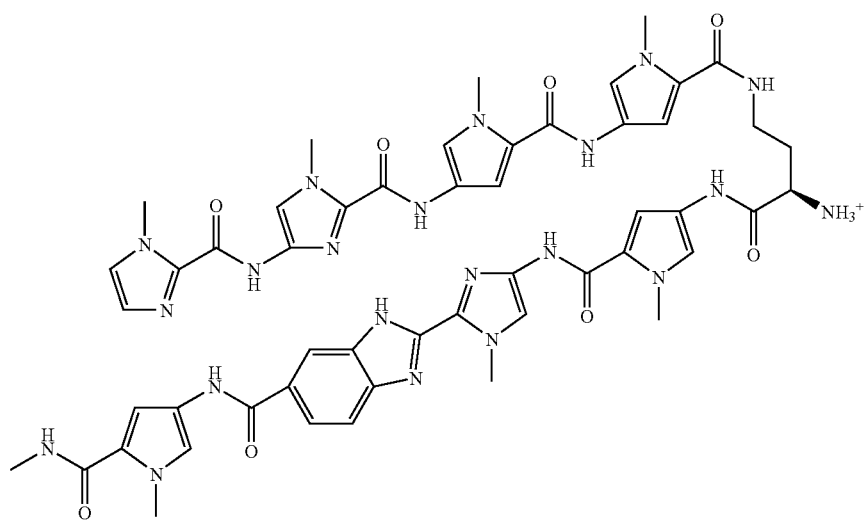 |

TABLE 2-continued
| Oligomer Name | Oligomer Sequence | Oligomer Structure |
|---|---|---|
| F | Im-Im-Py-Py-DAB-Im-Hp-Bi-Py | 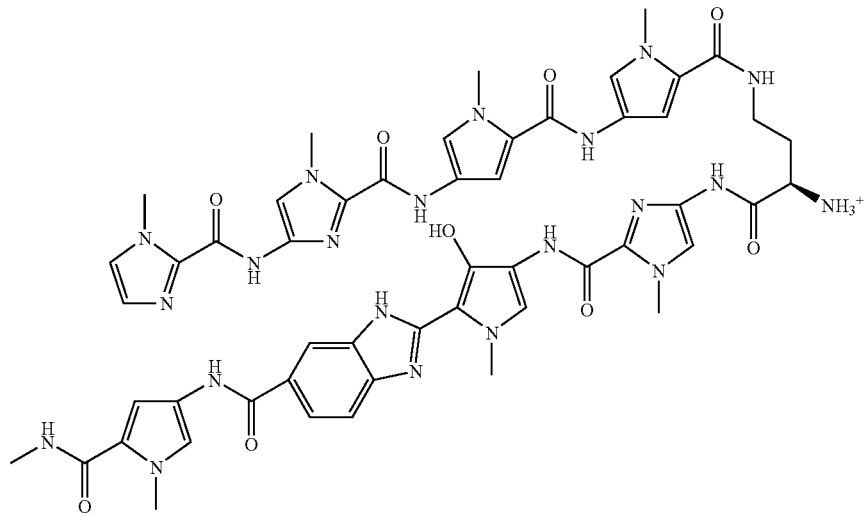 [SMILES: CNC(=O)c1cc(NC(=O)c2ccc3nc(-c4c(O)c(NC(=O)c5nc(NC(=O)[C@H]([NH3+])CCNC(=O)c6cc(NC(=O)c7cc(NC(=O)c8nc(NC(=O)c9nccn9C)cn8C)cn7C)cn6C)cn5C)cn4C)[nH]c3c2)cn1C] |
| G | Im-Im-Hz-Py-γ-Im-Py-Py-Py-β-Dp | 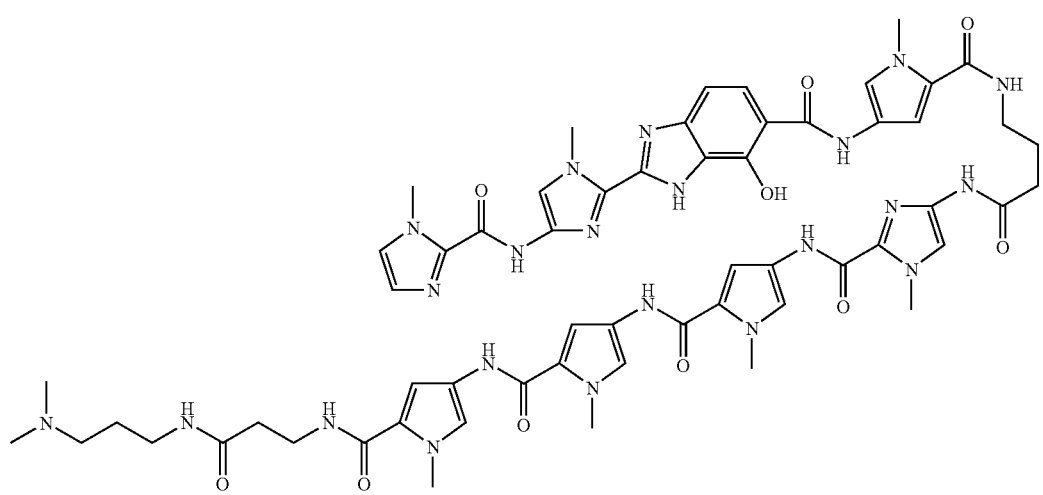 [SMILES: CN(C)CCCNC(=O)CCNC(=O)c1cc(NC(=O)c2cc(NC(=O)c3cc(NC(=O)c4nc(NC(=O)CCCNC(=O)c5cc(NC(=O)c6ccc7nc(-c8nc(NC(=O)c9nccn9C)cn8C)[nH]c7c6O)cn5C)cn4C)cn3C)cn2C)cn1C] |
| H | Im-Hz-Py-Py-γ-Im-Hz-Py-Py-β-Dp | 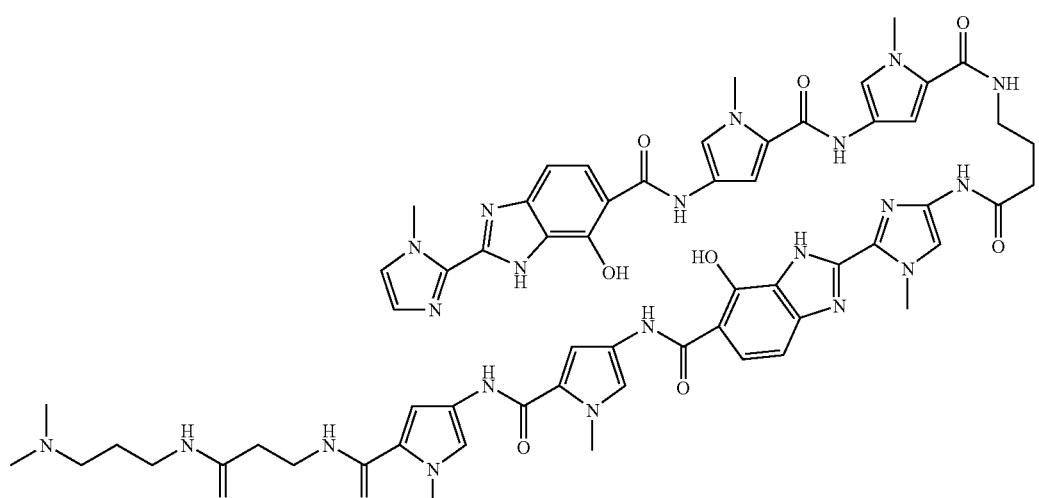 |

TABLE 2-continued

| Oligomer Name | Oligomer Sequence | Oligomer Structure |
|---|---|---|
| I | Im-Im-Hz-Py-γ-Im-Bi-Py-Py-β-Dp | |
| J | Im-Im-Py-Py-γ-Im-Hz-Py-Py-β-Dp | |
| K | Im-Py-Hz-Py-γ-Im-Py-Hz-Py-β-Dp | |

TABLE 2-continued

| Oligomer Name | Oligomer Sequence | Oligomer Structure |
|---|---|---|
| L | Im-Im-Bi-Py-γ-Im-Hz-Py-Py-β-Dp | 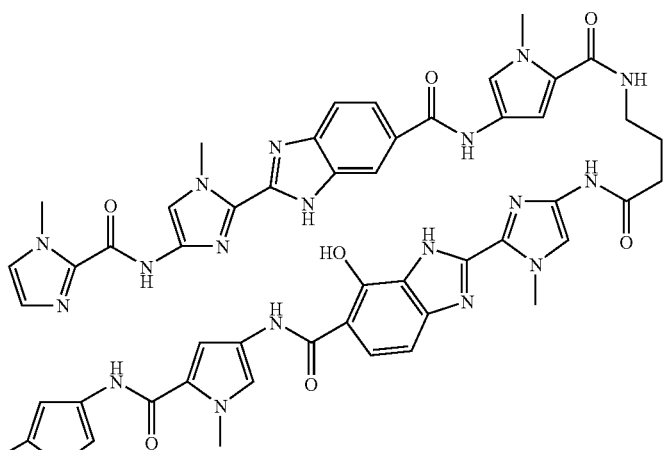 |

Preparation of Oligomers of the Invention

Methods for preparing monomers comprising fused six-membered heterocycles are well known to one of skill in the art, and can be accomplished by a variety of standard methods, as described in, for example, Renneberg et al., "Imidazopyridine/Pyrrole and Hydroxybenzimidazole/Pyrrole Pairs for DNA Minor Groove Recognition" *JACS*, Vol. 125-5707-5716, 2003 and Briehn et al., "Alternative Heterocycles for DNA Recognition: The Benzimidazole/Imidazole Pair," *Chem. Eur. J.*, Vol. 9: 2110-2112, 2003. Exemplary synthetic schemes for the preparation of representative fused six-membered heterocycles are illustrated below in the Examples.

Methods for preparing monomers comprising five-membered heterocycles as shown above are well known to one of skill in the art, and can be accomplished by a variety of standard methods, as described in, for example, Minehan et al., *Helvetica Chimica Acta*, Vol. 85: 4485-4517, 2002.

Oligomers of the present invention can be synthesized by a variety of well known synthetic methods, such as solid phase synthesis, as described in, for example, Renneberg et al., supra and Briehn et al., supra. Exemplary synthetic schemes for the preparation of representative oligomers of the invention are illustrated below in the Examples.

Oligomers of the invention can be purified by a sequence of chromatographic steps employing any or all of the following types: ion exchange on a weakly basic resin (acetate form); hydrophobic adsorption chromatography on underivitized polystyrene-divinylbenzene (for example, Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or octadecylsilyl-silica bonded phase column packing.

Oligomers of a desired length are removed from the resin and deprotected, either successively or in a single operation, using well known procedures. For instance, deprotection of amino protecting groups can be accomplished with acidic solutions, such as 20% trifluoroacetic acid (TFA) or 50% TFA in methylene chloride. Liberation of the oligomer may be accomplished by a variety of well known methods, such as treatment with a warm solvent solution (approximately 37° C.), such as tetrahydrofuran (THF) or methylamine in methylene chloride for 8-24 hrs. Oligomers may be used directly after cleavage from the resin or can be further purified using a variety of well known purification methods, such as reverse-phase HPLC. The identity and purity of the polyamides may be verified using any of a variety of analytical techniques available to one skilled in the art such as $^1$H-NMR, analytical HPLC, and/or matrix-assisted laser-desorption ionization time-of-flight mass spectrometry (MALDI-TOF MS-monoisotropic).

II. Specific Binding of DNA Pairs by Oligomers of the Invention

In an aspect of the invention, oligomers of the invention are capable of binding to dsDNA in a sequence specific manner. Presented herein are novel polyamide heterocyclic pairs which recognize specific nucleotide base pairs, wherein said heterocyclic pairs comprise at least one fused six-membered ring. Table 3 below lists the new pairing rules for novel polyamide pairs discovered herein.

TABLE 3

Specific DNA Recognition of Pairs Comprising Fused Six-Membered Rings

| Representative Six-Membered Pair | DNA Pair(s) Recognized |
|---|---|
| Ip/Py | G·C |
| Bi/Py | T·A |
|  | A·T |
| Hz/Py | T·A |
| Py/Hz | A·T |
| Hz/Bi | T·A |
| Bi/Hz | A·T |

Recognition of specific sequences on dsDNA by certain polyamide pairs comprising six-membered rings at subnanomolar concentrations are described in Renneberg et al., supra and Briehn et al., supra. Application of the novel polyamide pairs listed above in Table 3 can be used in conjunction with previously described polyamide five-membered heterocyclic pairs towards the construction of a wide array of versatile polyamide oligomers. Experimental data illustrating sequence specific recognition of representative oligomers of the invention is provided below in the Examples.

Oligomers of the invention provide for coded targeting of pre-determined DNA sequences with high affinity and specificity. By employing the binding pairs listed above, oligomers of the invention may be designed to bind to any target DNA sequence.

A. Detection and Isolation Methods Using Oligomers of the Invention

The formation of complexes between dsDNA and oligomers of the present invention may be used for diagnostic, therapeutic, purification, or research purposes, and the like. Oligomers of the present invention can be used to detect specific dsDNA sequences in a sample without melting the dsDNA. Examples of diagnostic applications for which oligomers of the present invention may be used include detection of alleles, identification of mutations, identification of a particular host, e.g. bacterial strain or virus, identification of the presence of a particular DNA rearrangement, identification of the presence of a particular gene, e.g. multiple resistance gene, forensic medicine, or the like. With pathogens, the pathogens may be viruses, bacteria, fungi, protista, chlamydia, or the like. With higher hosts, the hosts may be vertebrates or invertebrates, including insects, fish, birds, mammals, and the like or members of the plant kingdom.

Oligomers of the present invention are also useful for detecting the presence of dsDNA of a specific sequence for diagnostic or preparative purposes. The sample containing the dsDNA can be contacted by an oligomer linked to a solid substrate, thereby isolating DNA comprising a desired sequence. Alternatively, polyamides linked to a suitable detectable marker, such as biotin, a hapten, a radioisotope or a dye molecule, can be contacted by a sample containing double stranded DNA.

For instance, one may wish to have an isotopic oligomer which can be detected through various well known methods, such as via scintillation counters and nuclear magnetic resonance spectroscopy, and the like. A radioactive moiety may be employed as a detectable label, such tritium, $^{14}$C, $^{125}$I, or the like. The radiolabel may be a substituent on a carbon or a heteroatom of any atom in any monomer, or the radiolabel may be a substituent at either terminus of the oligomer. The radiolabel may serve numerous purposes in diagnostics, cytohistology, radiotherapy, and the like.

Other detectable labels include fluorescers, e.g. dansyl, fluorescein, Texas red, isosulfan blue, ethyl red, and malachite green, chemiluminescers, magnetic particles, colloidal particles, gold particles, light sensitive bond forming compounds, i.e. psoralens, anthranilic acid, pyrene, anthracene, and acridine, chelating compounds, such as EDTA, NTA, tartaric acid, ascorbic acid, polyhistidines of from 2 to 8 histidines, alkylene polyamines, etc., chelating antibiotics, such as bleomycin, where the chelating compounds may chelate a metal atom, such as iron, cobalt, nickel, technetium, etc., where the metal atom may serve to cleave DNA in the presence of a source of peroxide, intercalating dyes, such as ethidium bromide, thiazole orange, thiazole blue, TOTO, 4',6-diamidino-2-phenylindole (DAPI), etc., enzymes, such as β-galactosidase, NADH or NADHP dehydrogenase, malate dehydrogenase, lysozyme, peroxidase, luciferase, etc., alkylating agents such as haloacetamides, N-ethyl nitrosourea, nitrogen and sulfur mustards, sulfonate esters, etc., and other compounds, such as arylboronic acids, tocopherols, lipoic acid, captothesin, etc. colloidal particles, e.g., gold particles, fluorescent particles, peroxides, DNA cleaving agents, oligonucleotides, oligopeptides, NMR agents, stable free radicals, metal atoms, etc. The oligomer may be combined with other labels, such as haptens for which a convenient receptor exists, e.g. biotin, which may be complexed with avidin or streptavidin and digoxin, which may be complexed with antidigoxin, etc. where the receptor may be conjugated with a wide variety of labels, such as those described above. The oligomers may be joined to sulfonated or phosphonated aromatic groups, e.g. naphthalene, to enhance inhibition of transcription, particularly of viruses (Clanton et al., *Antiviral Res.*, 27:335-354, 1995). In some instances, one may bond multiple copies of the subject oligomers to polymers, where the subject oligomers are pendant from the polymer. Polymers, particularly water soluble polymers, which may find use are cellulose, poly(vinyl alcohol), poly(vinyl acetate-vinyl alcohol), polyacrylates, and the like.

For detecting the presence of a target sequence, the dsDNA may be extracellular or intracellular. When extracellular, the dsDNA may be in solution, in a gel, on a slide, or the like. The dsDNA may be present as part of a whole chromosome or fragment thereof of one or more centiMorgans. The dsDNA may be part of an episomal element. The dsDNA may be present as smaller fragments ranging from about 20, usually at least about 50, to a million base pairs, or more. The dsDNA may be intracellular, chromosomal, mitochondrial, plastid, kinetoplastid, or the like, part of a lysate, a chromosomal spread, fractionated in gel elecrophoresis, a plasmid, or the like, being an intact or fragmented moiety. When involved in vitro or ex vivo, the dsDNA may be combined with the subject compositions in appropriately buffered medium, generally at a concentration in the range of about 0.1 nM to 1 mM. Various buffers may be employed, such as TRIS, HEPES, phosphate, carbonate, or the like, the particular buffer not being critical to this invention. Generally, conventional concentrations of buffer will be employed, usually in the range of about 10-200 mM. Other additives which may be present in conventional amounts include sodium chloride, generally from about 1-250 mM, dithiothreitol, and the like, the particular nature or quantity of salt not being critical to this invention. The pH will generally be in the range of about 6.5 to 9, the particular pH not being critical to this invention. The temperature will generally be in a range of 4-45° C., the particular temperature not being critical to this invention. The target dsDNA may be present in from about 0.001 to 100 times the moles of oligomer.

The present invention also provides a diagnostic system, preferably in kit form, for assaying for the presence of the double stranded DNA sequence bound by oligomers of the invention in a body sample, such as brain tissue, cell suspensions or tissue sections, or body fluid samples such as colony stimulating factor (CSF), blood, plasma or serum, where it is desirable to detect the presence, and preferably the amount, of the double stranded DNA sequence bound by the polyamide in the sample according to the diagnostic methods described herein.

The diagnostic system includes, in an amount sufficient to perform at least one assay, a specific oligomer as a separately packaged reagent. Instructions for use of the packaged reagent(s) are also typically included. As used herein, the term "package" refers to a solid matrix or material such as glass, plastic (e.g., polyethylene, polypropylene or polycarbonate), paper, foil and the like capable of holding within fixed limits a polyamide of the present invention. Thus, for example, a package can be a glass vial used to contain milligram quantities of a contemplated polyamide or it can be a microliter plate well to which microgram quantities of a contemplated polyamide have been operatively affixed, i.e., linked so as to be capable of being bound by the target DNA sequence. "Instructions for use" typically include a tangible expression describing the reagent concentration or at least one assay method parameter such as the relative amounts of reagent and sample to be admixed, maintenance time periods for reagent or sample admixtures, temperature, buffer conditions and the like. A diagnostic system of the present invention preferably also includes a detectable label and a detecting or indicating means capable of signaling the binding of the contemplated polyamide of the present invention to the target DNA sequence. As noted above, numerous detectable labels, such as biotin, and detecting or indicating means, such as enzyme-linked (direct or indirect) streptavidin, are well known in the art.

Kits may optionally contain instructions for administering oligomers or compositions of the present invention to a subject having a condition in need of treatment. Kits may also comprise instructions for approved uses of oligomers of the invention by regulatory agencies, such as the United States Food and Drug Administration. Kits may optionally contain labeling or product inserts for oligomers of the invention. The package(s) and/or any product insert(s) may themselves be approved by regulatory agencies. The kits can include oligomers of the invention in the solid phase or in a liquid phase (such as buffers provided) in a package. The kits also can include buffers for preparing solutions for conducting the methods, and pipettes for transferring liquids from one container to another.

B. Representative Target Sequences on dsDNA

In an aspect of the invention, oligomers bind dsDNA in a sequence specific manner at any pre-determined target sequence. Target sequences can include coding and noncoding DNA sequences. For instance, target sequences can include transcriptional regulatory sequences, such as promoter regions and enhancer regions.

A representative regulatory sequence is 5'-TATAAA-3' also called the "TATA box", which when positioned on the coding strand of DNA approximately 30 base pairs upstream of the transcription start site, forms part of the promoter region (Lewin, Genes VI, pp. 831-835).

An exemplary target sequence for binding with oligomers of the invention is a promoter region. As used herein, the term "promoter" refers to a regulatory sequence of DNA that is involved in the binding of RNA polymerase to initiated transcription of a gene. A gene is a segment of DNA involved in producing a peptide, polypeptide or protein, including the coding region, non-coding regions preceding ("leader") and following ("trailer") the coding region, as well as intervening non-coding sequences ("introns") between individual coding segments ("exons"). Coding refers to the representation of amino acids, start and stop signals in a three base "triplet" code. Promoters are often upstream (5' to) the transcription initiation site of the corresponding gene. Other regulatory sequences of DNA in addition to promoters are known, including sequences involved with the binding of transcription factors, including response elements that are the DNA sequences bound by inducible factors. Enhancers comprise yet another group of regulatory sequences of DNA that can increase the utilization of promoters, and can function in either orientation (5'-3' or 3'-5') and in any location (upstream or downstream) relative to the promoter. Preferably, the regulatory sequence has a positive activity, i.e., binding of an endogenous ligand (e.g. a transcription factor) to the regulatory sequence increases transcription, thereby resulting in increased expression of the corresponding target gene. In such a case, interference with transcription by binding oligomers of the present invention to a regulatory sequence would reduce or abolish expression of a gene.

The promoter may also include or be adjacent to a regulatory sequence known in the art as a silencer. A silencer sequence generally has a negative regulatory effect on expression of the gene. In such a case, expression of a gene may be increased directly by using an oligomer of the invention to prevent binding of a factor to a silencer regulatory sequence or indirectly, by using a polyamide to block transcription of a factor to a silencer regulatory sequence.

While not being bound to any hypothesis, it is believed that the binding of oligomers of the invention modulate gene expression by altering the binding of DNA binding proteins, such as RNA polymerase, transcription factors, TBF, TFIIIB and other proteins. The effect on gene expression of polyamide binding to a segment of double stranded DNA is believed to be related to the function, e.g., promoter, of that segment of DNA.

Oligomers of the present invention may bind to any of the above-described DNA sequences or any other sequence having a desired effect upon expression of a gene. In addition, U.S. Pat. No. 5,578,444 describes numerous promoter targeting sequences from which base pair sequences for targeting an oligomer of the present invention may be identified.

Oligomers of the invention may bind to target sequences located in the minor groove of dsDNA. It is generally understood by those skilled in the art that the basic structure of DNA in a living cell includes both major and minor grooves. For the purposes of describing the present invention, the minor groove is the narrow groove of DNA as illustrated in common molecular biology reference such as Lewin, B., Genes VI, Oxford University Press, New York (1997).

To modulate gene expression in a cell, which may include causing an increase or a decrease in gene expression, an effective amount of one or more oligomer of the invention is contacted with the cell and internalized by the cell. The cell may be contacted in vivo or in vitro. Effective extracellular concentrations of polyamide oligomers that can modulate gene expression range from about 10 nanomolar to about 1 micromolar (Gottesfeld, J. M., et al., "Regulation of gene expression by small molecules," *Nature* 387:202-205 (1997)). One exemplary method to determine effective amounts and concentrations of oligomers in vitro is to place a suitable number of cells on tissue culture plates and add various quantities of one or more oligomers to separate wells. Gene expression following exposure to an oligomer can be monitored in the cells or medium by detecting the amount of the protein gene product present as determined by various techniques utilizing specific antibodies, including ELISA and Western blot. Alternatively, gene expression following exposure to an oligomer can be monitored by detecting the amount of mRNA present as determined by various techniques, including northern blot and RT-PCR.

An exemplary method to determine effective amounts and concentrations of oligomers for in vivo administration involves obtaining a sample of body tissue or fluid, such as plasma, blood, urine, cerebrospinal fluid, saliva, or biopsy of skin, muscle, liver, brain or other appropriate samples to analyze. Gene expression following exposure to an oligomer of the invention can be monitored by detecting the amount of the protein gene product present as determined by various techniques utilizing specific antibodies, including ELISA and western blot. Alternatively, gene expression following exposure to an oligomer can be monitored by the detecting the amount of mRNA present as determined by various techniques, including northern blot and RT-PCR.

C. Modulation of Expression of Target Genes

In an aspect of the invention, oligomers of the invention may be used to modulate the expression of a variety of target genes. Target genes include any gene which is implicated in the manifestation or propagation of a disease state. For instance, expression of viral genes may be inhibited using oligomers of the invention. Exemplary viral genes include HIV, HTLV, HPV, and HSV related genes.

Oligomers of the invention may also be used to decrease the expression of an oncogene. Aberrant expression of various oncogenes has been implicated in the manifestation of abnormal cellular proliferation. Representative oncogenes wherein expression may be modulated by oligomers of the invention include v-sis, int 2, KS3, HST, int-1, EGFR, v-fms, v-kit, v-ros, MET, TRK, NEU, RET, sea, Db1, Ost, Tiam-1, Vav, Lbc, H-RAS, K-RAS, N-RAS, gsp, gip, v-crk, SRC, v-yes, v-fgr, v-fps, v-fes, BCR/ABL, ros, v-mos, v-raf, pim-1, cot (ser/thr), v-myc, N-MYC, L-MYC, v-myb, v-fos, v-jun, v-ski, v-rel, v-ets, and v-erbA. Accordingly, oligomers of the instant invention may be administered to a subject for the treatment or amelioration of cancer. "Treating" as used herein refers to alleviation of at least one symptom associated with cancer, or halt of further progression or worsening of such symptom, or prevention or prophylaxis of cancer.

III. Therapeutic Delivery

A. Delivery Modes

The particular delivery mode selected will depend upon the particular oligomer selected, the condition being treated, the severity of the condition, whether the treatment is therapeutic or prophylactic, and the dosage required for efficacy. Therapeutic delivery of oligomers of the invention may be practiced using any mode of administration that is medically acceptable, meaning any mode that produces effective levels of the active compounds without causing clinically unacceptable adverse effects. Any dosage forms containing effective amounts are well within the bounds of routine experimentation and therefore, well within the scope of the instant invention. A therapeutically effective dose may vary depending upon the route of administration and dosage form. The administration may, for example, be oral, intraperitoneal, intra-cavity such as rectal or vaginal, transdermal, topical, nasal, inhalation, mucosal, interdermal, or parenteral routes. The term "parenteral" includes subcutaneous, intravenous, intramuscular, or infusion. Intravenous or intramuscular routes may not be particularly suitable for long term therapy and prophylaxis. In certain embodiments, however, it may be appropriate to administer the agent in a continuous infusion every several days, or once a week, or every several weeks, or once a month. Intravenous or intramuscular routes may be preferred in emergency situations. Oral administration may be used for prophylactic treatment because of the convenience to the patient as well as the dosing schedule. Likewise, sustained release devices as described herein may be useful in certain embodiments for prophylactic or post surgery treatment, for example.

Direct administration of oligomers of the present invention to a designated site may be preferred for some methods provided herein. For example, treatment with the oligomer via topical administration in and around affected areas may be performed. In still other embodiments, oligomers may be delivered by injection directly into the tissue with, for example, a biopsy needle and syringe.

Systemic administration may be preferred in some instances such as, for example, if the subject is known to have or is suspected of having metastases. In this way, all tumor sites, whether primary or secondary may receive the oligomer. Systemic delivery may be accomplished through for example, oral or parenteral administration. Inhalation may be used in either systemic or local delivery, as described below.

B. Representative Dosing Regimens

The oligomers of the invention are administered in therapeutically effective amounts. A therapeutically effective amount is an amount sufficient to delay the onset of, inhibit the progression of, or halt altogether the particular condition being treated. The effective amount will vary with the particular condition being treated, the age and physical condition of the subject being treated, the severity of the condition, the duration of the treatment, the nature of the concurrent or combination therapy (if any), the specific route of administration and like factors within the knowledge and expertise of the health practitioner. A therapeutically effective dose results in amelioration of at least one undesirable symptom. It is preferred generally that a maximum dose be used, that is, the highest safe dose according to sound medical judgment. Dosing amounts, dosing schedules, routes of administration and the like can be selected so as to affect bio-activity of the present compounds. Such determinations are routine and well known to one of ordinary skill in the art.

A therapeutically effective amount typically varies from 0.01 mg/kg to about 1000 mg/kg, preferably from about 0.1 mg/kg to about 200 mg/kg, and most preferably from about 0.2 mg/kg to about 20 mg/kg, in one or more dose administrations daily, for one or more days. In some embodiments, the oligomers are administered for more than 7 days, more than 10 days, more than 14 days and more than 20 days. In still other embodiments, the agent is administered over a period of weeks, or months. In still other embodiments, the agent is delivered on alternate days. For example, the agent is delivered every two days, or every three days, or every four days, or every five days, or every six days, or every week, or every month.

Oligomers of the invention can also be administered in prophylactically effective amounts. In these instances, the oligomers are administered in an amount effective to prevent the development of an abnormal or undesirable condition or disease. For example, in connection with methods directed towards treating subjects having a condition characterized by abnormal mammalian cell proliferation, an effective amount to inhibit proliferation would be an amount sufficient to reduce or halt altogether the abnormal mammalian cell proliferation so as to slow or halt the development of or the progression of a cell mass such as, for example, a tumor. As used in the embodiments, "inhibit" embraces all of the foregoing.

For example, in connection with methods directed to inhibition of mammalian cell proliferation, a therapeutically effective amount will be an amount necessary to extend the dormancy of micrometastases or to stabilize any residual primary tumor cells following surgical or drug therapy.

C. Pharmaceutically Acceptable Carriers

Compositions presented herein may include oligomers of the invention in combination with any standard physiologically and/or pharmaceutically acceptable carrier known in the art. The term "pharmaceutically acceptable carrier" as used herein means one or more compatible solid or liquid fillers, diluents or encapsulating substances which are suitable for administration to a subject. The term "carrier" denotes an organic or inorganic ingredient, natural or synthetic, which with the oligomer is combined to facilitate delivery of the composition. The components of the pharmaceutical compositions also are capable of being co-mingled with the molecules of the present invention, and with each other, in a manner so as to not substantially impair the desired pharmaceutical efficacy. Pharmaceutically acceptable further means a non-toxic material that is compatible with a biological system such as a cell, cell culture, tissue, or organism. The particular carrier may vary depending on the route of therapeutic delivery.

Pharmaceutical compositions of the instant invention can be manufactured by methods well known in the art such as conventional granulating, mixing, dissolving, encapsulating, lyophilizing, emulsifying or levigating processes, among others. The compositions can be in the form of, for example, granules, powders, tablets, capsules, syrup, suppositories, injections, emulsions, elixirs, suspensions or solutions. The instant compositions can be formulated for various routes of administration, for example, by oral administration, by intranasal administration, by transmucosal administration, by rectal administration, or subcutaneous administration as well as intrathecal, intravenous, intramuscular, intraperitoneal, intranasal, intraocular or intraventricular injection. The compound or oligomers of the instant invention can also be administered in a local rather than a systemic fashion, such as injection as a sustained release formulation. The following dosage forms are given by way of example and should not be construed as limiting the instant invention.

Compositions suitable for parenteral administration conveniently comprise a sterile aqueous preparation of the agent, which is preferably isotonic with the blood of the recipient. This aqueous preparation may be formulated according to known methods using suitable dispersing or wetting compounds and suspending compounds. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. Administrations can be found, for example, in "Remington's Pharmaceutical Sciences" Mack Publishing Co., New Jersey (1991), which is incorporated herein by reference.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating compounds, and inert gases and the like. The pharmaceutical compositions may conveniently be presented in unit dosage form and may be prepared by any of the methods well-known in the art of pharmacy.

Compositions suitable for oral administration may be presented as discrete units, such as capsules, tablets, lozenges, each containing a predetermined amount of the agent. Other compositions include suspensions in aqueous liquids or non-aqueous liquids such as a syrup, elixir or an emulsion. Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

Compositions may comprise a biocompatible microparticle or implant that is suitable for implantation. Biocompatible and biodegradable polymeric matrix materials may also be added. The polymeric matrix may be used to achieve sustained release of the agent in a subject. Oligomers of the invention may be encapsulated or dispersed within a biocompatible and biodegradable polymeric matrix. The polymeric matrix can be in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular or pulmonary surface. The matrix composition also can be selected not to degrade, but rather, to release by diffusion over an extended period of time.

Both non-biodegradable and biodegradable polymeric matrices can be used to deliver the agents of the invention to the subject. Such polymers may be natural or synthetic polymers. Synthetic polymers are preferred. The polymer is selected based on the period of time over which release is desired, generally in the order of a few hours to a year or longer. The polymer optionally is in the form of a hydrogel that can absorb up to about 90% of its weight in water and further, optionally is cross-linked with multi-valent ions or other polymers.

Exemplary synthetic polymers which can be used include: polyamides, polycarbonates, polyalkylenes, polyalkylene glycols, polyalkylene oxides, polyalkylene terpthalates, polyvinyl alcohols, polyvinyl ethers, polyvinyl esters, polyvinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly (methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers may also be included in the present compositions. Examples of such bioadhesive polymers include polyhyaluronic acids, casein, gelatin, glutin, polyanhydrides, polyacrylic acid, alginate, chitosan, poly(methyl methacrylates), poly(ethyl methacrylates), poly(butyl-methacrylate), poly(isobutyl methacrylate), poly(hexyl-methacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Compositions of the present invention may be formulated as timed release, delayed release, or sustained release delivery systems. Such systems can avoid the need for repeated administrations of the agent of the invention, increasing convenience to the subject and the physician. Many types of release delivery systems are available and known to those of ordinary skill in the art. They include the above-described polymeric systems, as well as polymer base systems such as poly(lactide-glycolide), polyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the agent is contained in a form within a matrix such as those described in U.S. Pat. Nos. 4,452,775, 4,675,189 and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be used in the treatment of chronic conditions, such as the suspected presence of dormant metastases. Long-term release, are used herein, means that the implant is constructed and arranged to deliver therapeutic levels of the active ingredient for at least 30 days, at least 60 days and more preferably for several months. Long-term sustained release implants are well-known to those of ordinary skill in the art and include some of the release systems described above.

For oral, buccal, and sublingual administration, powders, suspensions, granules, tablets, pills, capsules, gelcaps, and caplets are acceptable as solid dosage forms. These can be prepared, for example, by mixing one or more oligomers of the instant invention, or pharmaceutically acceptable salts or tautomers thereof, with at least one additive or excipient such as a starch or other additive. Suitable additives or excipients are sucrose, lactose, cellulose, sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents, or perfuming agents. Additionally, dyestuffs or pigments may be added for identification. Tablets and pills may be further treated with suitable coating materials known in the art.

As noted above, suspensions may include oils. Such oils include, but are not limited to, peanut oil, sesame oil, cottonseed oil, corn oil and olive oil. Suspension preparations may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

For intranasal administration (e.g., to deliver compounds to the brain), or administration by inhalation (e.g., to deliver compounds through the lungs), the pharmaceutical formulations may be a solution, a spray, a dry powder, or aerosol containing any appropriate solvents and optionally other compounds such as, but not limited to, stabilizers, antimicrobial agents, antioxidants, pH modifiers, surfactants, bioavailability modifiers and combinations of these. Examples of intranasal formulations and methods of administration can be found in WO 01/41782, WO 00133813, WO 91/97947, U.S. Pat. Nos. 6,180,603, and 5,624,898. A propellant for an aerosol formulation may include compressed air, nitrogen, carbon dioxide, or a hydrocarbon based low boiling solvent. The compound or oligomers of the instant invention are conveniently delivered in the form of an aerosol spray presentation from a nebulizer or the like.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or diluents include sterilized water, Ringer's solution, or an isotonic aqueous saline solution.

For injection, the pharmaceutical formulation may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

For rectal administration, the pharmaceutical formulations may be in the form of a suppository, an ointment, an enema, a tablet or a cream for release of compound in the intestines, sigmoid flexure and/or rectum. Rectal suppositories are prepared by mixing one or more oligomers of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

D. Representative Pharmaceutically Acceptable Salts

Compositions of the present invention embrace pharmaceutically acceptable salts of oligomers of the invention. Pharmaceutically acceptable salts include a salt with an inorganic base, organic base, inorganic acid, organic acid, or basic or acidic amino acid. As salts of inorganic bases, the invention includes, for example, salts of alkali metals (such as sodium or potassium) and alkaline earth metals (such as calcium and magnesium or aluminum, and ammonia). As salts of organic bases, the invention includes, for example, salts of trimethylamine, triethylamine, pyridine, picoline, ethanolamine, diethanolamine, triethanolamine. As salts of inorganic acids, the instant invention includes, for example, salts of hydrochloric acid, hydroboric acid, nitric acid, sulfuric acid, and phosphoric acid. As salts of organic acids, the instant invention includes, for example, salts of formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid.

The following examples are provided to further illustrate aspects of the invention. These examples are non-limiting and should not be construed as limiting any aspect of the invention.

EXAMPLES $^1$H NMR and $^{13}$C NMR spectra were recorded on a Varian Mercury 300 and 500 instrument. Chemical shift values were recorded as parts per million relative to solvent and coupling constants in hertz. All NMR spectra were measured at room temperature (unless otherwise stated). UV spectra were measured on a Beckman Coulter DU 7400 diode array spectrophotometer. Mass spectra were recorded on the following mass spectrometer: matrix-assisted, laser desorption/ionization time-of-flight (MALDI-TOF) on Voyager DE-PRO from Applied Biosystems, fast atom bombardment (FAB) on a JEOL JMS-600H double focusing high-resolution magnetic sector, and electrospray injection (ESI) LCQ ion trap on a LCQ classic, Thermofinnigan and were carried out at the Protein and Peptide Microanalytical Facility at the California Institute of Technology. Precoated plates silica gel 60F$_{254}$ (Merck) were used for TLC and silica gel 60 (40 μm) for flash chromatography. Visualization was realized by UV and/or by using a solution of Ce(SO$_4$)$_2$, phosphomolybdic acid, H$_2$SO$_4$, and H$_2$O. HPLC analysis was performed on a Beckman Gold system using a Varian C$_{18}$, Microsorb-MV 100-5, 250×4.6 mm reversed-phase column in 0.1% (w/v) TFA with acetonitrile as eluent and a flow rate of 1.0 mL/min, gradient elution 1.25% acetonitrile/min. Preparatory HPLC was carried out on a Beckman HPLC using a Waters DeltaPak 100×25 mm, 100 μm C$_{18}$ column, 0.1% (w/v) TFA, 0.25% acetonitrile/min. 18 MΩ water was obtained from a Millipore MilliQ water purification system, and all buffers were 0.2 μm filtered. DNA oligonucleotides were synthesized by the Biopolymer Synthesis Center at the California Institute of Technology and used without further purification. Plasmids were sequenced by the Sequence/Structure Analysis Facility (SAF) at the California Institute of Technology. DNA manipulations were performed according to standard protocols. Autoradiography was performed with a Molecular Dynamics Typhoon Phosphorimager. Reactions were carried out under Arin anhydrous solvents. N,N'-Dicyclohexyl-carbodiimide (DCC), N-hydroxybenzotriazole (HOBt), and 2-(1H-benzotriazole-1-yl)-1,1,3,3-tetramethyluronium hexafluorophosphate (HBTU) were purchased from Peptides International. Oxime resin was purchased from Novabiochem (0.48 mmol/g). (R)-2-Fmoc-4-Boc-diaminobutyric acid (α-Fmoc-γ-Boc-(R)-DABA) was from Bachem, dichloromethane (DCM) was reagent grade from EM, and trifluoroacetic acid (TFA) was from Halocarbon. Bis(triphenylphosphine)palladium-(II) dichloride was from Fluka, all other reagents were from Aldrich (highest quality available). All enzymes (unless otherwise stated) were purchased from Roche Diagnostics and used with their supplied buffers. pUC19 was from New England Biolabs. [α-$^{32}$P]-Deoxyadenosine triphosphate and [α-$^{32}$P]-thymine triphosphate was purchased from New England Nucleotides. RNase-free water (used for all DNA manipulations) was from US Biochemicals. Ethanol (200 proof) was from Equistar, 2-propanol from Mallinckrodt. Premixed tris-borate-EDTA (Gel-Mate, used for gel running buffer) was from Gibco. Bromophenol blue and xylene cyanol FF were from Acros. 3-Methoxy-1-methyl-4-nitro-1H-pyrrole-2-carboxylic acid was synthesized as reported earlier (Briehn, C. A.; Weyermann, P.; Dervan, P. B. *Eur. J. Chem.*, in press).

N,N'-Dicyclohexylcarbodiimide (DCC), N-hydroxybenzotriazole (HOBt), and 2-(1H-benzotriazole-1-yl)-1,1,3,3-tetramethyluronium hexafluorophosphate (HBTU) were purchased from Peptides International. Oxime resin was purchased from Novabiochem (0.48 mmol g$^{-1}$, batch no. A18763). N,N-Diisopropylethylamine (DIEA) and N,N-dimethylformamide (DMF) were purchased from Applied Biosystems. (R)-2-Fmoc-4-Boc-diaminobutyric acid (α-Fmoc-γ-Boc-(R)-DABA) was from Bach-em, methyl 3,4-diaminobenzoate (19) from Avocado, dichloromethane (DCM) was reagent grade from EM, and trifluoroacetic acid (TFA) was from Halocarbon. All other chemicals were obtained reagent-grade from Aldrich (unless otherwise stated) and used without further purification. $^1$H NMR and $^{13}$C NMR spectra were recorded on a Varian Mercury 300 instrument. Chemical shifts are reported in ppm with reference to the solvent residual signal. UV spectra were measured on a Beckman Coulter DU 7400 diode array spectrophotometer. Matrix-assisted, laser desorption/ionization time-of-flight mass spectrometry (MALDI-TOF-MS), electro-spray injection (ESI-MS) and high resolution mass spectrometry (FAB, EI) was carried out at the California Institute of Technology. HPLC analysis was performed on a Beckman Gold system using a RAININ C18, Microsorb MV, 5 µm, 300×4.6 mm reversed-phase column in 0.1% (w/v) TFA with acetonitrile as eluent and a flow rate of 1.0 mL min$^{-1}$, gradient elution 1.25% acetonitrile min$^{-1}$. Preparatory HPLC was carried out on a Beckman HPLC using a Waters DeltaPak 100×25 mm, 100 µm C$_{18}$ column, 0.1% (w/v) TFA, 0.25% acetonitrile min$^{-1}$. 18 MΩ water was obtained from a Millipore MilliQ water purification system, and all buffers were 0.2 mm filtered. DNA oligonucleotides were synthesized by the Biopolymer Synthesis Center at the California Institute of Technology and used without further purification. Plasmids were sequenced by the Sequence/Structure Analysis Facility (SAF) at the California Institute of Technology. dNTPs (PCR nucleotide mix) and all enzymes (unless otherwise stated) were purchased from Roche Diagnostics and used with their supplied buffers. pUC19 was from New England Biolabs. [α-$^{32}$P]-Deoxyadenosine triphosphate and [α-$^{32}$P]-thymine triphosphate was from New England Nucleotides. RNase-free water (used for all DNA manipulations) was from US Biochemicals. Ethanol (100%) was from Equistar, isopropanol from Mallinckrodt. Bromophenol blue and xylene cyanol FF were from Acros. DNA manipulations were performed according to standard protocols. Autoradiography was performed with a Molecular Dynamics Typhoon Phosphorimager. 1-Methyl-4-nitro-1H-imidazole-2-carboxylic acid (18a) (E. E. Baird, P. B. Dervan, *J. Am. Chem. Soc.*, 118: 6141-6146, 1996) 1-methyl-4-nitro-1H-pyrrole-2-carbaldehyde (18c) (Y. Yamamoto, T. Kimachi, Y. Kanaoka, S. Kato, K. Bessho, T. Matsumoto, T. Kusakabe, Y. Sugiura, *Tetrahedron Lett.*, 37: 7801-7804, 1996), 3-methoxy-1-methyl-4-nitro-1H-pyrrole-2-carboxylic acid ethyl ester were synthesized according to literature procedures.

Example 1

Synthesis of Representative Fused Six-Membered Heterocyclic Monomers

A. Preparation of Imidazo[4,5-6]pyridine-Pyrrole

For the synthesis of the N-Boc-protected imidazo[4,5-b] pyridine-pyrrole building block (Boc-PyIp-OH, 9) commercially available 2,6-dichloro-3-nitropyridine (1) was used as starting material (Scheme 1). Nitropyridine 1 was converted to 6-bromo-3-nitropyridin-2-ylamine (2) via halogen exchange in both ortho-positions with HBr in acetic acid followed by treatment with NH$_3$/MeOH to regioselectively substitute one of the two bromo substituents. The introduction of the methyl ester functionality was then accomplished via a palladium-catalyzed carbonylation. In the presence of carbon monoxide, MeOH, Et$_3$N, and catalytic amounts of Pd(OAc)$_2$ and PPh$_3$, the conversion of 2 proceeded smoothly and methyl ester 3 was isolated in 61% yield. Systematic variation of the reaction conditions, e.g., CO pressure, temperature and catalytic system (PdCl$_2$(PPh$_3$)$_3$; Pd(OAc)$_2$, Dppp) did not show any effect on reaction time or yield. Reduction of the nitro group in 3 with Pd/C in the presence of hydrogen resulted in the corresponding ortho-diamine 10 in 63% yield.

The key step for the synthesis of the imidazo[4,5-b]pyridine-pyrrole unit was a cyclocondensation. The first step, a HBTU mediated coupling of diamine 4 with carboxylic acid 5 resulted in a mixture of the two isomeric amino amides 6a and 6b which were then transformed to the desired imidazo-[4,5-b]pyridine 7 by heating at 80-90° C. in glacial acetic acid. Note that similar cyclocondensation steps of amino amides usually require higher temperatures of 120-140° C. However, compounds 6a and 6b were unstable under these conditions, and no cyclization product was isolated. Due to purification problems with 7, crude product was used directly in the next step. Thus, after evaporation of the glacial acetic acid, reduction of the nitro group in 7 with tin(II)chloride in DMF and in situ Boc protection yielded in the aromatic amino acid ester 8. Final saponification of methyl ester 8 with sodium hydroxide in dioxane/H$_2$O afforded the desired N-Boc-protected imidazo[4,5-b]pyridine-pyrrole amino acid (Boc-PyIp-OH, 9) in 81% yield.

Scheme 1.
Synthesis of Boc-protected Imidazo [4,5–6] Pyridine Amino Acid

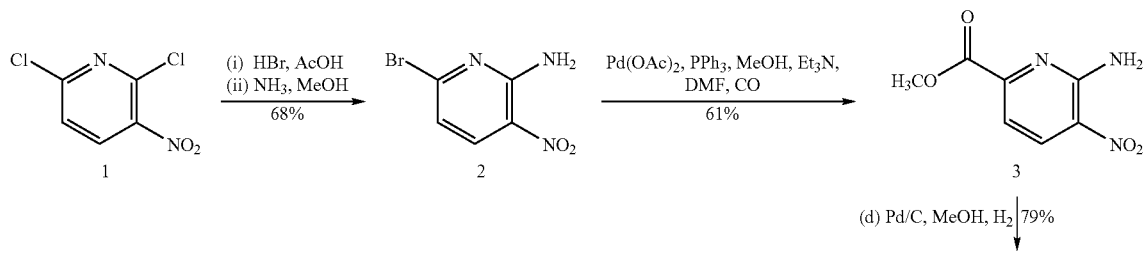

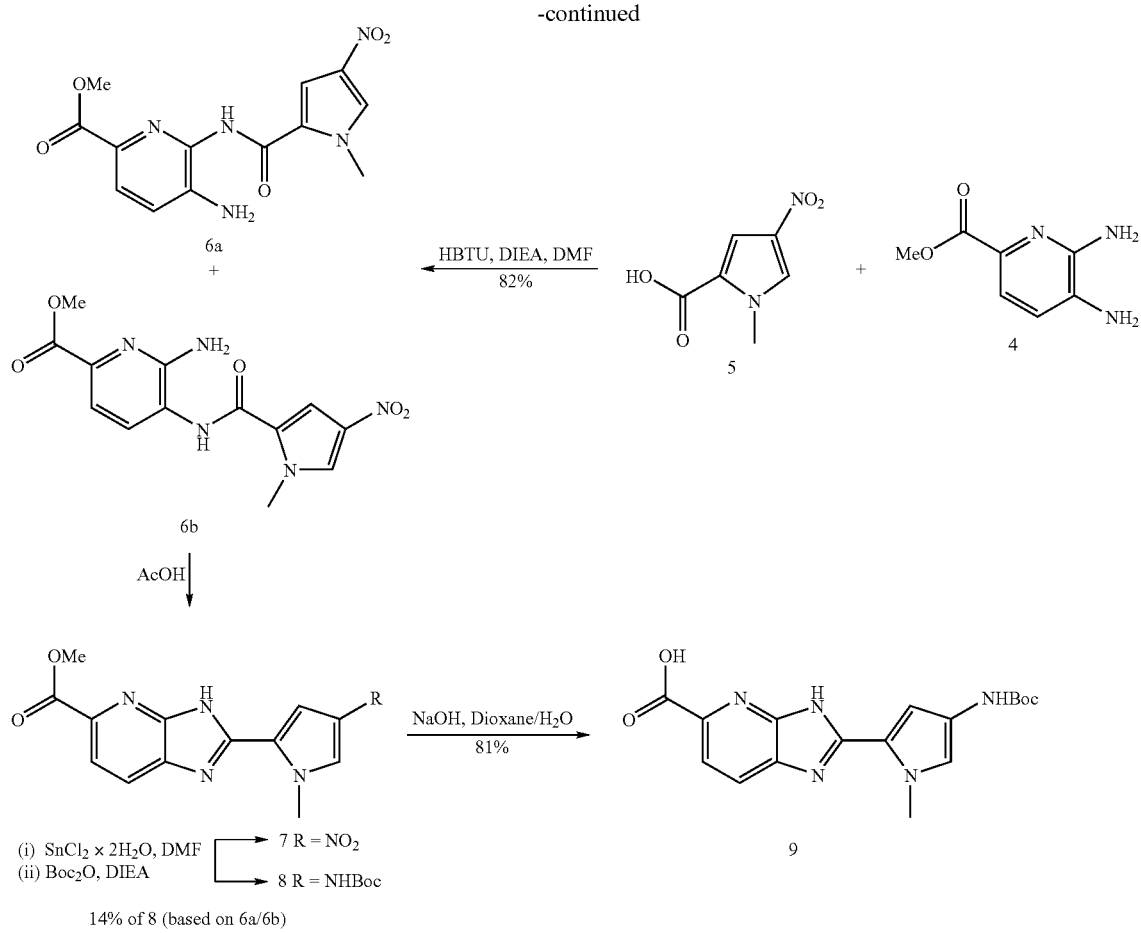

14% of 8 (based on 6a/6b)

2-Amino-3-nitro-6-bromo-pyridine (2) was synthesized in 2 steps following described procedures. (Mutterer, F.; Weis, C. D. *Helv. Chim. Acta*, 59, 229-235, 1976; EP0995 742 AI) Data of 2: $R_f$ 0.30 (hexane/EtOAc 1:1). $^1$H NMR (300 MHz, DMSO-$d_6$): δ 6.87 (d, J) 8.2 Hz, 1H), 8.23 (d, J=8.2 Hz, 1H), 8.25 (brs, 2H).

6-Amino-5-nitro-pyridine-2-carboxylic Acid Methyl Ester (3). To a solution of bromide 8 (8.0 g, 36.6 mmol) in DMF (130 mL) were added methanol (130 mL), Pd(OAc)$_2$ (248 mg, 1.1 mmol), triphenylphosphine (316 mg, 1.2 mmol) and Et$_3$N (20 mL). The mixture was stirred for 10 min and then transferred into a parr apparatus. After evacuating 3 times with CO, the reaction mixture was heated under a CO pressure of 15 atm to 60° C. for 15 h. The red/brown solution was then cooled to r.t., filtered through a pad of Celite, rinsed with EtOAc and concentrated. Purification by flash chromatography (hexane/EtOAc 1:1) afforded 4.4 g (61%) of 3 as a bright yellow solid. Data of 3: $R_f$ 0.57 (hexane/EtOAc 1:1). $^1$H NMR (300 MHz, DMSO-$d_6$): δ 3.85 (s, 3H), 7.27 (d, J=8.8 Hz, 1H), 8.09 (brs, 2H), 8.52 (d, J=8.8 Hz, 1H). $^{13}$C NMR (75 MHz, DMSO-$d_6$): δ 53.52, 113.10, 129.43, 137.48, 152.41, 153.79, 164.53. MS (ESI): m/z (rel intensity) 198 (100).

5,6-Diamino-pyridine-2-carboxylic Acid Methyl Ester (4). Methyl ester 3 (3.5 g, 18.0 mmol) was dissolved in methanol (300 mL) and EtOAc (300 mL) and the solution was degassed with Ar. After the addition of Pd/C (10 wt %, 0.7 g) the reaction mixture was stirred for 4 h under a hydrogen atmosphere. Filtration through a pad of Celite with EtOAc, evaporation of the solvent and purification by flash chromatography (EtOAc/MeOH 15:1) yielded 2.4 g (79%) of 4 as a deep red powder. Data of 4: $R_f$ 0.42 (EtOAc/MeOH 15:1). $^1$H NMR (300 MHz, DMSO-$d_6$): δ 3.68 (s, 3H), 5.51 (brs, 2H), 5.78 (brs, 2H), 6.67 (d, J$_1$) 7.7 Hz, 1H), 7.21 (d, J$_1$) 7.7 Hz, 1H). $^{13}$C NMR (75 MHz, DMSO-d6): δ 51.88, 116.32, 117.98, 132.40, 135.09, 147.93, 166.30. MS (ESI): m/z (rel intensity) 168 (100).

5-Amino-6-[(1-methyl-4-nitro-1H-pyrrole-2-carbonyl)-amino]-pyridine-2-carboxylic acid methyl ester and 6-amino-5-[(1-methyl-4-nitro-1H-pyrrole-2-carbonyl)-amino]-pyridine-2-carboxylic acid methyl ester (6a/6b). Carboxylic acid 5 (2.0 g, 11.8 mmol) and diamine 4 (1.8 g, 10.8 mmol) were dissolved in DMF (26 mL). 2-(1H-benzotriazole-1-yl)-1,1,3,3-tetramethyluronium hexafluorophosphate (HBTU) (4.4 g, 11.2 mmol) and N,N-diisopropylethylamine (DIEA) (2.5 mL) were added and the mixture was stirred under heating to 40° C. for 2 days. The reaction mixture was poured into ice and the precipitate formed was collected by filtration. Drying under hv provided 2.8 g (82%) as a mixture of both isomers 6a and 6b in a ratio of 3:2 (as determined by $^1$H NMR) as a red/brown solid which were used without separation. Data of 6a and 6b: $R_f$ 0.55, 0.65 (hexane/EtOAc 1:5). $^1$H NMR (300 MHz, DMSO-$d_6$): δ 3.76, 3.79, 3.91, 3.92

(4 s, 6H), 5.99 (brs, 0.6H), 6.35 (brs, 0.4H), 7.10 (d, J) 8.2 Hz, 0.6H), 7.30 (d, J) 8.2 Hz, 0.4H), 7.72-7.77 (m, 4H), 8.21 (s, 2H), 9.59 (brs, 0.4H), 10.33 (brs, 0.6H). $^{13}$C NMR (75 MHz, DMSO-$d_6$): δ 38.27, 38.45, 52.32, 52.70, 109.73, 109.90, 114.54, 119.42, 121.69, 121.95, 126.18, 126.62, 129.04, 129.13, 132.86, 133.59, 134.46, 136.23, 142.80, 144.78, 159.54, 162.87, 165.43, 165.83. MS (ESI): m/z (rel intensity) 320 (65). HRMS (FAB): m/z calcd for $C_{13}H_{14}N_5O_5$, 320.0987; found, 320.0994.

2-(4-tert-Butoxycarbonylamino-1-methyl-1H-pyrrole-2-yl)-3H-imidazo[4,5-b]pyridine-5-carboxylic Acid Methyl Ester (8). The aforementioned mixture of amino amides 6a and 6b (0.80 g, 2.4 mmol) was suspended in glacial acetic acid (20 mL) and heated to 80° C. for 7 h. The redish/grey suspension was then concentrated and dried under hv to obtain crude 7 as a brown solid in a ca. 1:1 mixture with unreacted amino amide 6a (as determined with $^1$H NMR). Data of 7: $R_f$ 0.62 (hexane/EtOAc 1:5). $^1$H NMR (300 MHz, DMSO-$d_6$): δ 3.86 (s, 3H), 3.92 (s, 3H), 7.40 (d, J=8.2, 1H), 7.98 (d, J=2.2, 1H), 8.26 (d, J=1.6, 1H), 8.41 (d, J=8.2, 1H), 10.26 (s, 1H). MS (ESI): m/z (rel intensity) 302 (13).

To a solution of unpurified 7 (0.75 g, 2.5 mmol) in DMF (13 mL) was added SnCl$_2$, 2H$_2$O (3.4 g, 15.0 mmol) and the mixture was stirred under heating to 50° C. for 36 h After completion of the reaction detected by TLC, Boc$_2$O (830 mg, 3.7 mmol) and DIEA (0.4 mL) were added to the reaction mixture. After stirring for 20 h another portion of Boc$_2$O (280 mg, 1.25 mmol) was added and stirring was continued for an additional 18 h. The mixture was concentrated, the residue redissolved in EtOAc, and washed with brine. The organic phase was dried over MgSO$_4$ and the solvent evaporated. Flash chromatography (hexane/EtOAc 1:4) afforded 130 mg (14%, 3 steps, based on 6a/6b) of 8 as a yellow powder. Data of 8: $R_f$ 0.45 (hexane/EtOAc 1:4). Compound 8 appears as two tautomers (1H/3H) on the NMR time scale at r.t. in a ratio of about 1:1;[21] heating the NMR probe to 70° C. resulted in only one set of signals. UV (MeOH): $\lambda_{max}$ 364. $^1$H NMR (300 MHz, DMSO-$d_6$, 70° C.): δ 1.43 (s, 9H), 3.85 (s, 3H), 4.04 (s, 3H), 6.94 (brs, 2H, D2O exchange), 7.08 (brs, 1H), 7.88-7.97 (m, 3H), 9.24 (s, 2H, D$_2$O exchange). $^{13}$C NMR (75 MHz, DMSO-d6): δ 28.85, 31.95, 37.42, 52.81, 79.07, 86.25, 104.53, 118.52, 119.90, 125.39, 146.79, 151.23, 153.37. MS (ESI): m/z (rel intensity) 372 (100). HRMS (FAB): m/z calcd for $C_{18}H_{22}N_5O_4$, 372.1671; found, 372.1660.

2-(4-tert-Butoxycarbonylamino-1-methyl-1H-pyrrole-2-yl)-3H-imidazo[4,5-b]pyridine-5-carboxylic acid (9). Compound 8 (60 mg, 0.6 mmol) was dissolved in 0.2 M NaOH in H$_2$O/dioxane 1:1 (7 mL) and stirred for 5 h at r.t. while the solution turned orange. The solution was cooled to 0° C. and 1N HCl was added dropwise until pH 1-2, while an orange precipitate developed. The product was separated by centrifugation, the supernatant removed, and the formed precipitate washed with cold H$_2$O (2×2 mL). Lyophilization afforded 46 mg (81%) of 9 as an orange solid. Data of 9: UV (MeOH): $\lambda_{max}$ 359. $^1$H NMR (300 MHz, DMSO-$d_6$): δ 1.46 (s, 9H), 4.05 (s, 3H), 7.01 (brs, 1H, D2O exchange), 7.15 (s, 1H), 7.98 (m, 3H), 9.30 (s, 1H, D$_2$O exchange). $^{13}$C NMR (75 MHz, DMSO-$d_6$): δ 28.96, 37.47, 79.21, 106.38, 118.65, 119.93, 120.44, 122.32, 124.99, 141.58, 150.32, 153.38, 166.53. MS (ESI): m/z (rel intensity) 358 (100). HRMS (FAB): m/z calcd for $C_{17}H_{20}N_5O_4$, 358.1515; found, 358.1506.

B. Preparation of Hydroxybenzimidazole-Pyrrole

For the synthesis of the N-Boc O-methyl-protected hydroxy-benzimidazole-pyrrole building block (Boc-PyHz-OH, 17) we also employed a cyclocondensation of the corresponding ortho-diamine and the carboxylic acid for the construction of the hydroxybenzimidazole unit. 4-acetylamino-5-chloro-2-methoxy-benzoic acid methyl ester (10), which is commercially available, was used as a starting material (Scheme 2). A regioselective nitration 11 followed by deacetylation of the amine under acidic conditions afforded methyl ester 12 in 66% yield over two steps, starting from 16. Hydrogenation of 12 on 10% Pd/C in the presence of triethylamine in MeOH at r.t. afforded cleanly ortho-diamine 13. The HBTU mediated coupling of diamine 13 and carboxylic acid 5 resulted in the two isomeric amino amides 14a and 14b, which cyclized by heating at 90° C. in glacial acetic acid 15. Reduction of the nitro group in 15 with Pd/C in the presence of hydrogen, in situ Boc-protection of the free amine to obtain 16 and final hydrolysis of the methyl ester with sodium hydroxide in dioxane/H$_2$O resulted in the desired N-Boc-O-methyl-protected hydroxybenzimidazole-pyrrole (Boc-PyHz-OH, 17).

Scheme 2.
Synthesis of Boc-protected O-methyl Hydroxybenzimidazole Amino Acid

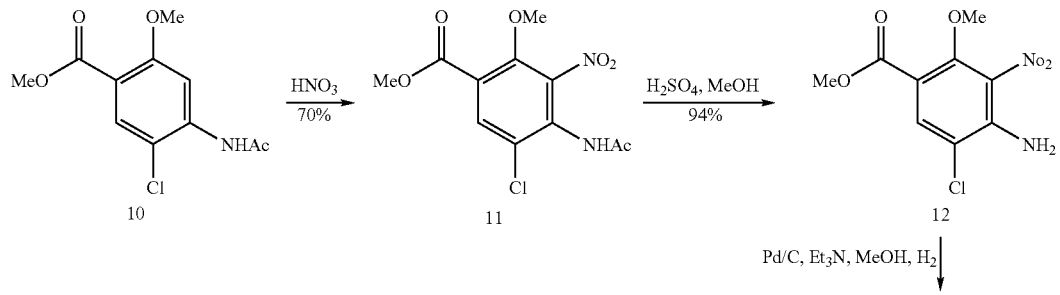

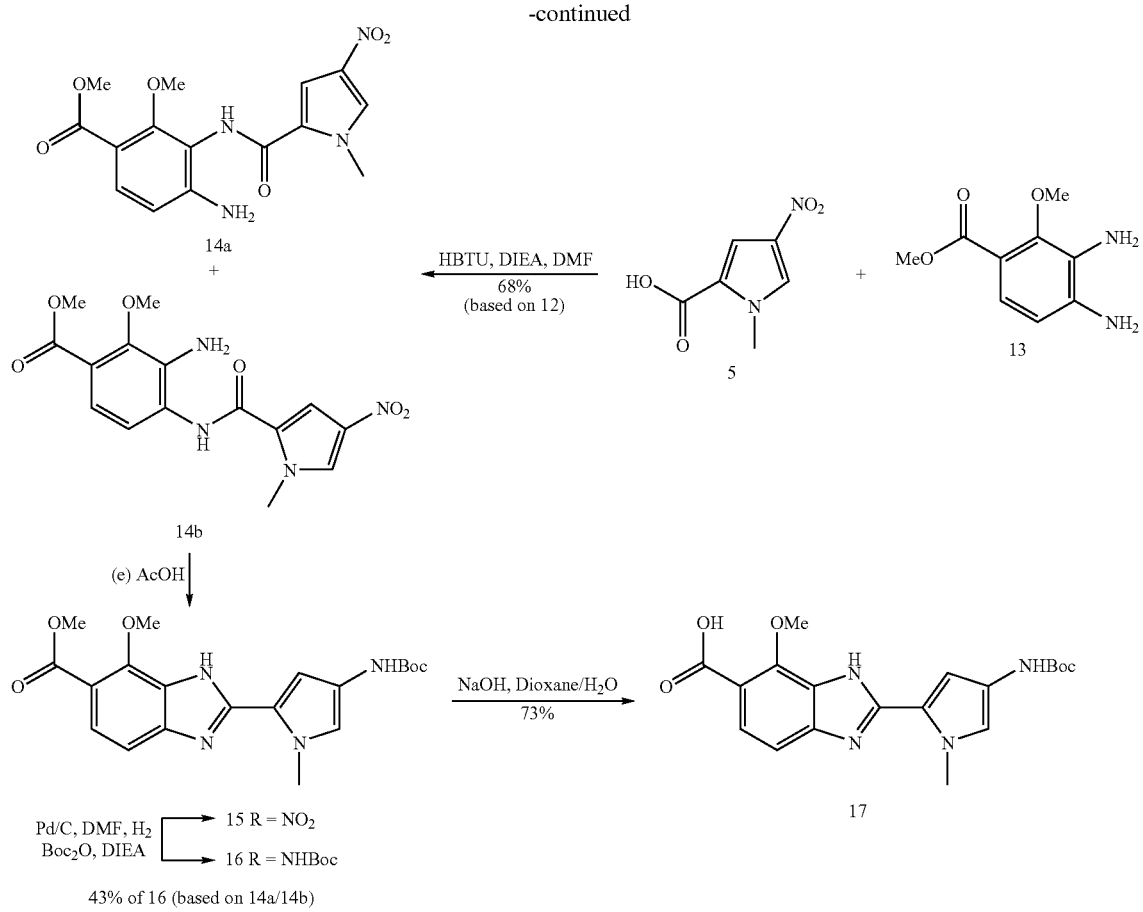

4-Acetylamino-5-chloro-2-methoxy-3-nitro-benzoic Acid Methyl Ester (11). Fuming nitric acid (33 mL) was added dropwise at 20° C. to compound 10 (13.0 g, 0.05 mol) over 15 min. After stirring for an additional 10 min at that temperature, the mixture was poured into ice water and EtOAc (100 mL) was added. After separating the organic phase, the aqueous phase was extracted with EtOAc. The combined organic phases were washed with brine, dried over $MgSO_4$ and concentrated. Drying under hv yielded 14.0 g (91%) of 11 as a beige solid. $^1$H NMR (300 MHz, DMSO-$d_6$): δ 2.01 (s, 3H), 3.84 (s, 3H), 3.87 (s, 3H), 8.12 (s, 1H), 10.30 (s, 1H).

4-Amino-5-chloro-2-methoxy-3-nitro-benzoic Acid Methyl Ester (12). Compound 11 (6.2 g, 20.5 mmol) was dissolved in methanol (70 mL), $H_2SO_4$ concentrated (4 mL) was added and the solution heated to reflux for 9 h. After cooling to r.t., the mixture was poured into ice (600 mL) and the precipitate formed was collected by filtration. Drying under hv gave 5.0 g (94%) of 12 as a yellow solid. Data of 12: $R_f$ 0.85 (hexane/EtOAc 1:4). $^1$H NMR (300 MHz, DMSO-$d_6$): δ 3.77 (s, 6H), 6.85 (brs, 2H), 7.82 (s, 1H). $^{13}$C NMR (75 MHz, DMSO-$d_6$): δ 52.80, 64.68, 110.40, 114.21, 133.80, 142.29, 153.60, 163.48. MS (ESI): m/z (rel intensity) 261 (100). HRMS (FAB): m/z calcd for $C_9H_9N_2O_5Cl$, 260.0200; found, 260.0197.

3,4-Diamino-2-methoxy-benzoic Acid Methyl Ester (13). Amine 12 (4.8 g, 18.4 mmol) was dissolved in methanol (250 mL) and the resulting solution was intensively degassed for 10 min with Ar. Pd/C (10 wt %, 4.5 g) was added, followed by $Et_3N$ (30 mL) and the resulting mixture was transferred to a parr apparatus. After being stirred for 6 h under a hydrogen atmosphere at 5 atm, the reaction mixture was filtered through a pad of Celite and rinsed with methanol. Evaporation of the solvent yielded crude diamine 13 as a brown gum (with residual $Et_3N$). Data for 13: $R_f$ 0.43 (hexane/EtOAc 1:4). $^1$H NMR (300 MHz, DMSO$d_6$): δ 3.62 (s, 3H), 3.67 (s, 3H), 4.38 (brs, 2H), 5.38 (brs, 2H), 6.30 (d, J=8.2 Hz, 1H), 6.96 (d, J=8.2 Hz, 1H). $^{13}$C NMR (75 MHz, DMSO-$d_6$): δ 51.77, 60.53, 109.36, 111.27, 121.35, 127.78, 141.95, 147.61. MS (ESI): m/z (rel intensity) 197 (55).

4-Amino-2-methoxy-3-[(1-methyl-4-nitro-1H-pyrrole-2-carbonyl)-amino]-benzoic Acid Methyl Ester (14a/14b). Carboxylic acid 5 (3.0 g, 17.6 mmol) and the aforementioned crude diamine 13 were dissolved in DMF (50 mL). HBTU (6.5 g, 16.5 mmol) and DIEA (3.4 mL) were added, and the reaction mixture was stirred for 1.5 days. The mixture was poured into ice and the precipitate collected by filtration. After washing with cold water and drying under hv provided 4.4 g (68%) as a mixture of the two isomeric amino amides 14a/14b in a ratio of about 1:1 (as determined by $^1$H NMR) as a beige solid. Data of 14a and 14b: $R_f$ 0.58, 0.74 (hexane/EtOAc 1:4). $^1$H NMR (300 MHz, DMSO-$d_6$): δ 3.61, 3.69, 3.75, 3.90 (4 s, 9H), 5.04 (brs, 1H), 5.89 (brs, 1H), 6.47 (d, J=8.1 Hz, 0.5H), 6.94 (d, J=8.2 Hz, 0.5H), 7.09 (d, J=8.2 Hz, 0.5H), 7.49 (d, J=8.1 Hz, 0.5H), 7.63-7.69 (m, 1H), 8.17-8.20

(m, 1H), 9.30 (brs, 0.5H), 9.65 (brs, 0.5H). $^{13}$C NMR (75 MHz, DMSOd$_6$): δ 38.18, 38.30, 51.98, 52.67, 61.23, 62.01, 108.98, 109.54, 110.07, 110.38, 115.48, 117.35, 121.92, 122.19, 127.19, 128.57, 131.83, 134.44, 147.52, 152.26, 159.57, 160.08, 165.67, 166.49. MS (ESI): m/z (rel intensity) 349 (100). HRMS (FAB): m/z calcd for C$_{15}$H$_{16}$N$_4$O$_6$, 348.1069; found, 348.1085.

4-Methoxy-2-(1-methyl-4-nitro-1H-pyrrol-2-yl)-3H-benzimidazole-5-carboxylic Acid Methyl Ester (15). The aforementioned mixture of amides 14a/14b (500 mg, 1.43 mmol) was suspended in glacial acetic acid (8 mL) and heated to 90° C. for 7 h. Most of the solvent was evaporated, and the yellow residue was suspended in Et$_2$O. After being vigorously stirred for 20 min, the precipitate was filtered and washed with Et$_2$O. Drying under hv gave 404 mg (85%) of 15 as a beige solid. Data of 15: R$_f$ 0.80 (hexane/EtOAc 1:5). $^1$H NMR (300 MHz, DMSOd$_6$): δ 3.76 (s, 3H), 4.14 (s, 3H), 4.34 (s, 3H), 7.14-7.17 (m, 1H), 7.48-7.55 (m, 3H), 8.25 (s, 1H). MS (ESI): m/z (rel intensity) 331 (98).

2-(4-tert-Butoxycarbonylamino-1-methyl-1H-pyrrol-2-yl)-4-meth-oxy-3H-benzimidazole-5-carboxylic Acid Methyl Ester (16). Compound 15 (400 mg, 1.21 mmol) was dissolved in DMF (10 mL) and Pd/C (10 wt %, 150 mg) was added. The mixture was transferred into a parr apparatus and stirred for 5 h under a hydrogen atmosphere of 10 atm. After the TLC revealed no starting material, the mixture was transferred into a round-bottom flask and Boc$_2$O (400 mg, 1.81 mmol) and DIEA (0.5 mL) were directly added. The reaction mixture was stirred overnight, filtered through a pad of Celite, rinsed with EtOAc, and concentrated in vacuo. Purification by flash chromatography (hexane/EtOAc 1:2) afforded 248 mg (51%) of 16 as a beige solid. Data of 16: R$_f$ 0.34 (hexane/EtOAc 1:2). $^1$H NMR (300 MHz, DMSOd$_6$): δ 1.43 (s, 9H), 3.75 (s, 3H), 3.99 (s, 3H), 4.31 (s, 3H), 6.78 (s, 2H, CH, D$_2$O exchange), 6.95 (s, 1H), 7.05 (d, J=8.2 Hz, 1H), 7.45 (d, J=8.6 Hz, 1H), 9.18 (brs, 1H, D$_2$O exchange). $^{13}$C NMR (75 MHz, DMSO-d$_6$): δ 28.62, 38.20, 51.98, 62.01, 108.98, 110.08, 115.48, 127.19, 128.57, 131.84, 152.25, 160.09, 165.67. UV (MeOH): λ$_{max}$ 327. MS (ESI): m/z (rel intensity) 401 (100).

2-(4-tert-Butoxycarbonylamino-1-methyl-1H-pyrrol-2-yl)-4-meth-oxy-3H-benzoimidazole-5-carboxylic Acid 17. Methyl ester 16 (51 mg, 0.13 mmol) was dissolved in 1 M NaOH (1:1 dioxane/H$_2$O, 5 mL) and stirred overnight at r.t and an additional 3 h at 50° C. The reaction mixture was cooled to 0° C. and 1N HCl was added dropwise to adjust the pH to 3-4, while a white precipitate was formed. Separation of the product was accomplished by centrifugation and decanting of the supernatant. Lyophilization gave 36 mg (73%) of 17 as a beige solid. Data of 17: $^1$H NMR (500 MHz, DMSO-d$_6$): δ 1.40 (s, 9H), 3.97 (s, 3H), 4.28 (s, 3H), 6.76 (s, 1H), 6.92 (s, 1H), 7.02 (d, J=8.2 Hz, 1H), 7.44 (d, J=8.2 Hz, 1H), 9.13 (s, 1H), 12.20 (brs, 1H). $^{13}$C NMR (125 MHz, DMSO-d$_6$): δ 27.80, 36.34, 60.78, 78.29, 102.88, 104.47, 114.67, 116.12, 119.79, 123.54, 124.96, 135.00, 139.02, 145.90, 150.62, 152.78, 167.70. UV (H$_2$O): λ$_{max}$ 319. MS (ESI): m/z (rel intensity) 387 (100). HRMS (FAB): calcd for C$_{19}$H$_{23}$N$_4$O$_5$, 387.1668; found, 387.1658.

C. Preparation of Benzimidazole-Imidazole, Benzimidazole-Methoxypyrrole, Benzimidazole-Pyrrole, and Benzimidazole-Imidazole-Pyrrole Boc-protected benzimidazole-imidazole (Boc-ImBi-OH, 23a), benzimidazole-methoxypyrrole (Boc-IpBi-OH, 23b), benzimidazole-pyrrole (Boc-BiPy-OH, 23c), and benzimidazole-imidazole-pyrrole (Boc-PyImBi-OH, 25) amino acids. As shown in Scheme 3, the benzimidazole scaffold was obtained by cyclodehydration of amides 20a,b, which were in turn prepared from precursors 18a,b by means of an HBTU-mediated coupling, in acetic acid or by condensation of pyrrole-aldehyde 18c with ortho-diamine 19 and in situ Fe$^{III}$/Fe$^{II}$-catalyzed oxidative cyclodehydrogenation of the Schiff's base intermediate. Subsequent reduction of the nitro group in 21a-c and Boc protection of the resulting aminoesters furnished the protected aromatic amino acid esters 22a-c in moderate to good yield. The desired carboxylic acids 23a-c were obtained by hydrolysis of the esters 22a-c with sodium hydroxide in dioxane. As will be discussed in the following example, it was found advantageous for the solid-phase synthesis to use Boc protected amino acid 25 instead of 23a as building block to incorporate the BiIm moiety into the hairpin polyamide 2b. For the synthesis of 25, nitro compound 21a was reduced and subsequently reacted with Boc-Py-OBt which produced ester 24 in moderate yield. Saponofication of 10 furnished the protected amino acid 25 in 94% yield.

Scheme 3.
Synthesis of Boc-protected Benzimidazole Amino Acids

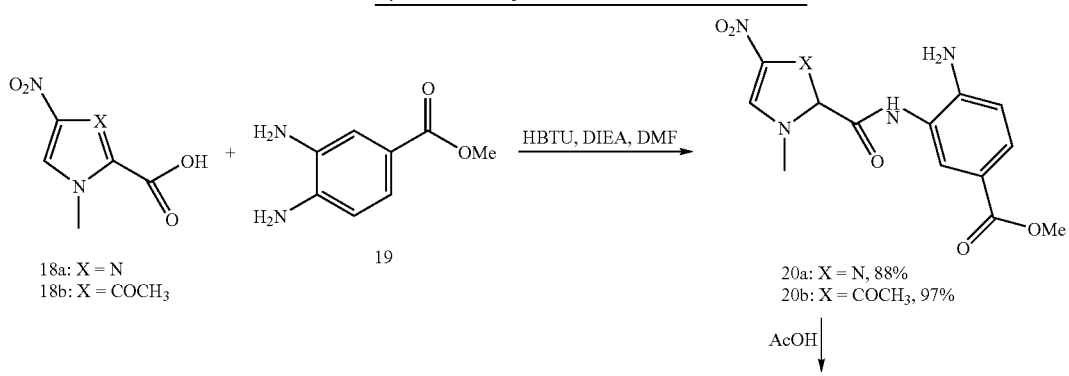

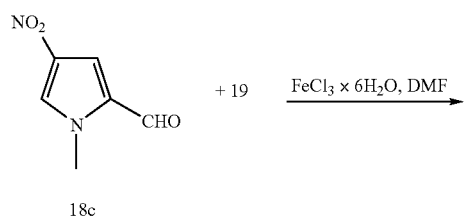
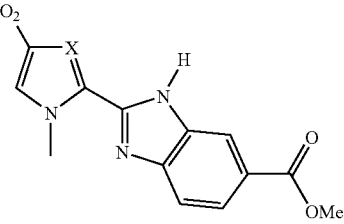
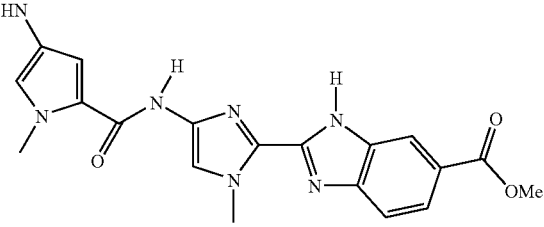
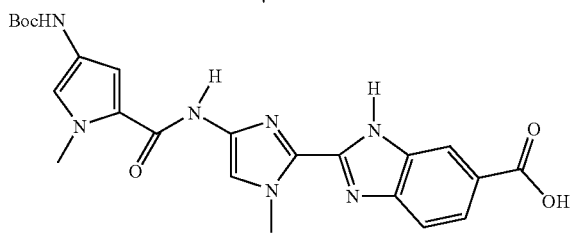
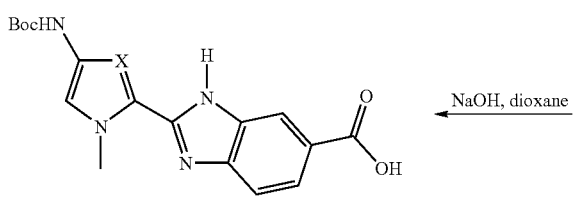
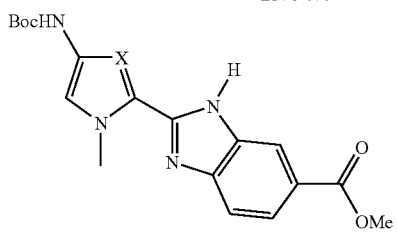

3-Methoxy-1-methyl-4-nitro-1H-pyrrole-2-carboxylic acid (18 b): 3-Methoxy-1-methyl-4-nitro-1H-pyrrole-2-carboxylic ethyl ester (5.50 g, 24.1 mmol) was dissolved in ethanol (100 mL). NaOH (aqueous, 1 m, 100 mL) was added and the solution stirred for 13 h at ambient temperature. The yellow solution was carefully acidified with aqueous HCl (1 m) to pH 2-3. The formed white precipitate was filtered, washed with water and dried in vacuo to yield the title compound 18b as a white powder (3.85 g, 80%). $^1$H NMR (300 MHz, [D$_6$] DMSO): δ=3.80 (s, 3H), 3.82 (s, 3H), 8.10 (s, 1H); C NMR (75 MHz, [D$_6$] DMSO): δ=38.4, 62.4, 114.6, 126.4, 127.0, 145.1, 160.5; MS (EI): m/z: 201 [M+H]$^+$; HR-MS (EI): calcd for C$_7$H$_8$N$_2$O$_5$: 200.0433; found: 200.0435.

4-Amino-3-[1-methyl-4-nitro-1H-imidazole-2-carbonyl)-amino]-benzoic methyl ester (20a): Carboxylic acid 18a (2.57 g, 15.0 mmol) and methyl 3,4-diamino-benzoate (19) (2.49 g, 15.0 mmol) were dissolved in DMF (30 mL). HBTU (5.72 g, 15.0 mmol) was added to the solution followed by DIEA (3 mL). After stirring for 20 h at ambient temperature the reaction mixture was poured into ice water. The precipitate was filtered, washed with water and dried in vacuo to yield the title compound 20a as a yellow powder (4.22 g, 88%). $^1$H NMR (300 MHz, [D$_6$] DMSO): δ=3.74 (s, 3H), 4.01 (s, 3H), 5.89 (s, 2H), 6.74 (d, J=8.8 Hz, 1H), 7.59 (dd, J$_1$=8.8 Hz, J$_2$=1.6 Hz, 1H), 7.71 (d, J=1.6 Hz, 1H), 8.64 (s, 1H), 10.04 (s, 1H); $^{13}$C NMR (75 MHz, [D$_6$] DMSO): δ=36.6, 51.4, 114.5, 115.9, 120.3, 126.5, 128.7, 129.0, 137.7, 144.1, 148.6, 156.7, 165.8; MS (ESI): m/z: 320 [M+H]$^+$; HR-MS (E): calcd for C$_{13}$H$_{13}$N$_5$O$_5$: 319.0916; found: 319.0929.

4-Amino-3-[(3-methoxy-1-methyl-4-nitro-1H-pyrrole-2-carbonyl)-amino]-benzoic methyl ester (20b): Carboxylic acid 18b (2.17 g, 10.8 mmol) and methyl 3,4-diamino-benzoate (19) (1.81 g, 10.8 mmol) were dissolved in DMF (26 mL). HBTU (4.11 g, 10.8 mmol) was added to the solution followed by DIEA (2.6 mL). After stirring for 20 h at ambient temperature the reaction mixture was poured into ice water. The precipitate was filtered, washed with water and dried in vacuo to yield the title compound 20b as a yellow powder (3.66 g, 97%).

$^1$H NMR (300 MHz, [D$_6$] DMSO): δ=3.75 (s, 3H), 3.86 (s, 3H), 3.95 (s, 3H), 5.82 (s, 2H), 6.78 (d, J=8.4 Hz, 1H), 7.57 (dd, J$_1$=8.4 Hz, J$_2$=2.0 Hz, 1H), 7.93 (d, J=2.0 Hz, 1H), 8.13 (s, 1H), 8.95 (s, 1H); $^{13}$C NMR (75 MHz, [D$_6$] DMSO): δ=38.0, 51.4, 62.9, 114.7, 116.4, 116.5, 121.3, 125.9, 126.4, 127.3, 128.0, 141.4, 147.3, 157.8, 165.9; MS (ESI): m/z: 349 [M+H]$^+$; HR-MS (EI): calcd for C$_{15}$H$_{16}$N$_4$O$_6$: 348.1069; found: 348.1072.

2-(1-Methyl-4-nitro-1H-imidazol-2-yl)-1H-benzimidazole-5-carboxylic methyl ester (21a): Amide 20a (3.99 g, 12.5 mmol) was suspended in acetic acid (50 mL) and heated to 140° C. for 6 h. The solvent was removed in vacuo, diethyl ether was added, the yellow precipitate filtered and dried in vacuo affording the title compound 21a as an off-white powder (3.57 g, 95%). $^1$H NMR (300 MHz, [D$_6$] DMSO): δ=3.87 (s, 3H), 4.26 (s, 3H), 7.57-8.34 (m, 3H), 8.71 (s, 1H), 13.78 (s, 1H); $^{13}$C NMR (75 MHz, [D$_6$] DMSO): δ=36.8, 52.1, 112.2, 113.8, 119.1, 120.9, 123.8, 124.5, 126.2, 136.3, 144.2, 145.6, 166.3; MS (ESI): m/z: 302 [M+H]$^+$; HR-MS (EI): calcd for C$_{13}$H$_{11}$N$_5$O$_4$: 301.0811; found: 301.0805.

2-(3-Methoxy-1-methyl-4-nitro-1H-pyrrol-2-yl)-3H-benzimidazole-5-carboxylic methyl ester (21 b): Amide 20b (3.56 g, 10.2 mmol) was suspended in acetic acid (40 mL) and refluxed at 140° C. for 12 h. Upon cooling to room temperature a yellow solid precipitated that was filtered, suspended in diethyl ether, filtered, and dried in vacuo to yield the title compound 21b as a yellow solid (3.33, 98%). $^1$H NMR (300 MHz, [D$_6$] DMSO): δ=3.93 (s, 1.5H), 3.94 (s, 1.5H), 3.97 (s, 3H), 4.15 (s, 3H), 7.72-7.95 (m, 2H), 8.24 (s, 1H), 8.25-8.32 (m, 1H), 12.44 (s, 0.5H), 12.52 (s, 0.5H). At room temperature the presence of two benzimidazole tautomers (1H/3H) could be deduced from the $^1$H NMR spectra. The ratio between the two isomers was roughly estimated as 1:1 based on the integration of the protons at δ=3.93/3.94 and 12.44/12.52. $^{13}$C NMR (75 MHz, [D$_6$] DMSO): δ=38.5, 52.0, 62.7, 111.8, 113.62, 113.75, 118.2, 120.0, 122.72, 123.18, 123.45, 123.65, 126.38, 126.53, 133.5, 137.4, 140.63, 140.87, 142.2, 144.29, 145.16, 145.98, 166.4; MS (ESI): m/z: 331 [M+H]$^+$; HR-MS (EI): calcd for C$_{15}$H$_{14}$N$_4$O$_5$: 330.0964; found: 330.0965.

2-(1-Methyl-4-nitro-1H-pyrrol-2-yl)-1H-benzimidazole-5-carboxylic methyl ester (21 c): Methyl 3,4-diamino-benzoate (19) (2.66 g, 16.0 mmol) was dissolved in DMF (75 mL). A solution of 1-methyl-4-nitro-1H-pyrrole-2-carbaldehyde (18c, 2.31 g, 15.0 mmol) in DMF (200 mL) was added and the reaction mixture was heated to 90° C. for 60 min. Iron-trichloride hexahydrate (120 mg) was added and the mixture was heated to 120° C. for 6 h while air was bubbled through the solution. The reaction mixture was cooled to room temperature. The volume of the solvent was reduced in vacuo to ca. 50 mL and the brown solution was cooled to −20° C. for 4 h. The formed precipitate was filtered, washed with CH$_2$Cl$_2$ until the washing solution was colorless, and dried in vacuo to yield the title compound 21c as a yellow powder (3.13 g, 69%). $^1$H NMR (300 MHz, [D$_6$] DMSO): δ=3.85 (s, 1.5H), 3.86 (s, 1.5H), 4.16 (s, 3H), 7.50-8.31 (m, 5H), 13.15 (s, 0.5H), 13.18 (s, 0.5H). At room temperature the presence of two benzimidazole tautomers (1H/3H) could be deduced from the $^1$H NMR spectra. The ratio between the two isomers was roughly estimated as 1:1 based on the integration of the protons at δ=3.85/3.86 and 13.15/13.18. $^{13}$C NMR (75 MHz, [D$_6$] DMSO): δ=38.0, 52.0, 106.9, 111.0, 112.5, 118.7, 120.3, 122.9, 123.5, 123.9, 128.0, 134.8, 146.6, 166.4; MS (ESI): m/z: 301 [M+H]$^+$; HRMS (EI): calcd for C$_{14}$H$_{12}$N$_4$O$_4$: 300.0858; found: 300.0847.

2-(4-tert-Butoxycarbonylamino-1-methyl-1H-imidazol-2-yl)-1H-benzimidazole-5-carboxylic methyl ester (22 a): Nitro-ester 21a (2.00 g, 6.64 mmol) was dissolved in DMF (200 mL). Pd/C (10 wt. %, 360 mg) was added and the mixture was hydrogenated at 600 psi for 2 h at ambient temperature. The reaction mixture was filtered through Celite to remove the catalyst and the filtrate was treated with Boc$_2$O (2.17 g, 9.96 mmol) and DIEA (20 mL) and stirred at 70° C. for 2 d. After evaporation of the solvent the residue was dissolved in diethyl ether (150 mL) and the solution was washed with water and brine. The organic phase was dried with MgSO$_4$, the solvent was evaporated, and the crude product purified by column chromatography on silica gel (n-hexane/EtOAc 1:1) to give the title compound 22a as a white solid (0.74 g, 30%). $^1$H NMR (300 MHz, [D$_6$] DMSO): δ=1.45 (s, 9H), 3.84 (s, 3H), 4.11 (s, 3H), 7.28 (s, 1H), 7.54-8.22 (m, 4H), 9.48 (s, 1H), 12.98, 3.01 (2 s, 1H); MS (ESI): m/z 372 [M+H]$^+$; HR-MS (EI): calcd for C$_{18}$H$_{21}$N$_5$O$_4$: 371.1593; found: 371.1584.

2-(4-tert-Butoxycarbonylamino-3-methoxy-1-methyl-1H-pyrrol-2-yl)-3H-benzimidazole-5-carboxylic methyl ester (22 b): Nitro-ester 7b (1.00 g, 3.03 mmol) was dissolved in 9:1 DMF/acetonitrile (60 mL). Tin-dichloride dihydrate (5.00 g, 22.2 mmol) was added to the solution and the reaction mixture was heated to 50° C. for 14 h. After cooling the yellow solution to room temperature Boc$_2$O (3.96 g, 18.1 mmol), DMF (5 mL) and DIEA (7 mL) were added and the reaction mixture heated to 50° C. for 4 h. The solvent was evaporated, and the residue was extracted several times with ethyl acetate. The extracts were combined, washed with water, and dried with MgSO$_4$. After evaporation of the solvent the crude product was purified by column chromatography on silica gel (CH$_2$Cl$_2$/ethyl acetate 4:1) to afford the title compound 22b as a white solid (0.56 g, 48%). $^1$H NMR (300 MHz, [D$_6$] DMSO): δ=1.44 (s, 9H), 3.79 (s, 3H), 3.85 (s, 3H), 3.96 (s, 3H), 6.96 (s, 1H), 7.56-7.79 (m, 2H), 8.16 (s, 1H), 8.55 (s, 1H), 11.94, 12.01 (2 s, 1H); MS (ESI): m/z: 401 [M.H]; HR-MS (EI): calcd for C$_{20}$H$_{24}$N$_4$O$_5$: 400.1746; found: 400.1742.

2-(4-tert-Butoxycarbonylamino-1-methyl-1H-pyrrol-2-yl)-1H-benzimidazole-5-carboxylic acid methyl ester (22 c): Nitro-ester 21c (1.50 g, 5.00 mmol) was dissolved in DMF (250 mL). Pd/C (10 wt. %, 300 mg) was added and the mixture was hydrogenated at 600 psi overnight at ambient temperature. The reaction mixture was filtered through Celite to remove the catalyst and the filtrate was treated with Boc$_2$O (1.63 g, 7.50 mmol) and DIEA (25 mL) and stirred at 70° C. for 2 d. After evaporation of the solvent the residue was dissolved in diethyl ether (150 mL) and the solution was washed with water and brine. The organic phase was dried with MgSO$_4$, the solvent was evaporated, and the crude product purified by column chromatography on silica gel (CH$_2$Cl$_2$/EtOAc 4:1) to give the title compound 22c as a white solid (1.08 g, 58%). $^1$H NMR (300 MHz, [D$_6$] DMSO): δ=1.44 (s, 9H), 3.82 (s, 3H), 4.02 (s, 3H), 6.84 (s, 1H), 6.99 (s, 1H), 7.42-8.16 (m, 3H), 9.21 (s, 1H), 12.74, 12.79 (2 s, 1H); MS (ESI): m/z: 371 [M+H]$^+$; HR-MS (EI): calcd for C$_{19}$H$_{22}$N$_4$O$_4$: 370.1641; found: 370.1645.

2-(4-tert-Butoxycarbonylamino-1-methyl-1H-imidazol-2-yl)-1H-benzimidazole-5-carboxylic acid (23a): Methyl ester 22a (700 mg, 1.88 mmol) was dissolved in dioxane (140 mL). NaOH (aqueous, 1 m, 140 mL) was added and the solution stirred for 18 h at ambient temperature. The yellow solution was carefully acidified with aqueous HCl (1 m) to pH 3-4. The formed precipitate was filtered, washed with water, and dried in vacuo to provide the title compound 23a as a white powder (512 mg, 76%). $^1$H NMR (300 MHz, [D$_6$] DMSO): δ=1.47 (s, 9H), 4.13 (s, 3H), 7.29 (s, 1H), 7.43-8.30 (m, 3H), 9.49 (s, 1H), 12.71 (s, 1H), 12.95 (s, 1H); $^{13}$C NMR (75 MHz, [D$_6$] DMSO): δ=28.2, 35.2, 78.9, 111.5, 112.5, 113.5, 118.3, 120.6, 123.3, 124.7, 132.4, 137.9, 145.8, 152.8, 167.6; MS (ESI): m/z: 358 [M+H]$^+$; HR-MS (FAB): calcd for C$_{17}$H$_{20}$N$_5$O$_4$: 358.1515; found: 358.1504 [M+H]$^+$.

2-(4-tert-Butoxycarbonylamino-3-methoxy-1-methyl-1H-pyrrol-2-yl)-3H-benzimidazole-5-carboxylic acid (23 b): Methyl ester 22b (400 mg, 1.00 mmol) was dissolved in dioxane (10 mL). NaOH (aqueous, 1M, 10 mL) was added and the solution stirred for 12 h at ambient temperature. The yellow solution was carefully acidified with aqueous HCl (1 M) to pH 3-4, and extracted several times with diethyl ether. Evaporation of the solvent afforded the title compound 23b as a yellow powder (351 mg, 91%). $^1$H NMR (300 MHz, [D$_6$] DMSO): δ=1.43 (s, 9H), 3.81 (s, 3H), 3.98 (s, 3H), 6.96 (s, 1H), 7.61 (d, J=8.4 Hz, 1H), 7.81 (d, J=8.4 Hz, 1H), 8.20 (s, 1H), 8.53 (s, 1H), 11.96 (s, 1H), 12.60 (s, 1H); $^{13}$C NMR (75 MHz, [D$_6$] DMSO): δ=28.3, 37.3, 61.1, 78.6, 109.6, 111.2, 112.9, 113.3, 117.3, 119.8, 120.3, 123.0, 123.8, 141.4, 147.1, 154.1, 168.0; MS (ESI): m/z: 387 [M+H]$^+$; HR-MS (FAB): calcd for C$_{19}$H$_{23}$N$_4$O$_5$: 387.1668; found: 387.1676 [M+H]$^+$.

2-(4-tert-Butoxycarbonylamino-1-methyl-1H-pyrrol-2-yl)-1H-benzimidazole-5-carboxylic acid (23 c): Methyl ester 22c (1.04 g, 2.80 mmol) was dissolved in dioxane (280 mL). NaOH (aqueous, 1 m, 280 mL) was added and the solution heated to 80° C. for 2 h. The yellow solution was carefully acidified with aqueous HCl (1 m) to pH 3-4. The formed precipitate was filtered, washed with water, and dried in vacuo to provide the title compound 23c as a white powder (990 mg, 99%). $^1$H NMR (300 MHz, [D$_6$] DMSO): δ=1.46 (s, 9H), 4.04 (s 3H), 7.04 (s, 1H), 7.24 (s, 1H), 7.73 (d, J=8.4 Hz, 1H), 7.96 (dd, J$_1$=8.4 Hz, J$_2$=1.5 Hz, 1H), 8.20 (d, J=1.5 Hz, 1H), 9.40 (s, 1H); $^{13}$C NMR (75 MHz, [D$_6$] DMSO): δ=28.2, 36.4, 78.7, 107.2, 113.5, 115.0, 120.2, 124.8, 125.6, 126.7, 132.9, 136.2, 144.2, 152.6, 166.7; MS (ESI): m/z: 357 [M+H]$^+$; HR-MS (FAB): calcd for C$_{18}$H$_{21}$N$_4$O$_4$: 357.1562; found: 357.1576 [M+H]$^+$.

2-{4-[(4-tert-Butoxycarbonylamino-1-methyl-1H-pyrrole-2-carbonyl)-amino]-1-methyl-1H-imidazol-2-yl}-1H-benzimidazole-5-carboxylic methyl ester (24): Pd/C (10 wt. %, 150 mg) was added to a solution of nitro-ester 21a (1.00 g, 3.32 mmol) in DMF (100 mL) and the mixture was hydrogenated at 450 psi for 2 h at ambient temperature. The reaction mixture was filtered through Celite to remove the catalyst and the filtrate was treated immediately with Boc-Py-OBt (27a, 1.42 g, 3.98 mmol) and DIEA (20 mL) and stirred at 60° C. for 18 h. The resulting yellow solution was poured into ice water and extracted with EtOAc. The organic phase was washed with 10% citric acid, brine, and saturated aqueous sodium bicarbonate and dried with MgSO$_4$. Evaporation of the solvent yielded the crude product as a yellow foam which was purified by column chromatography on silica gel (n-hexane/ EtOAc 1:2) to give the title compound as a beige solid (409 mg, 25%). $^1$H NMR (300 MHz, [D$_6$] DMSO): δ=1.45 (s, 9H), 3.82 (s, 3H), 3.87 (s, 3H), 4.16 (s, 3H), 6.88 (s, 1H), 6.99 (s, 1H), 7.60-8.20 (m, 4H), 9.11 (s, 1H), 10.23 (s, 1H), 13.03 (br s, 1H); MS (ESI): m/z: 494 [M+H]$^+$; HR-MS (FAB): calcd for C$_{24}$H$_{28}$N$_7$O$_5$: 494.2151; found: 494.2143 [M+H]$^+$.

2-{4-[(4-tert-Butoxycarbonylamino-1-methyl-1H-pyrrole-2-carbonyl)-amino]-1-methyl-1H-imidazol-2-yl}-1H-benzimidazole-5-carboxylic acid (25): Methyl ester 10 (220 mg, 0.45 mmol) was dissolved in dioxane (20 mL). NaOH (aqueous, 1M, 20 mL) was added and the solution stirred for 18 h at ambient temperature. The yellow solution was carefully acidified with aqueous HCl (1M) to pH 3-4. The formed precipitate was filtered, washed with water, and dried in vacuo to provide the title compound as a beige powder (203 mg, 94%). $^1$H NMR (300 MHz, [D$_6$] DMSO): δ=1.44 (s, 9H), 3.82 (s, 3H), 4.16 (s, 3H), 6.88 (s, 1H), 6.99 (s, 1H), 7.59-8.18 (m, 4H), 9.12 (s, 1H), 10.23 (s, 1H), 12.95 (br s, 1H); $^{13}$C NMR (75 MHz, [D$_6$] DMSO): δ=28.3, 35.2, 36.2, 78.3, 104.9, 114.01, 114.32, 117.8, 121.99, 122.32, 123.4, 124.71, 124.81, 132.5, 137.4, 143.7, 145.76, 145.84, 152.7, 158.6, 167.6; MS (ESI): m/z: 480 [M+H]$^+$; HR-MS (ESI): calcd for C$_{23}$H$_{26}$N$_7$O$_5$: 480.1995; found: 480.2014 [M+H]$^+$.

D. Preparation of Im-HzOMe

Compounds Im-HzOMe-OH (29) and Boc-Im-HzOMe-OH (31) were prepared from diamine 26 as shown below in Scheme 4.

Im-HzOMe-OH (29). To a solution of diamine (26) in EtOAc was added Im-COCCl$_3$ and DIEA. The mixture was heated at 35° C. and stirred for 3 h at which time a precipitate formed. The precipitate was filtered, washed, and dissolved in neat AcOH. The mixture was heated at 90° C. to provide the product Im-HzOMe-OMe (27) cleanly. The formation of the cyclocondensation product (27) can be followed easily by TLC and the appearance of a bright fluorescent spot under UV visualization. Im-HzOMe-OMe (27) was then saponified using 1N NaOH in MeOH to provide Im-HzOMe-OH (29). This synthetic route did not require any chromatography steps. Also, the condensation products were obtained cleanly at mild temperatures and neutral conditions.

Boc-Im-HzOMe-OH (31). Diamine (26) was coupled to NO$_2$-Im-OH using HBTU and DIEA in DMF. The mixture was stirred at ambient temperature for 24 h and then poured into water to produce a precipitate. The precipitate was collected, dissolved in neat AcOH, and heated at 90° C. to provide the cyclocondensation product NO$_2$-Im-HzOMe-OMe (28). Reduction of the imidazole nitro group was accomplished using H$_2$ Pd/C in a mixture of DMF and DIEA, followed by the addition of (Boc)$_2$O to provide the Boc-protected amino ester Boc-Im-HzOMe-OMe (30). 30 was saponified using a mixture of 1N NaOH and MeOH to provide the final product Boc-Im-HzOMe-OH (31). The synthesis of NO$_2$-Im-HzOMe-OMe (28) was attempted using the trichloroketone protocol provided above for 27 but was repeatedly unsuccessful. It appears the additional reactivity of the NO$_2$-Im-COCCl$_3$ species results in di-acylation of the diamine (26) and prohibits cyclocondensation.

Scheme 4.
Synthesis of Im-HzOMe-OH and Boc-Im-HzOMe-OH

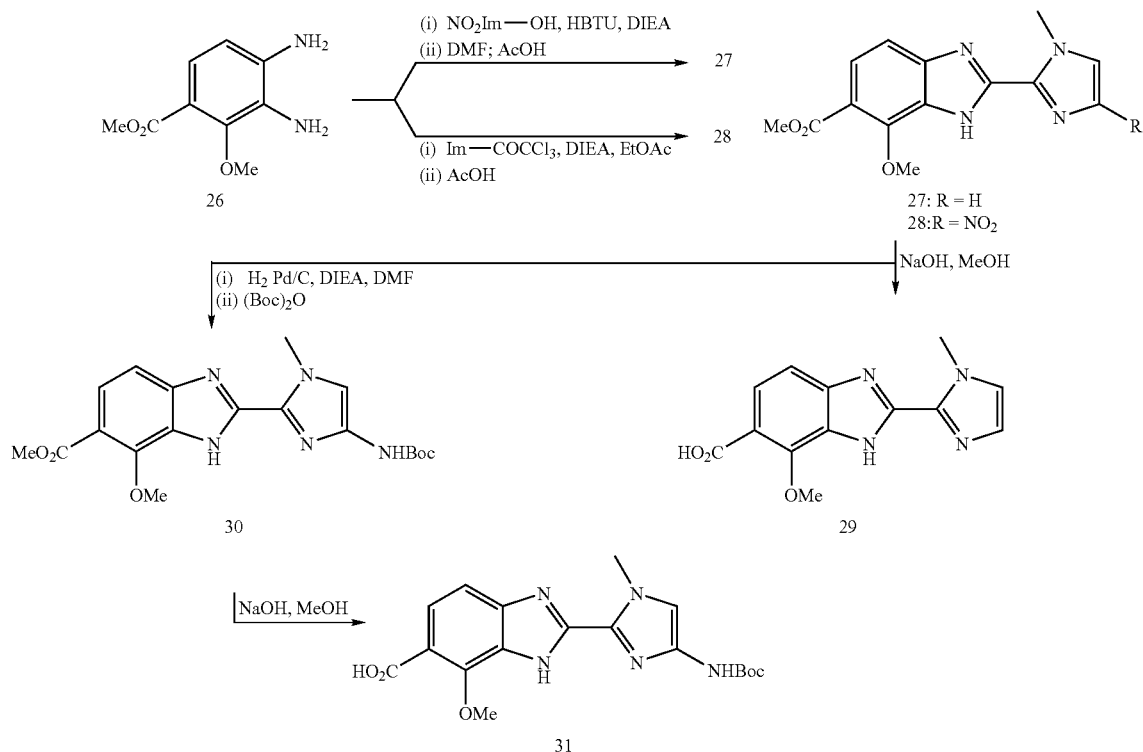

Methy 7-methoxy-2-(1-methylimidazol-2-yl)benzimidazole-6-carboxylate (Im-HzOMe-OMe 27). A mixture of 26 (0.2 g, 1.02 μMol), Im-COCCl$_3$, (345 mg, 1.53 μMol), DIEA (132 mg, 178 μL, 1.02 μMol), and DMAP (25 mg, 204 μMol) in EtOAc (5 mL) was stirred for 12 h at 60° C., over which time a precipitate formed. The reaction was cooled to room temperature, filtered, and washed with cold Et$_2$O. The off white solid was collected and dissolved in AcOH (5 mL). The mixture was then heated to 90° C. for 6 h. The solvent was then removed by rotoevaporation and the remaining white solid dried under high vacuum to provide 27 (210 mg, 72% yield). TLC (4:1 EtOAc/Hex) R$_f$ 0.4; $^1$H NMR (DMSO-d$_6$) 7.55 (s, 1H), 7.53 (s, 1H) 7.43 (s, 1H), 7.13 (s, 1H), 4.36 (s, 3H), 4.16 (s, 3H), 3.78 (s, 3H); $^{13}$C (DMSO-d$_6$) 166.4, 151.2, 143.8, 138.9, 136.9, 134.6, 128.3, 125.4, 125.3, 113.9, 105.1, 60.9, 51.7, 35.1; EI-MS m/e 286.107 (M$^+$ calcd for 286.107 C$_{14}$H$_{14}$N$_4$O$_3$).

7-methoxy-2-(1-methylimidazol-2-yl)benzimidazole-6-carboxylic acid (Im-HzOMe-OH 29). A mixture of 27 (200 mg, 699 μMol), MeOH (3 mL), and 1N NaOH (4 mL) was stirred at 35° C. for 3 h. The methanol was removed in vacuo and the mixture was taken to pH 2 using 1N HCl, upon which time a white precipitate formed. The mixture was poured into a 50 mL Falcon tube and spun down in a centrifuge (10 min×14,000 rpm). The tube was decanted, leaving a white solid that was dried under high vacuum to provide 29 (165 mg, 87% yield). TLC (3:2 EtOAc/Hex, 10% AcOH) R$_f$ 0.4; $^1$H NMR (DMSO-d$_6$) 7.58 (s, 1H), 7.55 (s, 1H) 7.46 (s, 1H), 7.16 (s, 1H), 4.33 (s, 3H), 4.16 (s, 3H); $^{13}$C (DMSO-d$_6$) 167.4, 151.0, 143.6, 138.6, 136.8, 135.2, 127.8, 125.7, 125.3, 115.1, 105.2, 61.0, 35.2; EI-MS m/e 272.260 (M$^+$ calcd for 272.260 C$_{13}$H$_{12}$N$_4$O$_3$).

Methyl 7-methoxy-2-(1-methyl-4-nitroimidazol-2-yl) benzimidazole-6-carboxylate (NO$_2$-Im-HzOMe-OMe 28). Diamine 26 (0.5 g, 2.54 mmol), NO$_2$-Im-OH (480 mg, 2.80 mmol), HBTU (1 g, 2.66 mmol), DIEA (362 mg, 488 μL, 2.80 mmol), and DMF (7 mL) were stirred for 2 days at room temperature. The mixture was then added to a 50 mL Falcon tube containing water (20 mL), resulting in a precipitate. The Falcon tube was centrifuged (10 min×14,000 rpm) and the mother liquor decanted, leaving a tan solid that was dried under high vac. The solid was then dissolved in AcOH (8 mL) and heated to 90° C. with stirring. It is noteworthy that the solid was not completely soluble in AcOH. The reaction was stirred for 6 hours and the precipitate that was present was filtered over a fine fritted funnel. The solid was washed with Et$_2$O and dried under high vacuum to provide 28 (481 mg, 57% Yield) as a powdery yellow solid. TLC (3:2 EtOAc/Hex) R$_f$ 0.5; $^1$H NMR (DMSO-d$_6$) 8.68 (s, 1H), 7.60 (d, J=8.4 Hz, 1H) 7.18 (d, J=8.4 Hz, 1H), 4.38 (s, 3H), 4.24 (s, 3H), 3.78 (s, 3H); $^{13}$C (DMSO-d$_6$); EI-MS m/e 331.092 (M$^+$ calcd for 331.092 C$_{14}$H$_{13}$N$_5$O$_5$).

Methyl 2-{4-[(tert-butoxy)carbonylamino]-1-methylimidazol-2-yl}-7-methoxybenzimidazole-6-carboxylate (Boc-Im-HzOMe-OMe 30). A mixture of 28 (400 mg, 1.21 mmol), DIEA (400 mg, 536 μL, 3.08 mmol), Pd/C (50 mg) and DMF (5 mL) was placed in a parr apparatus and hydrogenated (500 psi) for 1.5 h at ambient temperature. The mixture was removed from the parr apparatus and (Boc)$_2$O (396 mg, 1.82 mmol) was added. The mixture was then stirred for 8 h at 50° C. The solvent was removed in vacuo, followed by column chromatography of the brown residue (3:2 Hex/EtOAc) to provide 30 as a thin film. The thin film was treated with hexanes and then the solvent was removed by rotoevaporation, followed by drying under high vacuum to provide 30 as a white solid (228 mg, 47% Yield). TLC (3:2 EtOAc/Hex) $R_f$ 0.6; $^1$H NMR (DMSO-$d_6$) 9.55 (s, 1H), 7.75 (d, J=8.7 Hz, 1H) 7.60 (d, J=8.7 Hz, 1H), 7.21 (s, 1H) 4.27 (s, 3H), 3.81 (s, 3H), 3.70 (s, 3H), 1.44 (s, 9H); $^{13}$C (DMSO-$d_6$) 165.8, 151.0, 147.0, 142.1, 137.9, 137.0, 133.3, 132.4, 127.8, 117.3, 109.4, 107.2, 85.9, 61.7, 52.0, 33.5, 28.2; EI-MS m/e 401.170 ($M^+$ calcd for 401.170 $C_{14}H_{13}N_5O_5$).

2-{4-[(tert-butoxy)carbonylamino]-1-methylimidazol-2-yl}-7-methoxybenzimidazole-6-carboxylic acid (Boc-Im-HzOMe-OH 31). A mixture of 30 (200 mg, 498 μMol), 1N NaOH (2 mL) and MeOH (2 mL) was stirred at 30° C. for 4 h. The MeOH was removed by rotoevaporation and the pH carefully adjusted to pH=2 with 1N HCl. The precipitate was extracted with EtOAc (3×10 mL), the organics dried over sodium sulfate and removed by rotoevaporation to provide 31 (166 mg, 86% yield) as a fine white solid. TLC (3:2 EtOAc/Hex, 10% AcOH) $R_f$ 0.65; $^1$H NMR (DMSO-$d_6$) 9.55 (s, 1H), 7.77 (d, J=8.7 Hz, 1H) 7.63 (d, J=8.7 Hz, 1H), 7.23 (s, 1H) 4.24 (s, 3H), 3.77 (s, 3H), 1.44 (s, 9H); $^{13}$C (DMSO-$d_6$) 166.7, 150.8, 146.7, 142.0, 135.9, 137.0, 133.3, 132.4, 127.4, 117.3, 109.4, 107.3, 86.0, 61.8, 33.6, 28.2; EI-MS m/e 387.154 ($M^+$ calcd for 387.154 $C_{18}H_{21}N_5O_5$).

Example 2

Synthesis of Representative Polyamide Oligomers

A. Polyamide Oligomer Synthesis—Route A

Manual solid-phase methods on Kaiser's oxime resin (0.48 mmol/g) (Baird, E. E.; Dervan, P. B. *J. Am. Chem. Soc.*, 118: 6141-6146, 1996; Belitsky, J. M.; Nguyen, D. H.; Wurtz, N. R.; Dervan, P. B. *Bioorg. Med. Chem.*, 10: 2767-2774, 2002) was performed to prepare representative oligomers of the invention. For the synthesis of the imidazo[4,5-b]pyridine, hydroxy-benzimidazole and benzimidazole containing polyamides, the same protocol was applied successfully as shown in Scheme 5. The building blocks employed for the stepwise oligomer elongation procedure were Boc-N-methyl pyrrole (Boc-Py-OBt, 34), Boc-N-methyl imidazole (Boc-Im-OH, 35), Boc-N-methyl methoxypyrrole (Boc-Op-OH, 36) monomers, N-methyl imidazole (Im-OH, 37) cap and α-Fmoc-γ-Boc-(R)-2,4-diaminobutyric acid (α-Fmoc-γ-Boc-(R)-DABA, 38). Compounds 9, 32, and 33 were coupled in NMP/DIEA for 3 h at r.t. after activation with HBTU. Deprotection was achieved with 20% TFA/CH$_2$Cl$_2$. Following the general protocol summarized in Scheme 5, the synthesis of hairpin polyamides containing the fused six-membered heterocycles was carried out in 15 steps.

Cleavage from the resin and removal of the Fmoc group of the DABA turn was achieved by treatment with methylamine/CH$_2$Cl$_2$ (12 h, 37° C.). Following filtration of the resin, the crude mixtures were purified by reversed-phase HPLC to yield polyamides ImPyIpPy-(R)$^H$n$^{Ny}$-PyPyPyPy-CONHMe (oligomer A), Im-PyImPy-(R)$^H$2$^N$γ-PyPyPyPy-CONHMe (oligomer N), ImPyHzPy-(R)$^H$2$^N$γ-PyPyPyPy-CONHMe (oligomer M), ImPyIpPy-(R)$^H$2$^N$γ-PyPyPyPy-CONHMe (oligomer O), ImPyBiPy-(R)$^H$2$^N$γ-PyPyPyPyCONHMe (oligomer C), and ImPyPyPy-(R)$^H$2$^N$γ-PyPyPyPy-CONHMe (oligomer P). Subsequently, both O-methyl protected polyamides oligomers M and O were O-demethylated under identical conditions using ethanethiol/NaH protocol (80° C., 30 min) and purified by reversed-phase HPLC to provide ImPyHzPy-(R)$^H$2$^N$γ-PyPyPyPy-CONHMe (oligomer B) and ImPyHpPy-(R)$^H$2$^N$γ-PyPyPyPy-CONHMe (oligomer Q).

Scheme 5.
Synthesis Route A of Polyamide Oligomers

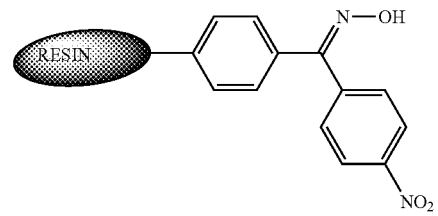

(a) 34, DIEA, NPM
(b) 20% TFA/CH$_2$Cl$_2$
(c) 34, DIEA, NMP
(d) 20% TFA/CH$_2$Cl$_2$
(e) 34, DIEA, NMP
(f) 20% TFA/CH$_2$Cl$_2$
(g) 34, DIEA, NMP
(h) 20% TFA/CH$_2$Cl$_2$
(i) 38, HBTU, DIEA, NMP
(j) 20% TFA/CH$_2$Cl$_2$
(k) 9 (for oligomer A where X = N)
    33 (for oligomer C where X = CH),
    and 32 (for oligomer M where X = COCH$_3$),
    DIEA, NMP
(l) 20% TFA/CH$_2$Cl$_2$
(m) 11, HBTU, DIEA, NMP
(n) 20% TFA/CH$_2$Cl$_2$
(o) 37, HBTU, DIEA, NMP -continued
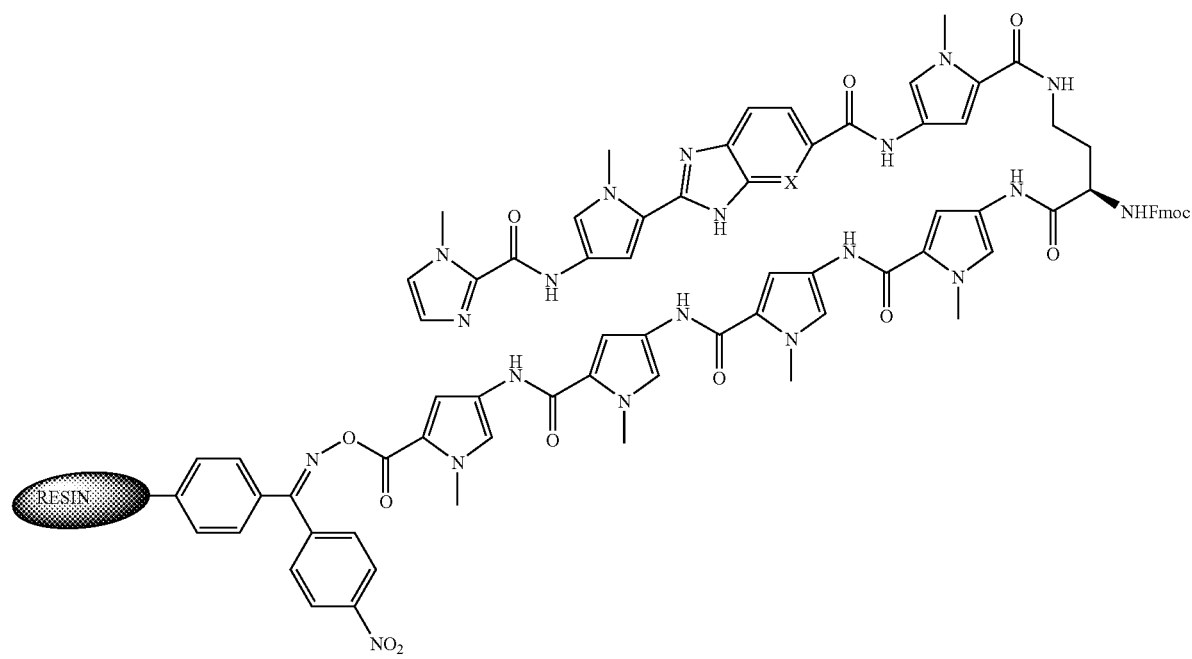
2.0 M CH$_3$NH$_2$/THF, CH$_2$Cl$_2$
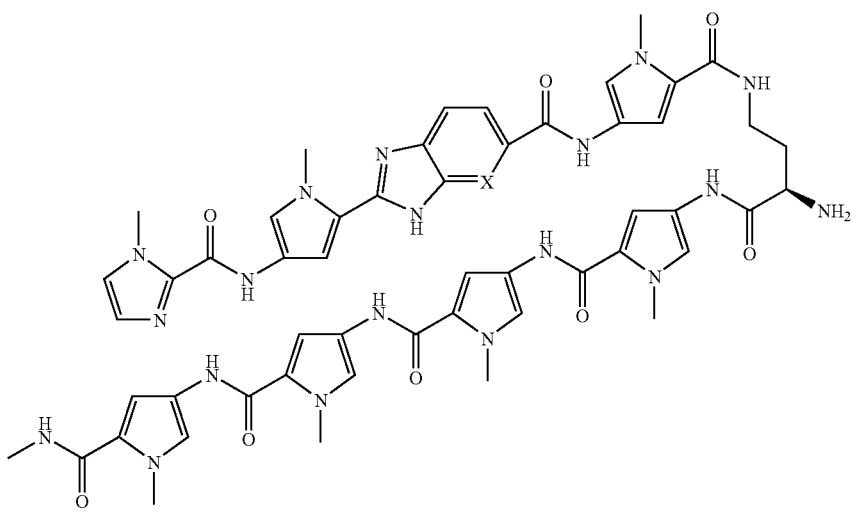
Oligomer A: X = N
Oligomer C: X = CH
Oligomer M: X = COCH$_3$
Oligomer B: X = COH
EtSH, NaH, DMF
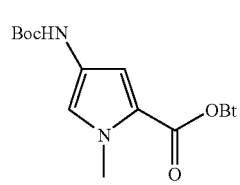
34
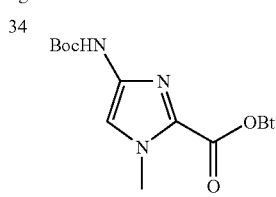
35
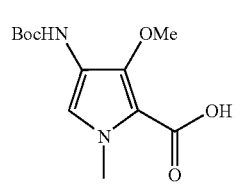
36
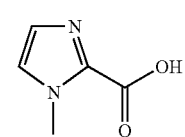
37

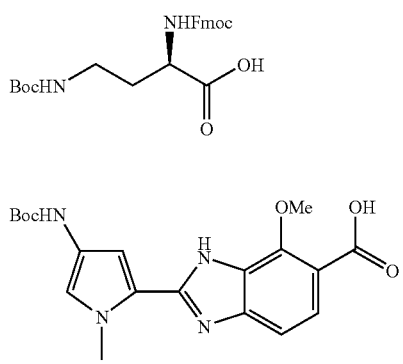

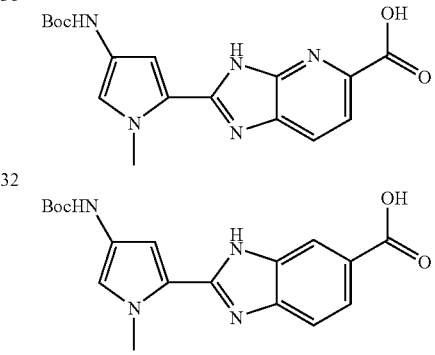

Polyamide Synthesis. Polyamide oligomers N, Q, and P were synthesized in a stepwise fashion from 0.48 mmol/g oxime resin by manual solid-phase methods using Boc-protected amino acid building blocks as reported earlier. (Baird, E. E.; Dervan, P. B. J. Am. Chem. Soc., 118: 6141-6146, 1996.) The incorporation of the imidazo[4,5-b]pyridine, hydroxy-benzimidazole and benzimidazole Boc-protected building blocks, to synthesize polyamide oligomers A, B, and C was achieved under identical conditions. Activation of 9, 32, and 33 was achieved with HBTU (1 eq. in NMP, DIEA) for 10 min and coupling was realized for 3 h at r.t. Deprotection of the immobilized polyamides-containing building blocks was successful using 20% TFA in $CH_2Cl_2$ for 25 min.

Extinction coefficients were calculated based on $\epsilon=8690$ cm L mol$^{-1}$ per ring at 310 nm for the polyamide oligomers N, Q, and P. The extinction coefficient for polyamide oligomers A, B, and C was determined as 28 500 cm L mol$^{-1}$ (at 330 nm), 33 914 cm L mol$^{-1}$ (at 318 nm), and 40 081 cm L mol$^{-1}$ (at 326 nm), respectively.

Procedure for $MeNH_2$ Cleavage from the Resin. After completion of the synthesis of the polyamides the resin was filtered off the reaction and washed with DMF, DCM, MeOH, $Et_2O$, and dried in vacuo. (J. M. Belitsky, D. H. Nguyen, N. R. Wurtz, P. B. Dervan, Bioorg. Med. Chem., 10: 2767-2774, 2002.) A sample of the resin (150 mg) was swollen in DCM (3 mL) and treated with $MeNH_2$ (2M in THF, 3 mL) under periodic agitation at 37° C. for 16 h. The resin was then removed by filtration, washed with DCM and DMF, and concentrated in vacuo. After diluting with 20% MeCN/0.1% TFA the crude mixture was purified by preparative reversed-phase HPLC to yield the pure polyamide oligomers.

ImPyIpPy-(R)$^{H_2N}$ γ-PyPyPyPy-CONHMe (oligomer A). Starting with 100 mg of resin the title compound was synthesized. It was recovered upon lyophilization of the appropriate fractions as an orange powder (0.4 mg). UV ($H_2O$): $\gamma_{max}$ 330, 248. MALDI-TOF-MS: calcd. for $C_{52}H_{57}N_{20}O_8$, 1090.1; found, 1090.1, 1110.8 (M+Na).

ImPyImPy-(R)$^{H_2N}$ γ-PyPyPyPy-CONHMe (oligomer N). Starting with 150 mg of resin the title compound was synthesized. It was recovered upon lyophilization of the appropriate fractions as a white powder (0.5 mg). UV ($H_2O$): $\gamma_{max}$ 314, 246. MALDI-TOF-MS: calcd. for $C_{51}H_{59}N_{20}O_9$, 1096.1; found, 1096.1, 1117.1 (M+Na).

ImPyBiPy-(R)$^{H_2N}$ γ-PyPyPyPy-CONHMe (oligomer C). Starting with 150 mg of resin the title compound was synthesized. It was recovered upon lyophilization of the appropriate fractions as a beige powder (0.6 mg). UV ($H_2O$): $\gamma_{max}$ 326, 246. MALDI-TOF-MS: calcd. for $C_{53}H_{58}N_{19}O_8$, 1089.1; found, 1089.1.

ImPyPyPy-(R)$^{H_2N}$ γ-PyPyPyPy-CONHMe (oligomer P). Starting with 150 mg of resin the title compound was synthesized. It was recovered upon lyophilization of the appropriate fractions as a white powder (0.7 mg). UV ($H_2O$): $\gamma_{max}$ 316, 246. MALDI-TOF-MS: calcd. for $C_{52}H_{59}N_{19}O_9$, 1094.1; found, 1094.2.

ImPyHzPy-(R)$^{H_2N}$ γ-PyPyPyPy-CONHMe (oligomer M). Starting With 200 mg of resin the title compound was synthesized. It was recovered upon lyophilization of the appropriate fractions as a white powder (1.6 mg). UV ($H_2O$): $\gamma_{max}$ 320, 246. MALDI-TOF-MS: calcd. for $C_{54}H_{60}N_{19}O_9$, 1119.1; found, 1119.2, 1142.17 (M+Na).

ImPyIpPy-(R)$^{H_2N}$ γ-PyPyPyPy-CONHMe (oligomer O). Starting with 200 mg of resin the title compound was synthesized. It was recovered upon lyophilization of the appropriate fractions as a white powder (0.8 mg). UV ($H_2O$): $\gamma_{max}$ 318, 245. MALDI-TOF-MS: calcd. for $C_{53}H_{62}N_{19}O_{10}$, 1125.1, found, 1125.6.

Deprotection of the O-Methyl-Protected Polyamides. Following a previously reported procedure, to a slurry of NaH (80 mg, 60% in mineral oil) in 0.5 mL DMF was added ethanethiol (0.32 mL), and the mixture was heated to 80° C. for 5 min. (Kielkopf, C. L.; Baird, E. E.; Dervan, P. B.; Rees, D. C., Nature Struct. Biol., 5: 104-109, 1998.) The polyamide (0.4 μmol) was dissolved in DMF (0.25 mL), added to the ethanethiolate solution and the mixture was heated to 80° C. for 30 min in a sealed tube under periodic agitation. After cooling to 0° C., glacial acetic acid (3 mL) was added and all volatiles removed in vacuo. The residue was dissolved in $CH_3CN$ (0.5 mL) and 0.1% TFA (2 mL) and purified by preparative reverse-phase HPLC to yield the pure polyamides.

ImPyHzPy-(R)$^{H_2N}$ γ-PyPyPyPy-CONHMe (oligomer B). The title compound was recovered upon lyophilization of the appropriate fractions as a yellow powder (0.4 mg). UV ($H_2O$): $\gamma_{max}$ 318, 254. MALDI-TOF-MS: calcd. for $C_{53}H_{58}N_{19}O_9$, 1105.1; found, 1105.1.

ImPyHpPy-(R)$^{H_2N}$ γ-PyPyPyPy-CONHMe (oligomer Q). The title compound was recovered upon lyophilization of the appropriate fractions as a white powder (0.1 mg). UV ($H_2O$): $\gamma_{max}$ 316, 244. MALDI-TOF-MS: calcd. for $C_{52}H_{60}N_{19}O_{10}$, 1111.1; found, 1111.7, 1133.7 (M+Na).

B. Polyamide Oligomer Synthesis—Route B

Polyamides oligomers R and S, and the O-protected derivative T were synthesized by solid-phase methods on Kaiser's oxime resin (0.48 mmol g$^{-1}$) in a stepwise manner from Boc-N-methyl pyrrole (Boc-Py-OBt, 34), Boc-N-methyl imidazole (Boc-Im-OH, 35), Boc-N-methyl methoxypyrrole (Boc-Op-OH, 36) monomers, α-Fmoc-γ-Boc-(R)-2, 4-diaminobutyric acid (α-Fmoc-γ-Boc-(R)-DABA, 38), and N-methyl imidazole dimer (ImIm-OH, 39) in 16 steps. Similarly, benzimidazoles 23a-c could be successfully used as building blocks for the stepwise polyamide growth furnishing resin-bound benzimidazole-containing polyamide oligomers D, E, and the O-protected derivative U in 13 steps (Scheme 6). The same reaction conditions proved to be suitable for peptide coupling and amine deprotection of benzimidazole monomers 23a-c and the standard building blocks 34-39: Benzimidazoles 23a-c were coupled in DIEA/NMP after activation with HBTU and (when resin-bound) deprotected with 20% TFA/CH$_2$Cl$_2$ (23c) or 50% TFA/CH$_2$Cl$_2$ (23a, b). However, due to the moderate efficiency of the Boc-Py-OBt to imidazole amine coupling, it was found advantageous in terms of the overall polyamide recovery to employ building block 25 instead of 23a for the synthesis of polyamide oligomer E. To liberate the resin-bound compounds and concomitantly remove the Fmoc group of the DABA turn, a sample of each polyamide-loaded polymer support was treated with methylamine in CH$_2$Cl$_2$/THF (14 h, 37° C.). The crude polyamides were isolated and purified by preparatory reverse-phase HPLC to yield ImPyPy-(R)$^{H_2N}$ γ-ImPyPyPy-CONHMe (oligomer R), ImImPyPy-(R)$^{H_2N}$ γ-ImPyBiPy-CONHMe (oligomer D), ImImPyPy-(R)$^{H_2N}$ γ-PyImPyPy-CONHMe (oligomer S), ImImPyPy-(R)$^{H_2N}$ γ-PyImBiPy-CONHMe (oligomer E), ImImPyPy-(R)$^{H_2N}$ γ-Im-OpPyPy-CONHMe (oligomer T), ImImPyPy-(R)$^{H_2N}$ γ-ImOpBiPy-CONHMe (oligomer U). O-Methyl protected polyamides T and U were O-demethylated with sodium thiophenoxide/DMF (85° C., 2 h) and purified by preparatory reversed-phase HPLC to yield ImImPyPy-(R)$^{H_2N}$ γ-ImHpPyPy-CONHMe (oligomer V) and ImImPyPy-(R)$^{H_2N}$ γ-ImHpBiPy-CONHMe (oligomer F). The synthetic protocol for the solid-phase synthesis of benzimi-dazole-containing polyamide oligomers D, E, and F is illustrated in Scheme 6.

Scheme 6.
Synthesis Route B of Polyamide Oligomers

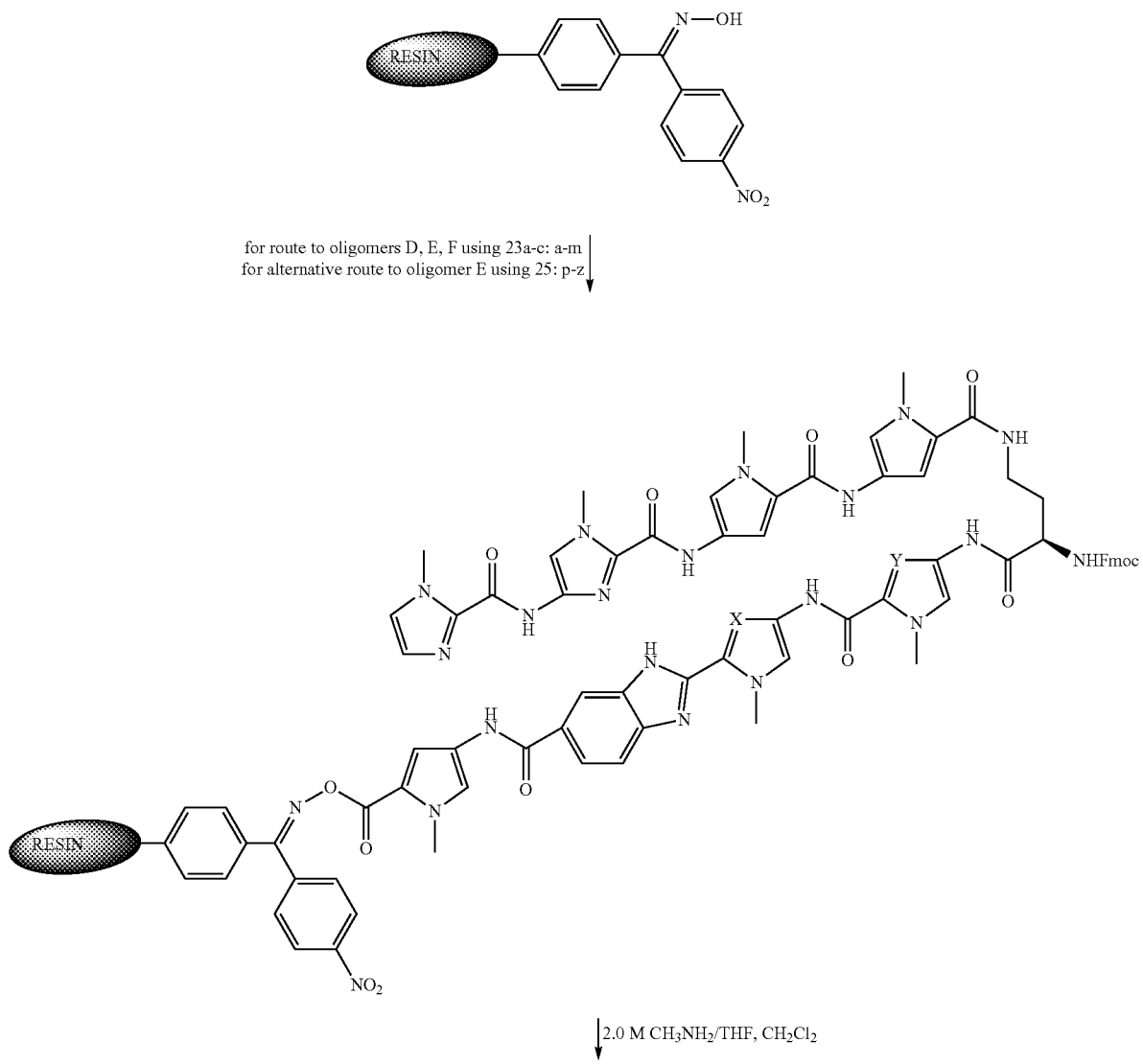

-continued
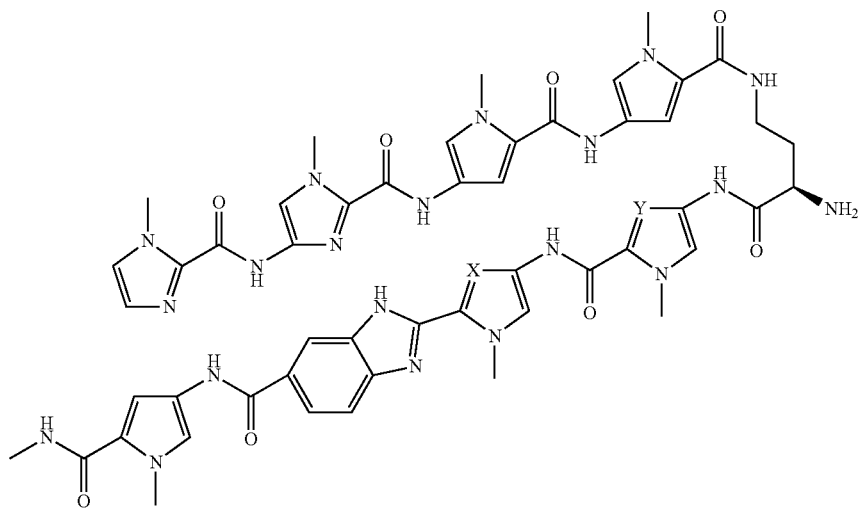
Oligomer D: X = CH, Y = N
Oligomer E: X = N, Y = CH
PhSNa, DMF  Oligomer U: X = COCH₃, Y = N
Oligomer F: X = COH, Y = N
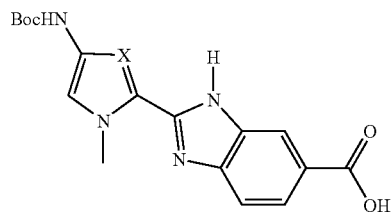
23a: X = N
23b: X = COCH₃
23c: X = CH
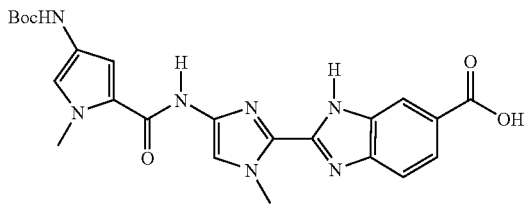
25
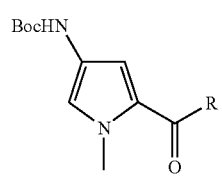
34a: R = OBt
34b: R = OH
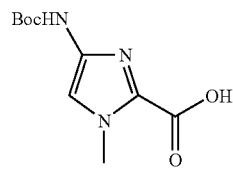
35
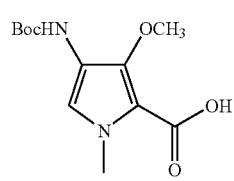
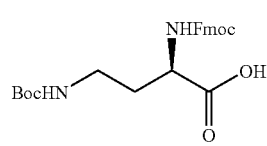
36
38

-continued

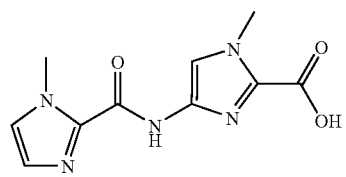

(a) 34a, DIEA, NMP; (b) 20% TFA/CH₂Cl₂; (c) for X = N: 23a, HBTU, DIEA, NMP; for X = COCH₃: 23b, HBTU, DIEA, NMP; for X = CH: 23c, HBTU, DIEA, NMP; (d) for X = CH: 20% TFA/CH₂Cl₂; for X = N, COCH₃: 50% TFA/CH₂Cl₂; (e) X = COCH₃, CH: 35, HBTU, DIEA, NMP; for X = N: 34b, DCC, DMAP, CH₂Cl₂; (f) for Y = CH: 20% TFA/CH₂Cl₂; for Y = N: 50% TFA/CH₂Cl₂; (g) 38, HBTU, DIEA, NMP; (h) 20% TFA/CH₂Cl₂; (i) 34a, DIEA, NMP; (j) 20% TFA/CH₂Cl₂; (k) 34a, DIEA, NMP; (l) 20% TFA/CH₂Cl₂; (m) 39, DCC, HOBt, DIEA, NMP; (p) 34a, DIEA, NMP; (q) 20% TFA/CH₂Cl₂; (r) 25, HBTU, DIEA, NMP; (s) 20% TFA/CH₂Cl₂; (t) 38, HBTU, DIEA, NMP; (u) 20% TFA/CH₂Cl₂; (v) 34a, DIEA, NMP; (w) 20% TFA/CH₂Cl₂; (x) 34a, DIEA, NMP; (y) 20% TFA/CH₂Cl₂; (z) 39, DCC, HOBt, DIEA, NMP.

Polyamide oligomers D, E, F, R, S, and V were generated by manual solid-phase synthesis on oxime resin according to recently reported protocols using Boc-protected amino acid building blocks. The synthesis of polyamide ImImPyPy-(R)$^{H_2N}$ γ-mPyPyPyCONHMe Oligomer R has been previously described. (N. R. Wurtz, J. L. Pomerantz, D. Baltimore, P. B. Dervan, *Biochemistry*, 41: 7604-7609, 2002.) For the coupling of benzimidazole building blocks Boc protected amino acids 23a-c and 25 were activated with HBTU (1 equiv in DIEA, NMP) for 15 min and subsequently coupled for 4 h at ambient temperature. Resultant resin-bound benzimidazoles were deprotected using 20% TFA in CH₂Cl₂ for 25 min (for resin-bound 23c and 25) or 50% TFA in CH₂Cl₂ for 25 min (for resin-bound 23a,b).

General procedure for MeNH₂ cleavage: A sample of the derivatized resin (100 mg) was suspended in CH₂CL₂ (2 mL) to which was added methylamine in THF (2 mL, 2.0 m). The mixture was agitated at 37 8 C for 14 h. J. M. Belitsky, D. H. Nguyen, N. R. Wurtz, P. B. Dervan, *Bioorg. Med. Chem.*, 10: 2767-2774, 2002. The resin was filtered, rinsed with CH₂Cl₂ and DMF, the eluant concentrated in vacuo, and the residue purified by prep. reversed-phase HPLC to yield the desired polyamides.

ImImPyPy-(R)$^{H_2N}$ γ-ImPyBiPyCONHMe (oligomer D): The title compound was recovered upon lyophilization of the appropriate fractions as a yellow powder. MALDI-TOF-MS: calcd for $C_{51}H_{55}N_{21}O_8$: 1090.1; found: 1090.6.

ImImPyPy-(R)$^{H_2N}$ γ-PyImPyPyCONHMe (oligomer S): The title compound was recovered upon lyophilization of the appropriate fractions as a white powder. MALDI-TOF-MS: calcd for $C_{49}H_{56}N_{22}O_9$: 1097.1; found: 1097.6.

ImImPyPy-(R)$^{H_2N}$ γ-PyImBiPyCONHMe (oligomer E): The title compound was recovered upon lyophilization of the appropriate fractions as a yellow powder. MALDI-TOF-MS: calcd for $C_{50}H_{54}N_{22}O_8$: 1091.8; found: 1091.1.

ImImPyPy-(R)$^{H_2N}$ γ-ImOpPyPyCONHMe (oligomer T): The title compound was recovered upon lyophilization of the appropriate fractions as a beige powder. MALDI-TOF-MS: calcd for $C_{51}H_{59}N_{21}O_{10}$: 1126.2; found: 1126.7.

ImImPyPy-(R)$^{H_2N}$ γ-ImOpBiPyCONHMe (oligomer U): The title compound was recovered upon lyophilization of the appropriate fractions as a yellow powder. MALDI-TOF-MS: calcd for $C_{52}H_{57}N_{21}O_9$: 1120.2; found: 1120.7.

O-Demethylation of polyamide oligomers T and V: According to the previously reported protocol polyamides were treated with sodium thiophenoxide in DMF at 85° C. for 2 h and subsequently purified by prep. reversed-phase HPLC to yield the desired demethylated polyamides. (C. Melander, D. M. Herman, P. B. Dervan, *Chem. Eur. J.*, 6: 4487-4497, 2000.)

ImImPyPy-(R)$^{H_2N}$ γ-ImHpPyPyCONHMe (oligomer V): The title compound was recovered upon lyophilization of the appropriate fractions as a beige powder. MALDI-TOF-MS: calcd for $C_{50}H_{57}N_{21}O_{10}$: 1112.1; found: 1113.1.

ImImPyPy-(R)$^{H_2N}$ γ-ImHpBiPyCONHMe (oligomer F): The title compound was recovered upon lyophilization of the appropriate fractions as a yellow powder. MALDI-TOF-MS: calcd for $C_{51}H_{55}N_{21}O_9$: 1106.1; found: 1106.5.

C. Polyamide Oligomer Synthesis—Route C

Polyamide oligomers G-L were synthesized in stepwise fashion on β-Pam resin following manual solid phase methods. The Boc-protected amino acids utilized for polyamide synthesis were Boc-Py-OBt (34), Boc-Im-OH (35), Im-COCCl₃, Boc-γ-OH (40), Boc-Im-Bi-OH (23), Boc-Py-HzOMe-OH (41), Im-HzOMe-OH (29) and Boc-Im-HzOMe-OH (31) (Scheme 7). Couplings were realized using pre-activated monomers or HBTU activation in a DIEA and DMF mixture. Coupling times ran from 3-24 h at 25-40° C. Deprotection of the growing polyamide was accomplished using 80% TFA/DCM. Polyamides were cleaved from the resin by treatment with dimethylaminopropylamine (Dp) neat at 80° C. for 2 h, and purified by preparatory reverse phase HPLC. Deprotection of the methoxy-protected polyamides was done using a mix of thiophenoxide in DMF at 80° C., to provide the free hydroxy derivatives after a second HPLC purification: Im-Im-Hz-Py-γ-Im-Py-Py-Py-β-Dp (oligomer G), Im-Im-Py-Py-γ-Im-Hz-Py-Py-β-Dp (oligomer J), Im-Hz-Py-Py-γ-Im-Hz-Py-Py-β-Dp (oligomer H), Im-Py-Hz-Py-γ-Im-Py-Hz-Py-β-Dp (oligomer K), Im-Im-Hz-Py-γ-Im-Bi-Py-Py-β-Dp (oligomer I) and Im-Im-Bi-Py-γ-Im-Hz-Py-Py-β-Dp (oligomer L).

Polyamide oligomers were synthesized from Boc-β-alanine-Pam resin (50 mg, 0.59 mmol/g) and purified by preparatory HPLC according to published manual solid phase protocols. Baird, E. E.; Dervan, P. B., *J. Am. Chem. Soc.*, 118: 6141-6146, 1996.

Im-Im-Hz-Py-γ-Im-Py-Py-Py-β-Dp (oligomer G): (Boc-Im-HzOMe-OH) (34 mg, 88.5 μmol) was incorporated by activation with HBTU (32 mg, 84 μmol), DIEA (23 mg, 31 μl, 177 μmol) and DMF (250 μl). The mixture was allowed to stand for 15 min at room temperature and then added to the reaction vessel containing H₂N-Py-γ-Im-Py-Py-Py-β-Pam resin. Coupling was allowed to proceed for 12 h at room temperature. After Boc-deprotection, the terminal imidazole residue was incorporated using Im-COCCl₃. Im-COCCl₃ (67 mg, 295 μmol), DIEA (23 mg, 31 μl, 177 μmol) and DMF (400 μl) were added to the reaction vessel containing H$_2$N-Im-HzOMe-Py-γ-Im-Py-Py-Py-β-Pam resin. Coupling was allowed to proceed for 2 h at 37° C., and determined complete by analytical HPLC. The resin-bound polyamide was then washed with DCM and subjected to the cleavage, O-methyl deprotection and purification protocol described below to provide Im-Im-Hz-Py-γ-Im-Py-Py-Py-β-Dp (oligomer G) (1.1 mg, 3.1% recovery) as a fine white powder under lyophilization of the appropriate fractions. MALDI-TOF-MS (monoisotopic), 1233.56 (M+H calcd for 1233.56 C$_{58}$H$_{69}$N$_{22}$O$_{10}$).

Im-Im-Py-Py-γ-Im-Hz-Py-Py-β-Dp (oligomer J): (Boc-Im-HzOMe-OH) was incorporated as described for 26. The polyamide was cleaved from resin and treated as described in the deprotection protocol below to provide (oligomer J) (0.9 mg, 2.5% recovery) as a fine white powder under lyophilization of the appropriate fractions. MALDI-TOF-MS (monoisotopic), 1233.55 (M+H calcd for 1233.56 C$_{58}$H$_{69}$N$_{22}$O$_{10}$).

Im-Hz-Py-Py-γ-Im-Hz-Py-Py-β-Dp (oligomer H): (Im-HzOMe-OH) (25 mg, 88.5 μmol) was incorporated by activation with HBTU (32 mg, 84 μmol), DIEA (23 mg, 31 μl, 177 μmol) and DMF (250 μl). The mixture was allowed to stand for 15 min at room temperature and then added to the reaction vessel containing H$_2$N-Py-Py-γ-Im-Hz-Py-Py-β-Pam resin. Coupling was allowed to proceed for 12 h at room temperature. The resin-bound polyamide was then washed with DCM and treated as described in the deprotection protocol below to provide Im-Hz-Py-Py-γ-Im-Hz-Py-Py-β-Dp (oligomer H) (0.7 mg, 1.9% recovery) as a fine white powder under lyophilization of the appropriate fractions. MALDI-TOF-MS (monoisotopic), 1242.56 (M+H calcd for 1242.55 C$_{60}$H$_{68}$N$_{21}$O$_{10}$).

Im-Py-Hz-Py-γ-Im-Py-Hz-Py-β-Dp (oligomer K): (Boc-Py-HzOMe-OH) (34 mg, 88.5 μmol) was incorporated by activation with HBTU (32 mg, 84 μmol), DIEA (23 mg, 31 μl, 177 μmol) and DMF (250 μl). The mixture was allowed to stand for 15 min at room temperature and then added to the reaction vessel containing H$_2$N-Py-β-Pam resin. Coupling was allowed to proceed for 12 h at room temperature. After Boc-deprotection, the additional Im, γ, and Py units were incorporated as previously described. The second Boc-Py-HzOMe-OH unit was activated as described above and added to the reaction vessel containing H$_2$N-Py-γ-Im-Py-Hz-Py-β-Pam resin. Coupling was allowed to proceed for 12 h at room temperature. After Boc-deprotection, the terminal imidazole residue was added as described for 26. The resin-bound polyamide was then washed with DCM and treated as described in the deprotection protocol below to provide Im-Py-Hz-Py-γ-Im-Py-Hz-Py-β-Dp (oligomer K) (1.1 mg, 3.0% recovery) as a fine white powder under lyophilization of the appropriate fractions. MALDI-TOF-MS (monoisotopic), 1242.55 (M+H calcd for 1242.55 C$_{60}$H$_{68}$N$_{21}$O$_{10}$).

Im-Im-Py-γ-Im-Bi-Py-Py-β-Dp (oligomer I): (Boc-Im-Bi-OH) (32 mg, 88.5 μmol) was incorporated by activation with HBTU (32 mg, 84 μmol), DIEA (23 mg, 31 μl, 177 μmol) and DMF (250 μl). The mixture was allowed to stand for 15 min at room temperature and then added to the reaction vessel containing H$_2$N-Py-Py-β-Pam resin. Coupling was allowed to proceed for 12 h at room temperature. After Boc-deprotection, the additional Im, γ, and Py units were incorporated as previously described. The Boc-Im-HzOMe-OH residue and the terminal imidazole residue were incorporated as described for 31. The resin-bound polyamide was then washed with DCM and treated as described in the deprotection protocol below to provide Im-Im-Hz-Py-γ-Im-Bi-Py-Py-β-Dp (oligomer I) (1.1 mg, 3.0% recovery) as a fine white powder under lyophilization of the appropriate fractions. MALDI-TOF-MS (monoisotopic), 1226.55 (M+H calcd for 1226.54 C$_{59}$H$_{66}$N$_{22}$O$_9$).

Im-Im-Bi-Py-γ-Im-Hz-Py-Py-β-Dp (oligomer L): (Boc-Im-HzOMe-OH) and (Boc-Im-Bi-OH) were incorporated as described in oligomers G and I. The terminal imidzole residue was incorporated as described in 31. Upon completion of the synthesis, the resin-bound polyamide was then washed with DCM and treated as described in the deprotection protocol below to provide Im-Im-Bi-Py-γ-Im-Hz-Py-Py-β-Dp (oligomer L) (1.3 mg, 3.5% recovery) as a fine white powder under lyophilization of the appropriate fractions. MALDI-TOF-MS (monoisotopic), 1226.54 (M+H calcd for 1226.54 C$_{59}$H$_{66}$N$_{22}$O$_9$).

Deprotection of the O-Methyl-Protected Polyamides. All of the above polyamide oligomers were cleaved from resin, purified, deprotected and subject to further purification using the following general procedure. Upon completion of solid phase synthesis, Dp (500 □L) was added to the synthesis vessel containing the resin (50 mg). The mixture was allowed to stand for 2 h at 85° C. with occasional agitation. The resin was then filtered and the solution diluted to 8 mL using 0.1% TFA. The sample was purified by reversed phase HPLC and lyophilized to provide polyamide oligomers containing the O-methyl protected hydroxybenzimidazole unit (-HzOMe-) as a dry solid. The polyamide oligomers were then dissolved in DMF (200 μl) and added to a suspension of sodium hydride (40 mg, 60% oil dispersion) and thiophenol (200 μl) in DMF (400 μl) that was pre-heated for 5 min at 85° C. The mixture was heated for 2 h at 85° C. The mixture was then cooled to 0° C. and 20% TFA (7.0 mL) was added. The aqueous layer was washed three times with diethyl ether (8 mL) and then diluted to a total volume of 9.5 mL using 0.1% TFA. The mixture was then purified by reverse-phase HPLC to give the deprotected Hz-containing polyamide oligomers.

Scheme 7.
Synthesis Route C of Polyamide Oligomers (35)

Boc-Py-OBt        Boc-Im-OH

-continued

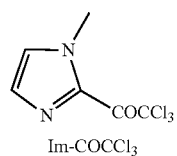
Im-COCCl₃

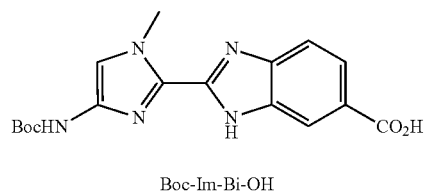
Boc-Im-Bi-OH

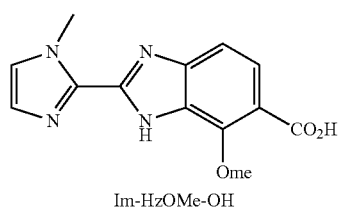
Im-HzOMe-OH

(40)
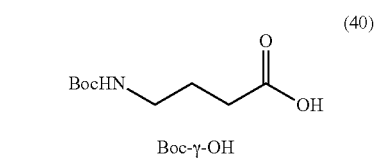
Boc-γ-OH

(41)
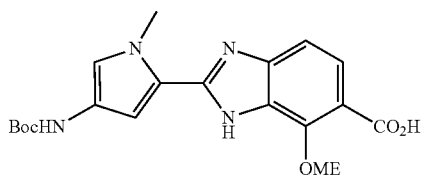
Boc-Py-HzOMe-OH

(31)
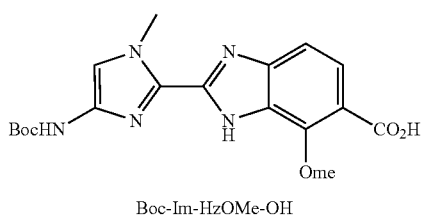
Boc-Im-HzOMe-OH

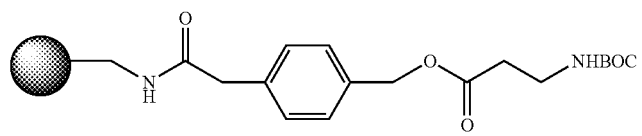

(i) 80% TFA/DCM; (ii) Boc-Py-OBt, DIEA, DMF; (iii) Ac₂O, DIEA, DMF; (iv) Repeat i-iii x2; (v) 80% TFA/DCM; (vi) Boc-Im-OH, HBTU, DIEA, DMF; (vii) Ac₂O, DIEA, DMF; (viii) 80% TFA/DCM; (ix) Boc-γ-OH, HBTU, DIEA, DMF; (x) Ac₂O, DIEA, DMF; (xi) 80% TFA/DCM; (xii) Boc-Py-OBt, DIEA, DMF; (xiii) Ac₂O, DIEA, DMF; (xiv) 80% TFA/DCM; (xv) Boc-Im-HzOMe-OH, HBTU, DIEA, DMF; (xvi) Ac₂O, DIEA, DMF; (xvii) 80% TFA/DCM; (xviii) ImCOCl₃, DIEA, DMF

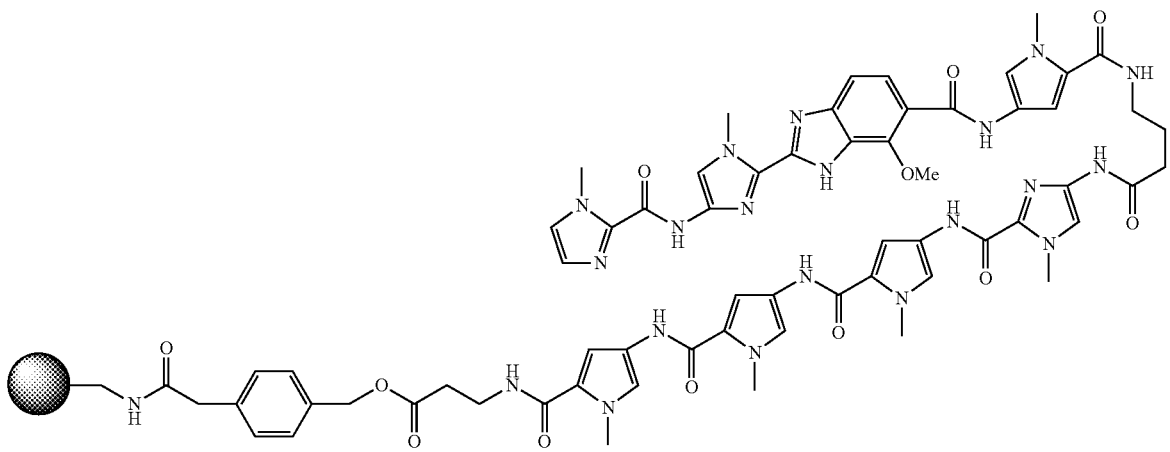
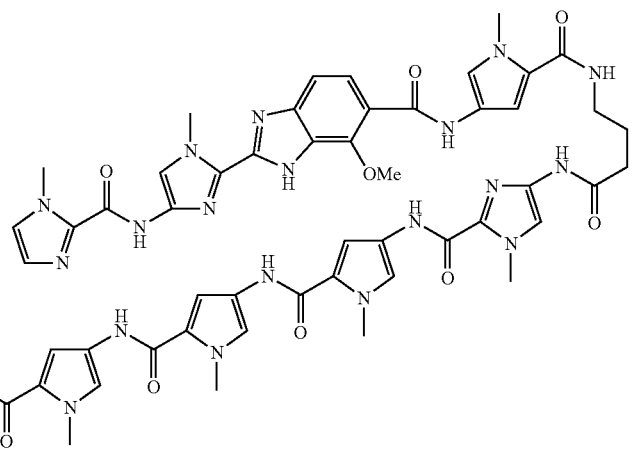

(xix) dimethylaminopropylamine (Dp), 80° C. 2 h; (xx) prep. HPLC; (xxi) thiophenol, NaH, DMF, 80° C. 2 h; (xxii) prep. HPLC

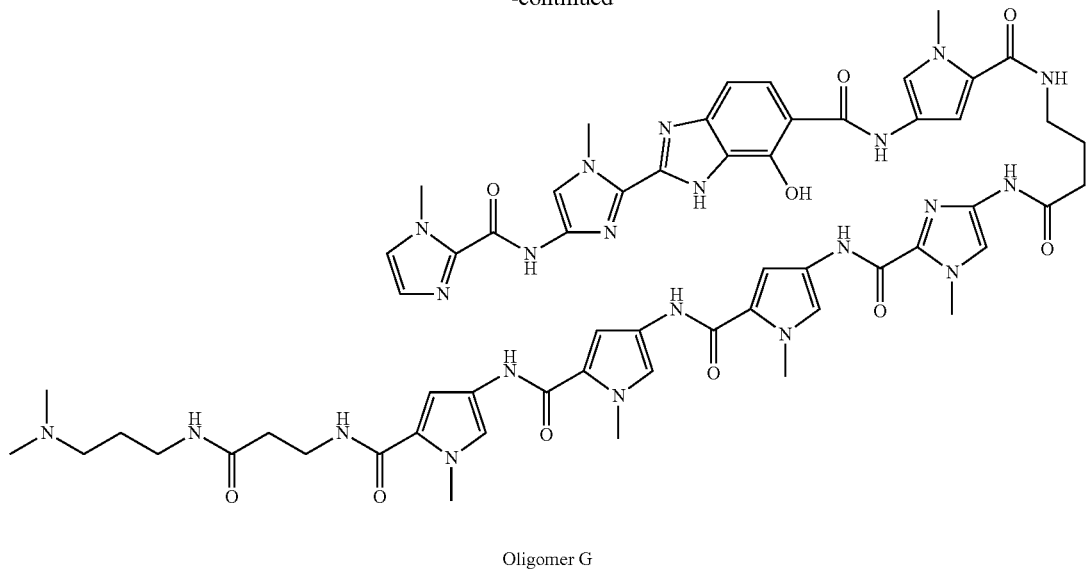

Oligomer G

Example 3

Figure 2:
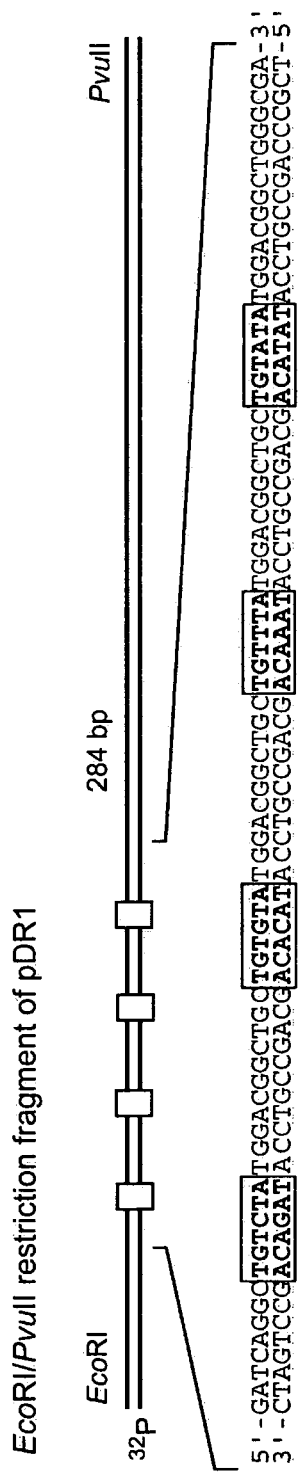
FIG. 2 illustrates the complete sequences of the EcoRI/PvuII restriction fragment derived from plasmid pDR1 (SEQ ID NO: 1). The four designed 6-base pair binding sites that were analyzed in quantitative footprint titrations are shown in bold and surrounded by a box.
Figure 3:
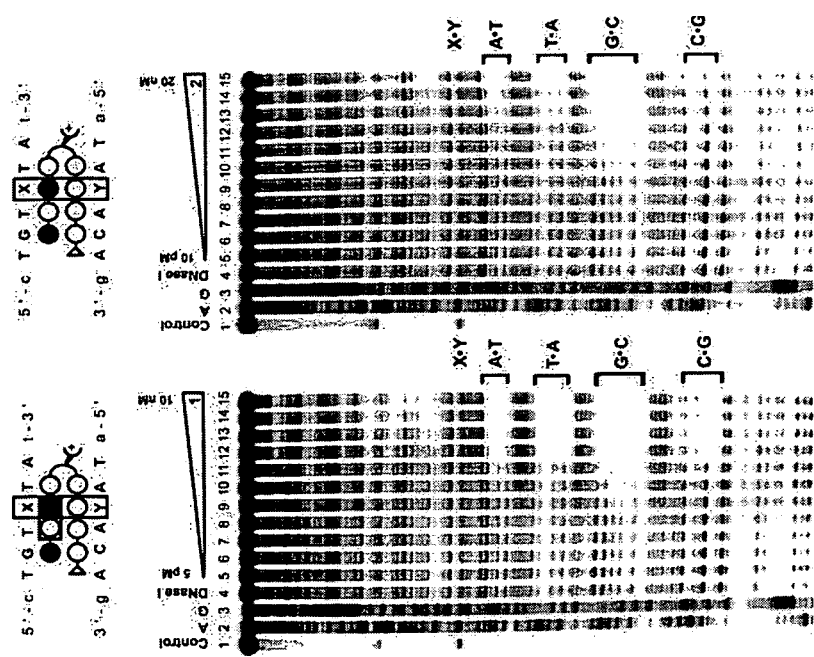
FIG. 3 illustrates the quantitative DNase I footprint titration experiments on the 3'-$^{32}$P-labeled 284-bp EcoRI/PvuII restriction fragment from plasmid pDR1. Left: polyamide oligomer A: lane 1, intact DNA; lane 2, A-specific reaction; lane 3, G-specific reaction; lane 4, DNase I standard; lane 5-15, 5, 10, 20, 50, 100, 200, 500 pM and 1, 2, 5, 10 nM polyamide, respectively. Right: polyamide oligomer B: lane 1, intact DNA; lane 2, A-specific reaction; lane 3, G-specific reaction; lane 4, DNase I standard; lane 5-15, 10, 20, 50, 100, 200, 500 pM and 1, 2, 5, 10, 20 nM polyamide, respectively. The analyzed 6-base pair binding site locations are designated in brackets along the right side of each autoradiogram with their respective unique base pairs indicated. Schematic binding models of A and B with their putative binding sites are shown on the top side of the autoradiograms. Flanking sequences are designated in lower case, regular type, while the binding site is given in capital bold type. The boxed X•Y base pair indicates the position that was examined in the experiments.

Specific DNA Base-Pair Recognition of Representative Six-Membered Polyamide Pairs A. Imidazo[4,5-b]pyridine/Pyrrole Pair To examine whether an imidazo[4,5-b]pyridine unit Ip can replace a five-membered imidazole ring Im within an eight-ring hairpin polyamide regarding DNA binding affinity and specificity, polyamide oligomer A and its related all five-membered ring hairpin oligomer N were evaluated by DNase I footprint titrations under identical conditions. Quantitative DNase I footprint titration experiments (10 mM Tris-HCl, 10 mM KCl, 10 mM $MgCl_2$, 5 mM $CaCl_2$, pH 7.0, 22° C., equilibration time: 12 h) were performed on a $^{32}$P-3'-labeled EcoRI/PvuII restriction fragment of plasmid pDR1 0 (FIG. 2). This DNA fragment contains four 6-base pair binding sites which differ at one position, 5'-TGTCTA-3',5'-TGTTTA-3', 5'-TGTATA-3', and 5'-TGTGTA-3'. The latter one was regarded as the possible match site having a G•C base pair under the Ip/Py or Im/Py pair, respectively. Indeed, both polyamide oligomers A and N exhibit the same binding site preference (FIG. 3). Oligomer N binds its match site 5'-TGT-GTA-3' with an affinity of $K_a=2.3\times10^9$ $M^{-1}$ and showed a clear preference versus the C•G site by nearly a factor of 10. The affinities to A•T and T•A sites are lower, revealing modest specificity (4-8-fold). The imidazo[4,5-b]pyridine-containing polyamide oligomer A binds the 5'-TGTGTA-3' site with an equilibrium association constant of $K_a=1.2\times10^{10}$ $M^{-1}$, a 5-fold higher affinity than its related oligomer A (FIG. 4). Although the A/T base pair mismatch recognition is similar, the introduction of the Ip/Py pair is accompanied with a slight decrease in binding specificity for the C•G base pair site.

B. Hydroxybenzimidazole/Pyrrole Pair

To examine whether the hydroxybenzimidazole unit Hz can replace a five-membered hydroxypyrrole ring Hp, polyamide oligomer B and its related all five-membered ring hairpin oligomer Q were compared. The all five-membered ring polyamide oligomer Q bounds preferentially to the site 5'-TGTTTA-3' as expected, revealing a preference for the T•A base pair by Hp/Py. The binding affinity determined for the T•A and A•T sites were $K_a=4.1\times10^8$ $M^{-1}$, and $K_a\leq2\times10^7$ $M^{-1}$, respectively, a specificity of at least 20-fold. No binding was detected in the concentration range up to 200 nM for the two G•C and C•G sites. Remarkably, analysis of the hydroxy-ben-zimidazole-containing polyamide oligomer B showed that this hairpin bounds with similar affinity and specificity as oligomer Q. Polyamide oligomer B binds the site 5'-TGTTTA-3' with an affinity of $K_a=5.7\times10^8$ $M^{-1}$, an 18-fold selectivity of T•A over A•T. The sequence 5'-TGT-GTA-3', representing a G•C mismatch site, was bound with at least 80-fold lower affinity. No binding was observed for the C•G mismatch site. Thus, sequence specificity can be retained by replacing an Hp with an Hz unit. It is important to note that the hydroxybenzimidazole-containing polyamide oligomer B is stable at acidic pH.

C. Benzimidazole/Pyrrole Pair

A third polyamide containing the benzimidazole building block was also studied. This allows a comparison of the specificity of Bi/Py pairs with Py/Py pairs and serve as a control as well, confirming that the different specificity of Hz/Py vs Bi/Py is due to the single atomic substitution of CH to COH on the benzene ring (FIG. 5). For the all five-membered ring polyamide oligomer P the DNA binding affinity is highest at match sites 5'-TGTTTA-3' and 5'-TGTATA-3' within a factor of 2. The binding affinity to the G•C and C•G sites is lower by a factor of 23. The same binding site preference was also found for the benzimidazole containing polyamide oligomer C revealing that Bi/Py mimics Py/Py and binds both A•T and T•A.

Construction of plasmid DNA. The plasmid pDR1 was constructed by hybridization of the two oligonucleotides 5'-GATCAGGCTGTC-TATGGACGGCTGCTGTGTATG-GACG-GCTGCTGTTTATGGACG-GCTGCTGTATATG- GACGG-CTGGGCGA-3' (SEQ ID NO:1) and 5'-AGCT-TCGC-CCAGCCGTCCATATACAGCAGCCGTCCAT AAACAGCA-GCCGTCCATACACAGCAGCCGTC-CATAGACAGCCT-3' (SEQ ID NO:2) followed by ligation into the BamHI/HinDIII restriction fragment of pUC19 using T4 DNA ligase. The resultant plasmid was then used to transform E. coli XL-1 Blue Supercompetent cells. Ampicillin-resistant white colonies were selected from 25 mL Luria-Bertani agar plates containing 50 mg/mL ampicillin, treated with XGAL and IPTG solutions and grown overnight at 37° C. Cells were harvested after overnight growth at 37° C. Large-scale plasmid purification was performed with Qiagen, purification kits. The presence of the desired insert was determined by dideoxy sequencing. DNA concentrations were determined at 260 nm using the relationship 1 OD unit) 50 µg/mL duplex DNA.

Preparation of 3'-End-Labeled DNA Restriction Fragments. The plasmid pDR1 was linearized with EcoRI and PVuII and treated with the Klenow fragment of DNA polymerase II, [R-$^{32}$P]-dATP, and [R-$^{32}$P]-TTP for 3'-end labeling. The labeled 3'-fragment was purified on a 7% nondenaturing polyacrylamide gel (5% cross-linkage) and the desired 284 base pair band isolated after visualization by autoradiography. The DNA was precipitated with 2-propanol, the pellet washed, lyophilized, and resuspended in RNase-free H$_2$O. Chemical sequencing reactions were performed according to published protocols. (Troschütz, R.; Lückel, A. *Arch. Pharm.*, 325, 617-619, 1992.)

DNase I Footprinting. All reactions were carried out in a volume of 400 µL according to published procedures. Quantitation by storage phosphor autoradiography and determination of equilibrium association constants were as previously described. (Trauger, J. W.; Dervan, P. B. *Methods Enzymol.*, 340, 450-466, 2001.)

Example 4

DNA Binding Affinity and Sequence Specificity of Representative Oligomers of the Invention When replacing PyPy, PyIm, and PyHp dimers with BiPy (as in oligomer D), BiIm (as in oligomer E), and BiHp constructs (as in oligomer F), respectively, the question arises whether a) the benzimidazole ring is capable of cooperating with the imidazole ring on the opposite strand of the hairpin polyamide to specifically recognize a C•G base pair according to the binding model and the general pairing rules, and b) whether the steric and electronic peculiarities of the benzimidazole ring disturb the binding ability of the adjacent heterocycle. In order to address this question for the given polyamide design, the recognition behavior of the benzimidazole-containing polyamides was probed in two of the six base pair positions R•S and X•Y of the recognition sequence (5'-TGRACA-3' and 5'-TGGXCA-3' for oligomers D and F; 5'-TGRCAA-3' and 5'-TGGXAA-3' for oligomer E; FIG. 6) and compared with the DNA-binding ability of the related all five-membered oligomers R, S, and V at the same recognition sequences.

Figure 7:
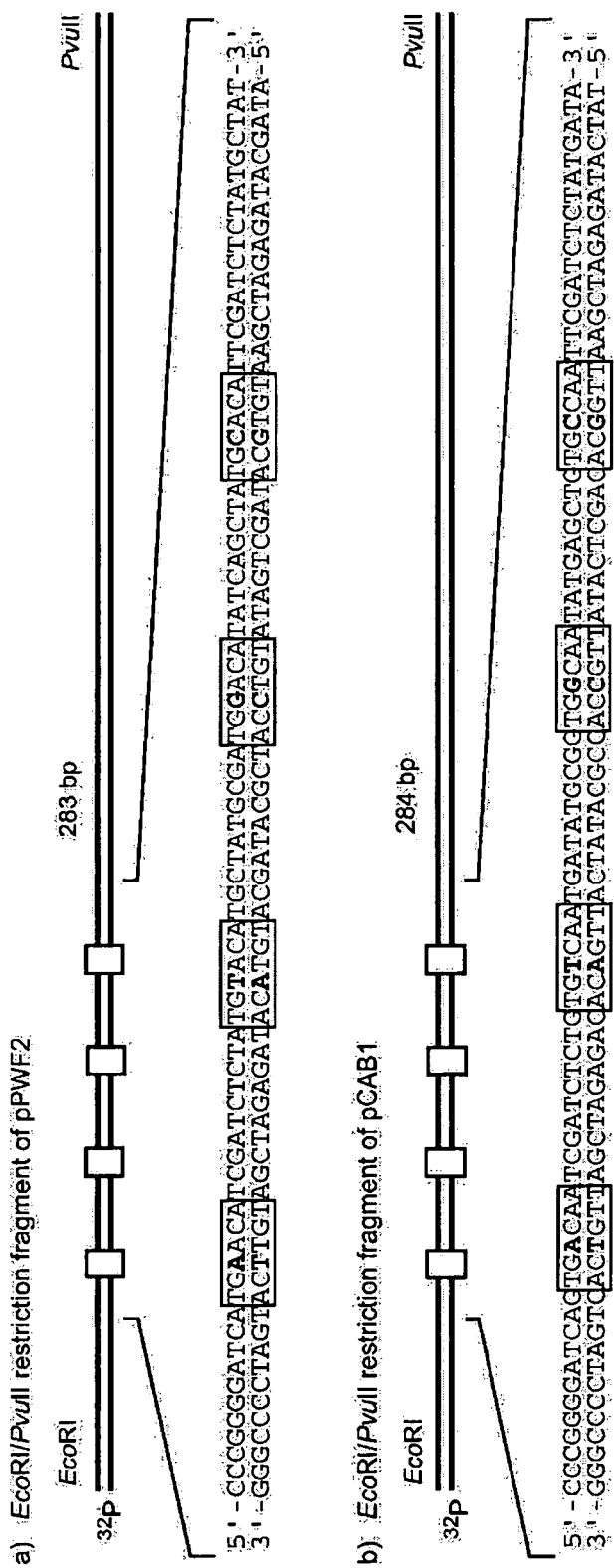
FIG. 7 illustrates the EcoRI/PvuII restriction fragments derived from plasmids pPWF2 (SEQ ID NO: 3) and pCAB1 (SEQ ID NO: 4). The four designed binding sites that were analyzed in quantitative footprint titrations are indicated with a box surrounding each of the six bp sites. The R•S base pair position within the binding sites is shown in bold type.
Figure 8:
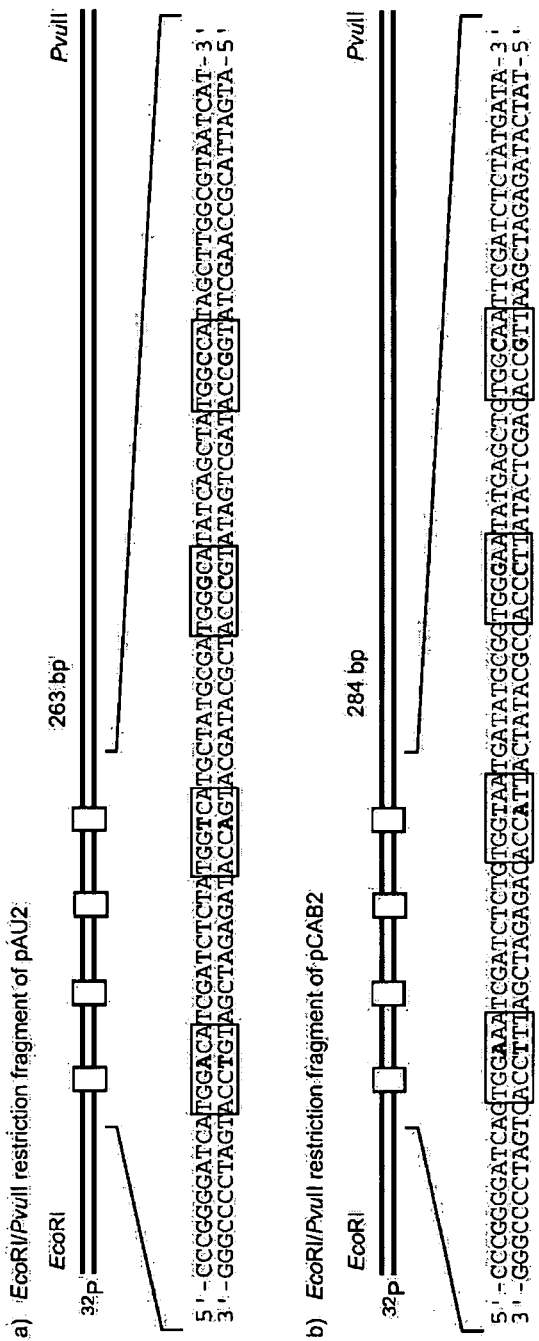
FIG. 8 illustrates the EcoRI/PvuII restriction fragments derived from plasmids a) pAU2 (SEQ ID NO: 5) and b) pCAB2 (SEQ ID NO: 6). The four designed binding sites that were analyzed in quantitative footprint titrations are indicated with a box surrounding each of the six bp sites. The X•Y base pair position within the binding sites is shown in bold type

Evaluation of the DNA recognition properties of the new ligands oligomers D, E, and F at the imidazole/benzimidazole position (referred to as R•S position) should reveal the sequence preference of the benzimidazole ring. The binding properties at the neighboring ring position (referred to as X•Y position) were expected to disclose whether the recognition capabilities of the adjacent internal five-membered ring are disturbed by the benzimidazole moiety. To examine the consequences of the ring replacement for DNA binding in terms of affinity and specificity, the benzimidazole-containing hairpin polyamides oligomers D, E, and F were evaluated by quantitative DNase I footprint titrations and the results compared to those from related oligomers R, S, and V, which were investigated under identical conditions. Quantitative DNase I footprint titration experiments (10 mm Tris-HCl, 10 mm KCl, 10 mm MgCl$_2$, 5 mm CaCl$_2$, pH 7.0, 22° C., equilibration time: 12 h) were performed on $^{32}$P-3'-labeled EcoRI/PvuII restriction fragments of plasmids pPWF2 and pCAB1 (to probe the R•S position, FIG. 7); and pAU2 and pCAB2 (to probe the X•Y position, FIG. 8). Equilibrium association constants (K$_a$) for the polyamide oligomers at the binding sites of interest were determined as described above in Example 3.

Figure 11:
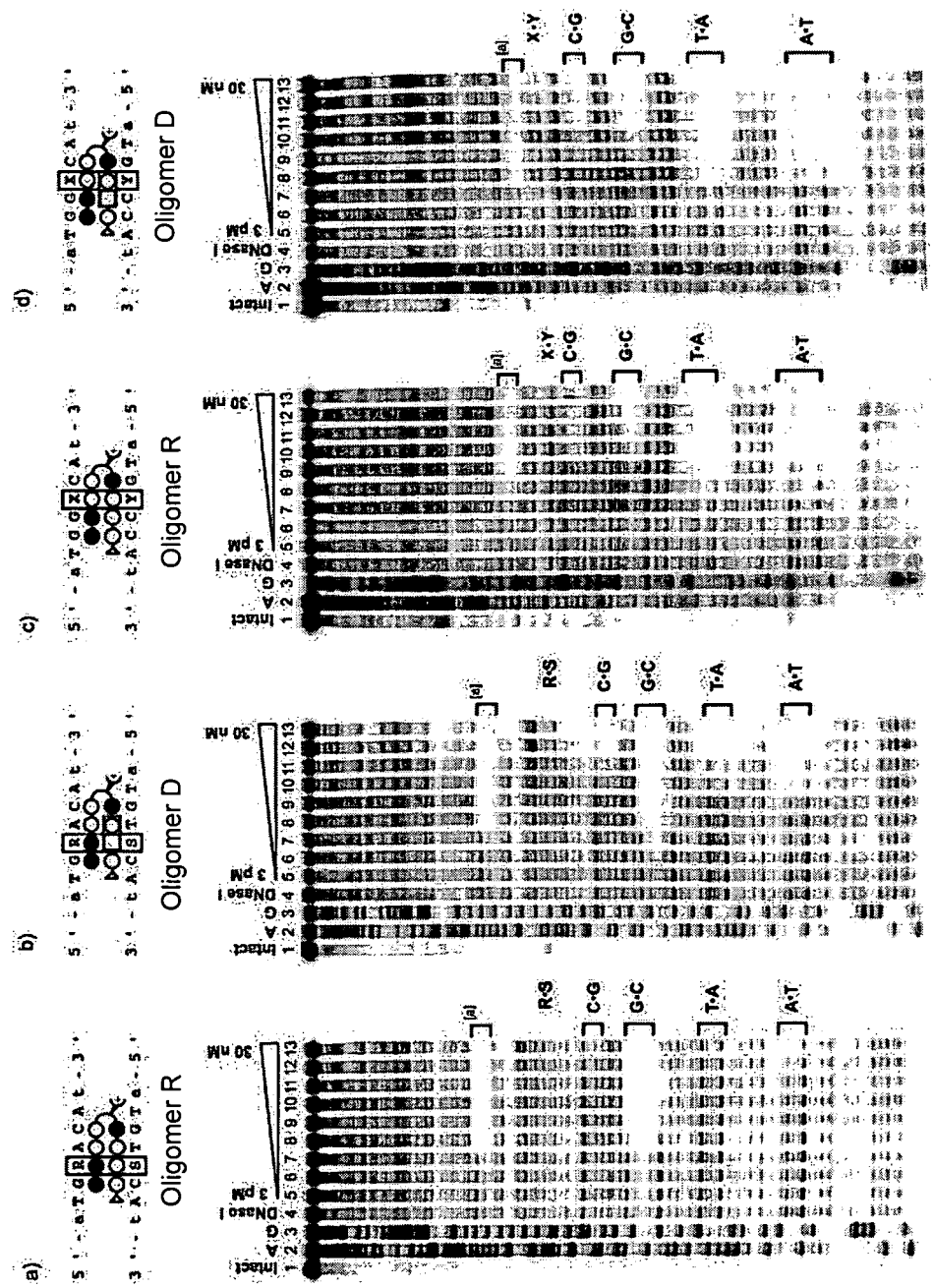
FIG. 11 illustrates the quantitative DNase I footprint titration experiments on the 3'-$^{32}$P-labeled 283-bp and 263-bp EcoRI/PvuII restriction fragments derived from plasmids pPWF2 (a and b) and pAU2 (c and d), respectively. a) and c) polyamide oligomer R: lane 1, intact DNA; lane 2, A-specific reaction; lane 3, G-specific reaction; lane 4, DNase I standard; lanes 5±13: 3, 10, 30, 100, 300 pm and 1, 3, 10, 30 nm polyamide, respectively. b) and d) polyamide oligomer D: lane 1, intact DNA; lane 2, A-specific reaction; lane 3, G-specific reaction; lane 4, DNase I standard; lanes 5±13: 3, 10, 30, 100, 300 pm and 1, 3, 10, 30 nm polyamide, respectively. The analyzed 6-bp binding site locations are designated in brackets along the right side of each autoradiogram with their respective unique base pairs indicated. Schematic binding models of R and D with their putative binding sites are shown on the top side of the autoradiograms. Flanking sequences are designated in lower case while the binding site is given in capitals. The boxed R•S and X•Y base pairs indicate the positions that were examined in the experiments. [a] Additional match site for R and D; sequence 5'-aTGGTCAt-3'.
Figure 12:
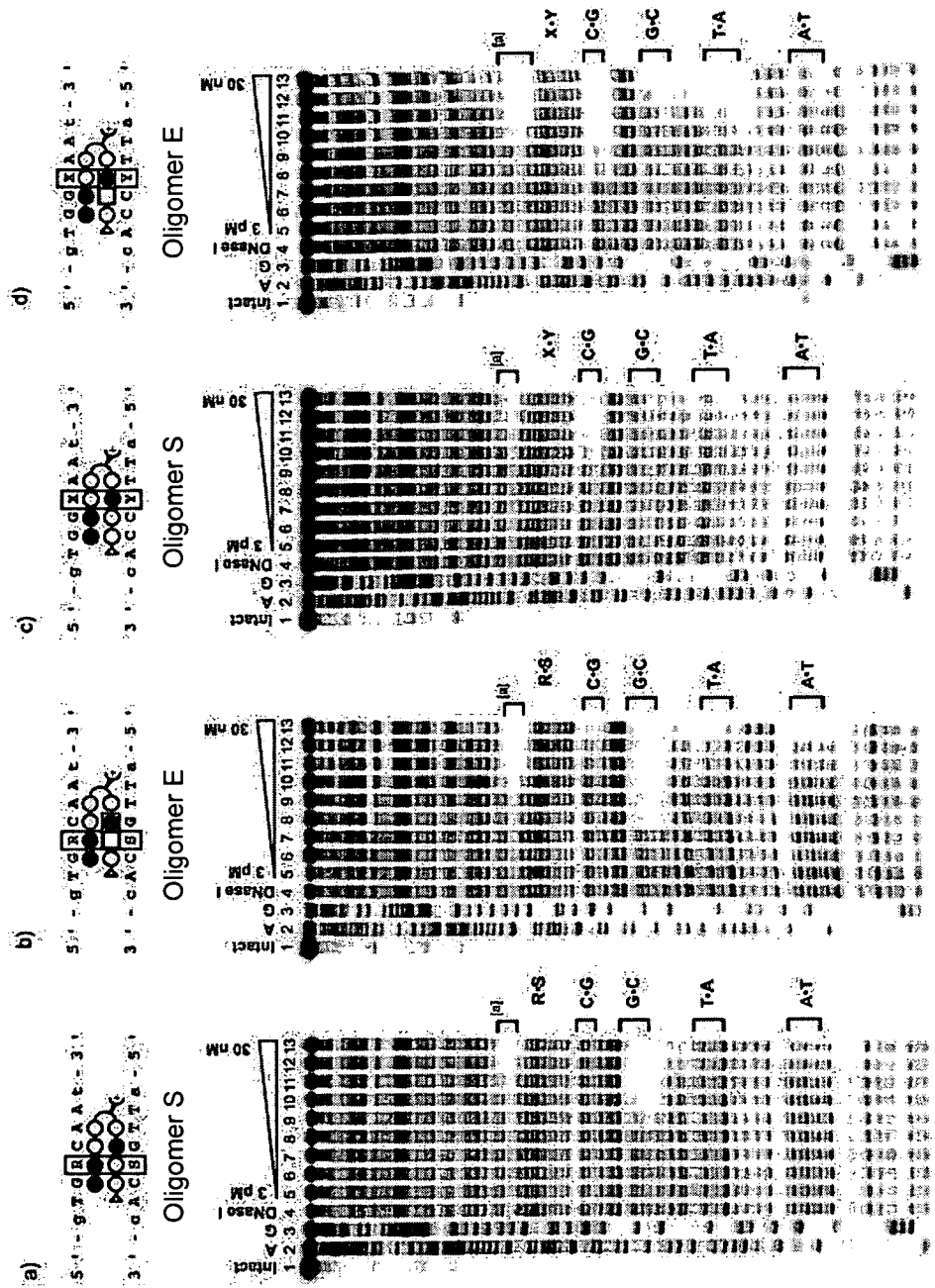
FIG. 12 illustrates the quantitative DNase I footprint titration experiments on the 3'-$^{32}$P-labeled 284-bp EcoRI/PvuII restriction fragments derived from plasmid pCAB1 (a and b) and pCAB2 (c and d). a) and c) polyamide oligomer S: lane 1, intact DNA; lane 2, A-specific reaction; lane 3, G-specific reaction; lane 4, DNase I standard; lanes 5±13: 3, 10, 30, 100, 300 pm and 1, 3, 10, 30 nm polyamide, respectively. b) and d) polyamide oligomer E: lane 1, intact DNA; lane 2, A-specific reaction; lane 3, G-specific reaction; lane 4, DNase I standard; lanes 5±13: 3, 10, 30, 100, 300 pm and 1, 3, 10, 30 nm polyamide, respectively. The analyzed 6-bp binding site locations are designated in brackets along the right side of each autoradiogram with their respective unique base pairs indicated. Schematic binding models of S and E with their putative binding sites are shown on the top side of the autoradiograms. Flanking sequences are designated in lower case while the binding site is given in capitals. The boxed R•S and X•Y base pairs indicate the positions that were examined in the experiments. [a] Three overlapping 1-bp mismatch sites for S and E; sequence

On first inspection, analysis of the footprint data at position R•S (FIG. 9) and at position X•Y (FIG. 10) extracted from the autoradiograms shown in FIGS. 11-13 reveals that the benzimidazole-containing polyamide oligomers D, E, and F and the related oligomers R, S, and V exhibit the same binding site preferences for matched and mismatched sites on the 3'-labeled restriction fragments derived from pPWF2, pCAB1, pAU2, and pCAB2. The expected match sites out of the sequence families 5'-TGRACA-3' or 5'-TGRCAA-3' (R•S position) and 5'-TGGXCA-3' or 5'-TGGXAA-3' (X•Y position) are bound with comparable equilibrium association constants by the benzimidazole-containing oligomers D, E, and F and the related hairpin polyamide oligomers D, E, and F and related hairpin polyamide oligomers R, S, and V. All compounds bind their match sites with high affinities in the sub-nanomolar range (K$_a$ values range from $4.9 \times 10^{10}$ M$^{-1}$ for R•S position of oligomer D and X•Y position of oligomer R down to $3.5 \times 10^9$ M$^{-1}$ for X•Y position of oligomer S).

Molecular recognition at the R•S position: While both benzimidazole-containing polyamide oligomer D and related oligomer R display comparable match-site affinities (K$_a$=4.9×10$^{10}$ M$^{-1}$ and K$_a$=2.7×10$^{10}$ M$^{-1}$, respectively), benzimidazole-containing polyamide oligomers E and F exhibit a six to seven-fold higher match site affinity (K$_a$=3.1×10$^{10}$ M$^{-1}$ and K$_a$=2.5×10$^{10}$ M$^{-1}$, respectively) than the related oligomers oligomers D, E, and F and related oligomers R, S, and V (K$_a$=5.2×10$^9$ M$^{-11}$ and K$_a$=3.8×10$^9$ M$^{-1}$, respectively). A significant difference can be seen for the two sets of compounds when their mismatch-site affinities and the associated single site specificities are compared. The replacement of the PyPy, PyIm, and PyHp constructs by the benzimidazole-Py, -Im, and -Hp analogues is generally accompanied by an increase in the binding affinities for the single base pair mismatch sites of benzimidazole-containing polyamide oligomers D, E, and F resulting in overall mildly diminished binding specificities. More precisely, for polyamide oligomer D single base pair mismatch specificities are lower by roughly one order of magnitude when compared with the related oligomer R. By contrast, oligomer F displays a specificity profile that is comparable to that of the related oligomer V. For benzimidazole-containing oligomer E the match site/mismatch site discrimination is comparable for R=A but reveals at least ten-fold lower specificities for R=T or C.

Molecular recognition at the X•Y position: As expected, for the X•Y position of the sequence family 5'-TGGXCA-3' (oligomers R & D and V & F) and 5'-TGGXAA-3' (oligomers S and E) the response to the heterocycle replacement in terms of match site/single base pair mismatch site discrimination is less pronounced. Binding affinities for match and mismatch sites and the associated binding specificities reveal the same overall trend and range in the same order of magnitude for both the benzimidazole-containing polyamide oligomers D, F and the related oligomers R, V. By contrast, benzimidazole-containing polyamide oligomer E exhibits a six-fold higher match site affinity than its related oligomer S ($K_a=1.9\times10^{10}$ $M^{-11}$ vs $K_a=3.5\times10^9$ $M^{-1}$, respectively). Along with the significantly higher match site affinity of oligomer E slightly increased binding affinities for single base pair mismatch sites are displayed, which result in mildly diminished specificities when compared with the values of the related oligomer S. The introduction of the benzimidazole moiety has only a marginal influence on the binding properties of the adjacent five-membered internal ring.

The results from the discussed quantitative DNase I footprint titrations demonstrate that the benzene ring of the benzimidazole moiety is able to pair with an Im residue within the context of a hairpin polyamide and that, as a consequence, this pairing is able to distinguish G•C from C•G, A•T, and T•A. The benzimidazole moiety minimally disturbs the recognition properties of the adjacent internal five-membered heterocycle resulting in single base pair mismatch specificities at the X•Y position that are similar to those of the corresponding all five-membered heterocyclic polyamide oligomers. In addition, all benzimidazole-polyamides retain or even exceed the subnanomolar association constants of their corresponding all five-membered heterocycle oligomers at their match sites.

Example 5

DNA Binding for Exemplary Polyamides

For polyamides Im-Im-Hz-Py-γ-Im-Py-Py-Py-β-Dp (oligomer G) and Im-Im-Py-Py-γ-Im-Hz-Py-Py-β-Dp (oligomer J), the DNA-sequence specificity at a single ring-pairing position (bolded in the sequences listed above) was determined by varying a single DNA base pair within the parent-sequence context, 5'-TGGXCA-3', to all four Watson-Crick base pairs (X=A, T, G, C) and comparing the relative affinities of the resulting complexes (FIG. 14). The variable base-pair position was installed opposite the novel Hz/Py and Py/Hz pairs, designed to target T•A and A•T respectively. Equilibrium association constants ($K_a$) for polyamide oligomers containing Py/Py, Hp/Py and Py/Hp pairs have been reported and are included for comparison with values presented here (FIG. 15). Polyamide oligomer G (Hz/Py pair) bound at high affinity ($K_a$=mid $10^9$) and demonstrated a strong single site specificity, preferring T•A over A•T by 10-fold, and A,T over G,C by more than 50-fold. In comparison to the Hp/Py pair, the Hz/Py exhibited a higher affinity, similar T vs. A specificity, and much greater A,T over G,C specificity. Polyamide oligomer J (Py/Hz pair) bound at high affinity ($K_a$=low $10^9$) and demonstrated a moderate single site specificity, preferring A•T over T•A by more than 4-fold, and A,T over G,C by more than 30-fold. In comparison to the Py/Hp pair, the Py/Hz pair within this sequence context shows slightly lower T vs. A specificity, but improved A,T over G,C specificity. Both polyamide oligomers G and J, containing the Hz/Py and Py/Hz pairs respectively, bound with comparable affinity and superior single site specificity in comparison to the degenerate Py/Py pair.

For polyamides Im-Hz-Py-Py-γ-Im-Hz-Py-Py-β-Dp (oligomer H) and Im-Py-Hz-Py-γ-Im-Py-Hz-Py-β-Dp (oligomer K) the ability of multiple Hz/Py pairs to distinguish poly A,T sequences was tested by varying two DNA base pairs across from the Hz/Py and Py/Hz pairs (bolded in the sequences listed above) within the parent-sequence context, 5'-AGW-WCT-3', (W=A, T) and comparing the relative affinities of the resulting complexes (FIG. 16). Equilibrium association constants ($K_a$) for polyamide oligomers containing multiple Hp/Py pairs have been reported and are included for comparison with values presented here (FIG. 17). Polyamide oligomer H bound at moderate affinity ($K_a$=mid $10^8$) and showed good specificity (greater than 14-fold) for its match sequence 5'-AGTACT-3' over 5'-AGAACT-3' and 5'-AGATCT-3'. Polyamide oligomer K bound all three sites at moderate affinity ($K_a$=low $10^8$), demonstrating poor site selectivity. The recognition profiles of polyamide oligomers containing multiple Hz/Py pairs (oligomers H and K) are similar to those reported for multiple Hp/Py pairs. Polyamide oligomers H and K also demonstrated lowered affinities but superior specificity in comparison to the polyamide oligomers containing multiple symmetrical Py/Py pairs.

For polyamides Im-Im-Hz-Py-γ-Im-Bi-Py-Py-β-Dp (oligomer I) and Im-Im-Bi-Py-γ-Im-Hz-Py-Py-β-Dp (oligomer L) the DNA-sequence specificity at a single ring-pairing position (bolded in the sequences listed above) was determined by varying a single DNA base pair within the parent-sequence context, 5'-TGGXCA-3', to all four Watson-Crick base pairs (X=A, T, G, C) and comparing the relative affinities of the resulting complexes (FIGS. 18 and 19). The variable base-pair position was installed opposite the novel Hz/Bi and Bi/Hz pairs, designed to target T•A and A•T respectively. Polyamide oligomer I (Hz/Bi pair) bound with a markedly high affinity ($K_a$=low $10^{10}$), demonstrating a 13-fold selectivity for A,T over G,C and 2.5-fold preference for T•A over A•T. Polyamide oligomer L (Bi/Hz pair) also bound with high affinity, lowered A,T over G,C selectivity (4.5-fold), and a 2.5-fold preference for A•T over T•A. Polyamide oligomers containing Hz/Bi pairs bind with significantly higher affinity than those containing the Hz/Py pairings, but with a mild loss in A,T selectivity.

Footprinting Experiments.—Plasmids pDHN1 and pDEH10 were constructed and 5'-radiolabeled as previously described. (Nguyen, D. H. et al., *Bioorg. Med. Chem.*, 9: 7-17, 2001; Melander, C. et al., *Chem. Eur. J.*, 24: 4487-4497, 2000.) DNase I footprint titrations were performed according to standard protocols. (Trauger, J. W. et al., *Methods Enzymol.*, 340: 450-466, 2001.)

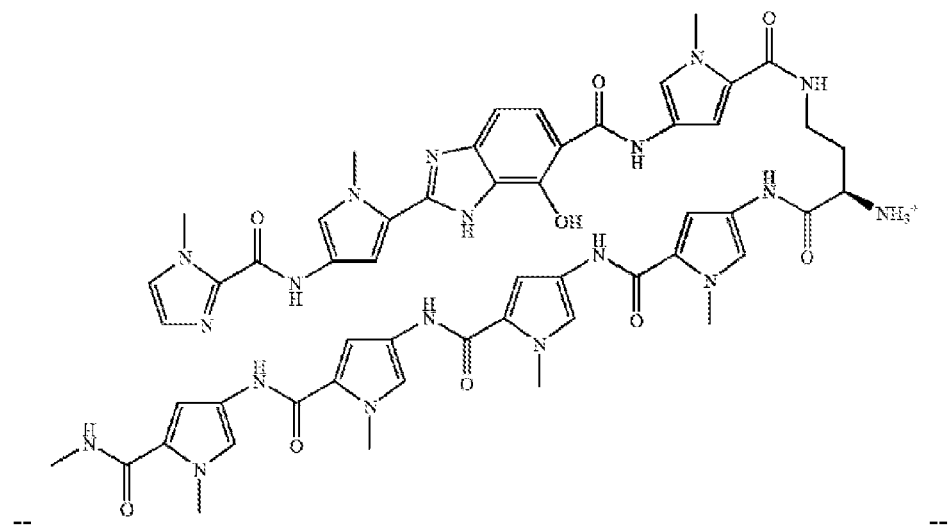

What is claimed is:

1. An oligomer or a pharmaceutically acceptable salt thereof, wherein said oligomer is selected from the group consisting of:

| Oligomer Name | Oligomer Structure |
|---|---|
| A | |
| B | |
| C | |

-continued
| Oligomer Name | Oligomer Structure |
|---|---|
| D | 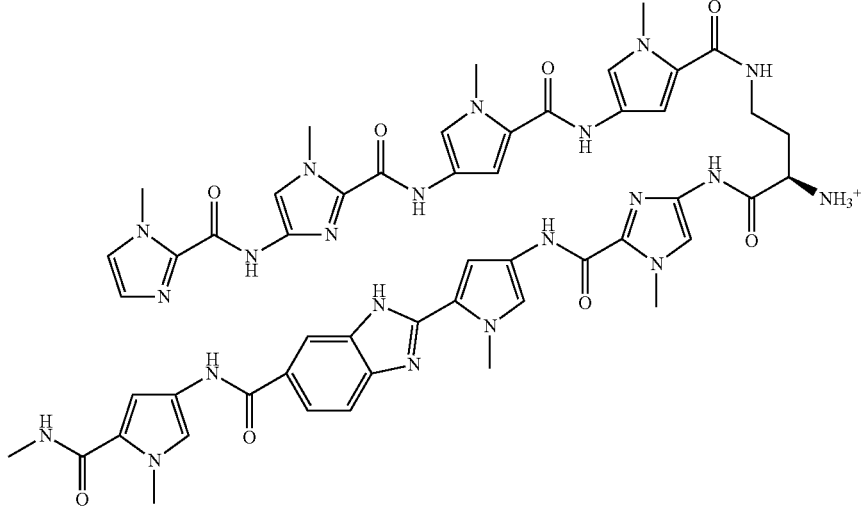 [SMILES: CNC(=O)c1cc(NC(=O)c2ccc3nc(-c4cc(NC(=O)c5nc(NC(=O)[C@H]([NH3+])CCNC(=O)c6cc(NC(=O)c7cc(NC(=O)c8nc(NC(=O)c9nccn9C)cn8C)cn7C)cn6C)cn5C)cn4C)[nH]c3c2)cn1C] |
| E | 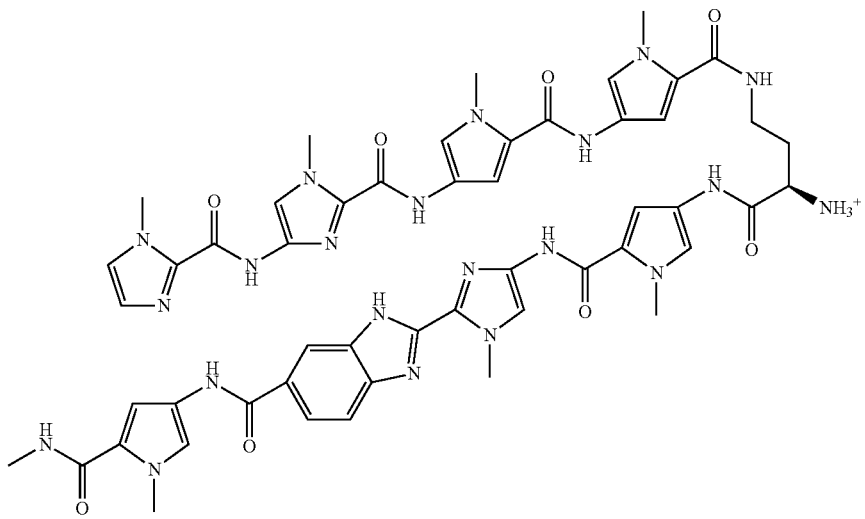 |
| F | 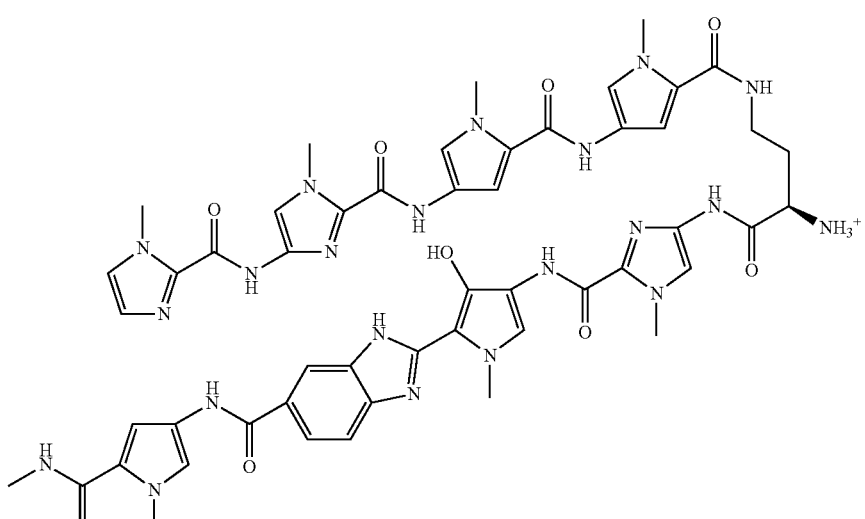 |

| Oligomer Name | Oligomer Structure |
|---|---|
| G | 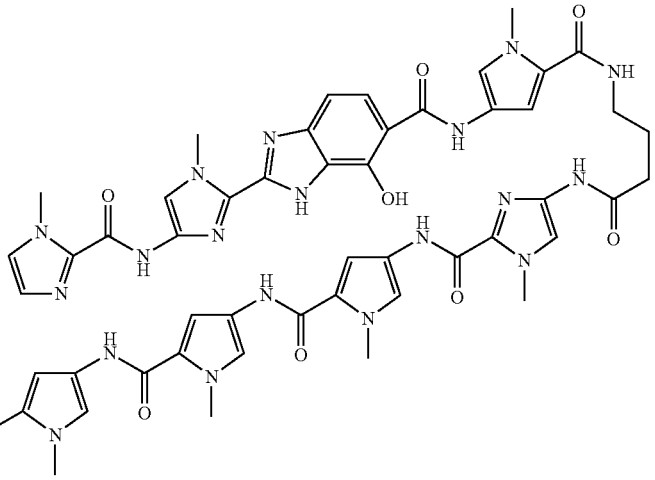 |
| I | 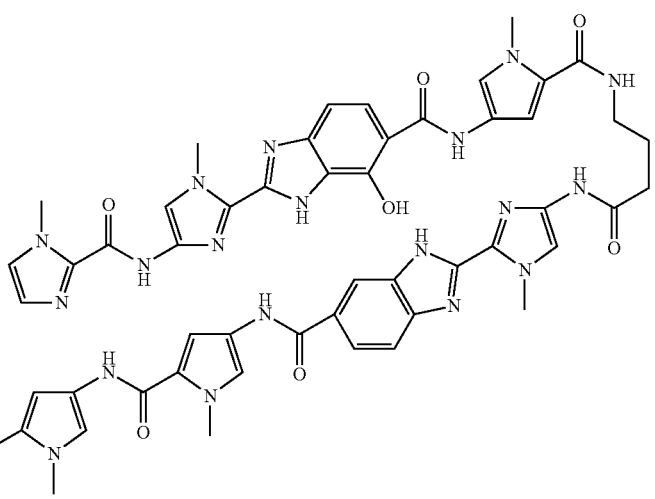 |
| J | 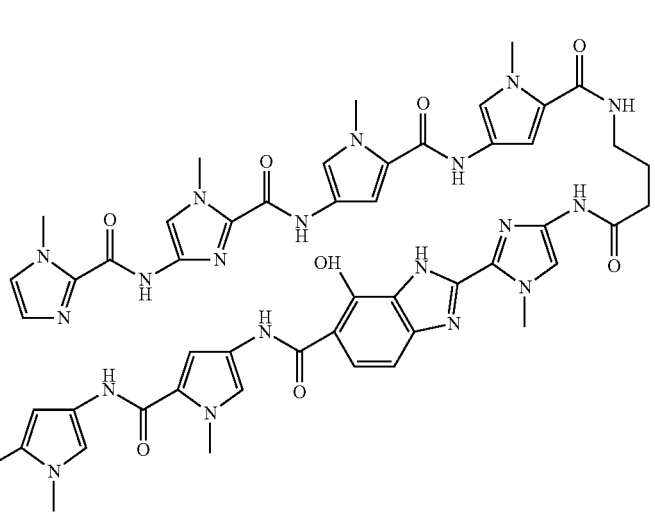 |

| Oligomer Name | Oligomer Structure |
|---|---|
| K | 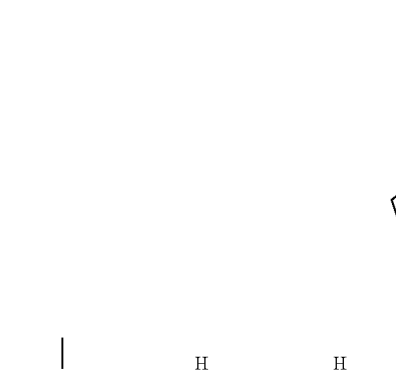 |
| L | 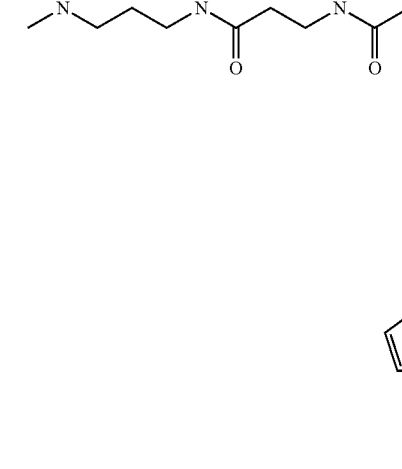 |
2. The oligomer of claim 1, wherein said oligomer is
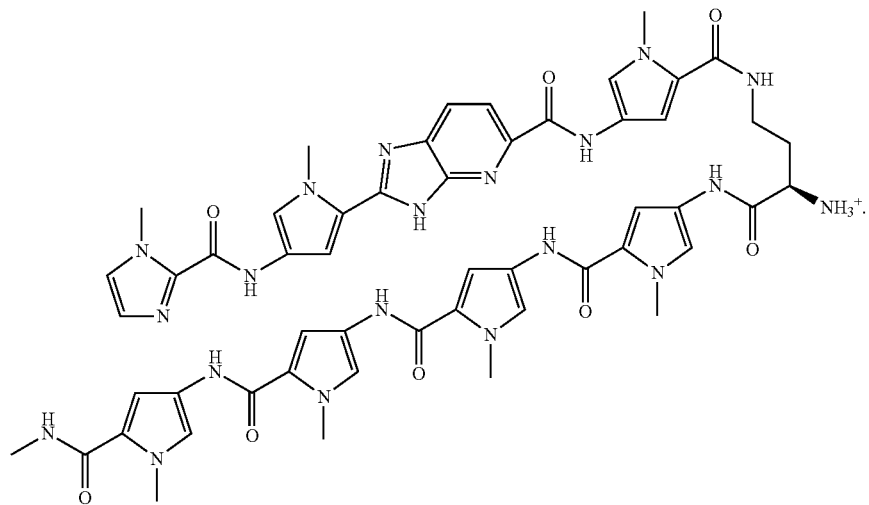

3. The oligomer of claim 1, wherein said oligomer is
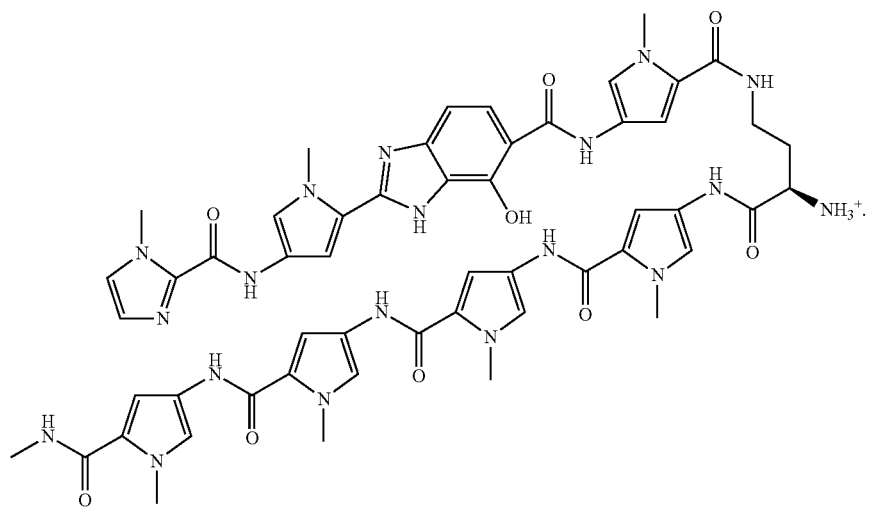
4. The oligomer of claim 1, wherein said oligomer is
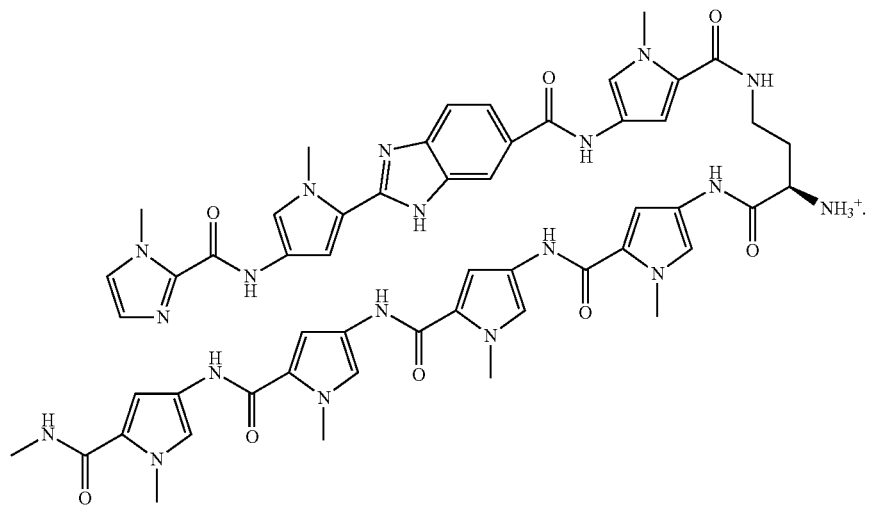
5. The oligomer of claim 1, wherein said oligomer is
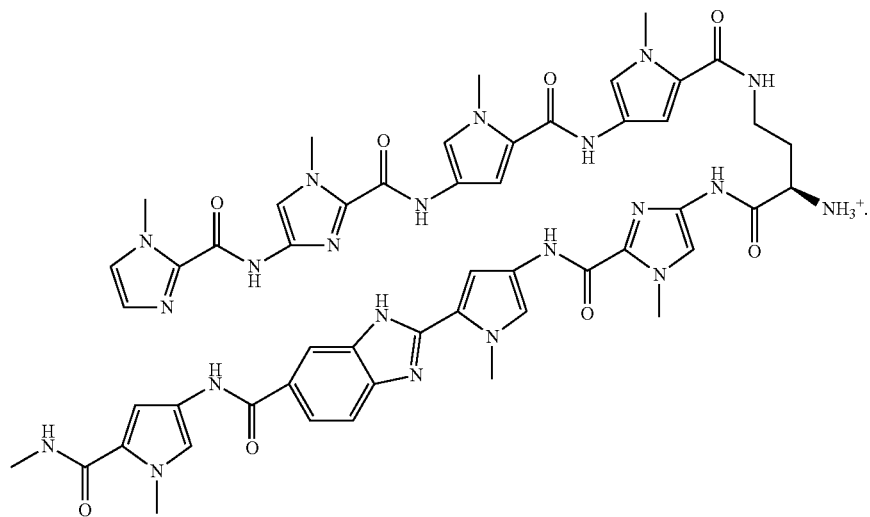

6. The oligomer of claim 1, wherein said oligomer is
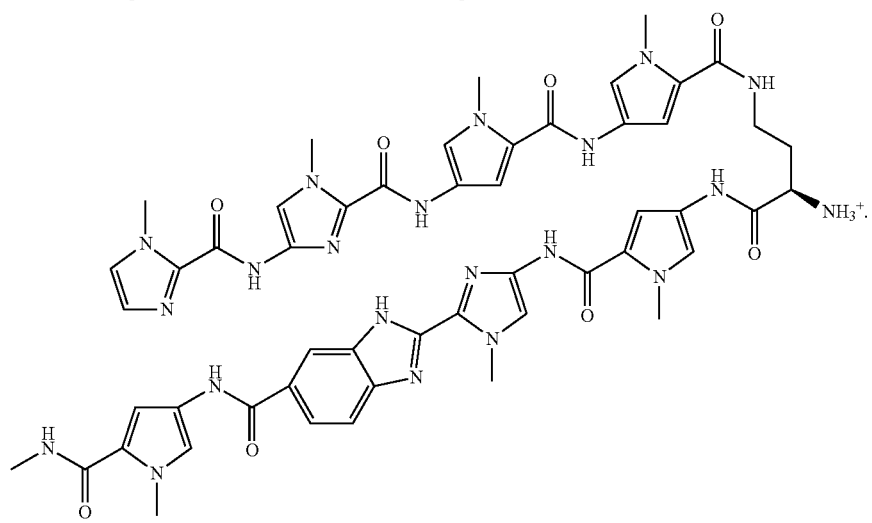
7. The oligomer of claim 1, wherein said oligomer is
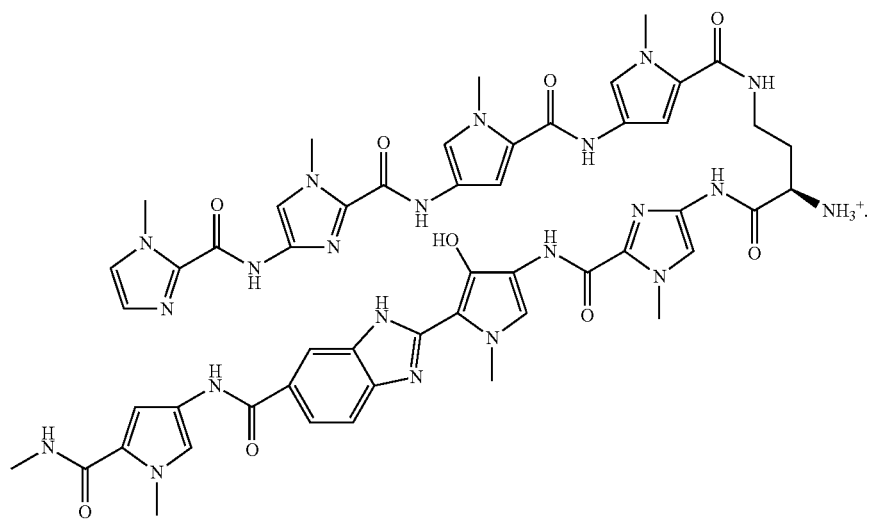
8. The oligomer of claim 1, wherein said oligomer is
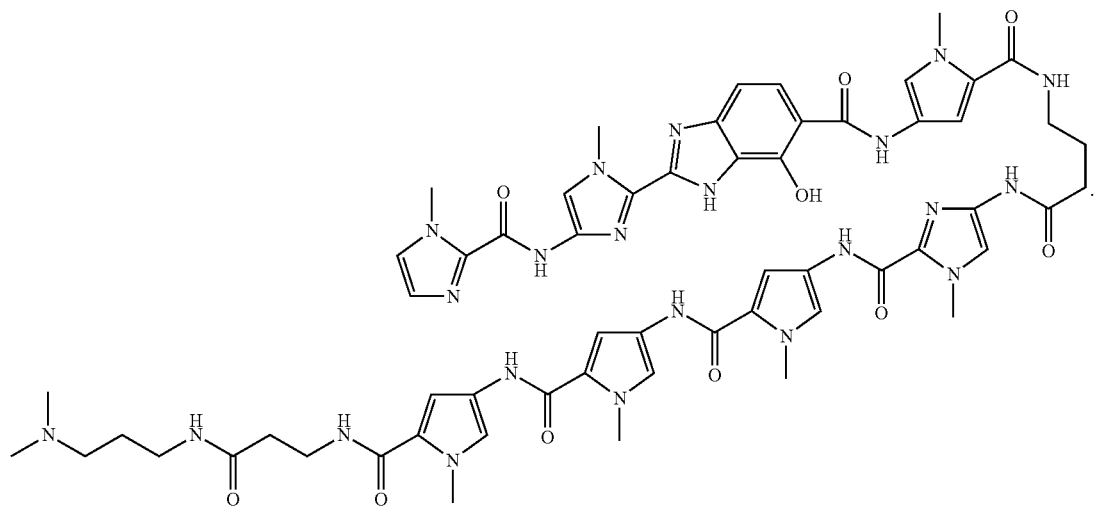 [SMILES: CN(C)CCCNC(=O)CCNC(=O)c1cc(NC(=O)c2cc(NC(=O)c3cc(NC(=O)c4nc(NC(=O)CCCNC(=O)c5cc(NC(=O)c6ccc7nc(-c8nc(NC(=O)c9nccn9C)cn8C)[nH]c7c6O)cn5C)cn4C)cn3C)cn2C)cn1C]

9. An oligomer or a pharmaceutically acceptable salt thereof, wherein said oligomer is
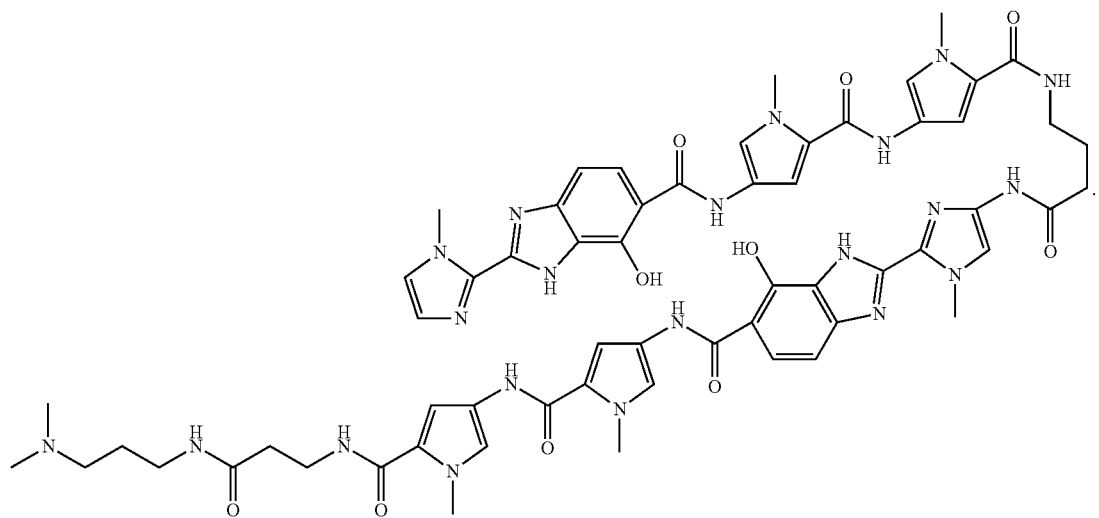 [SMILES: CN(C)CCCNC(=O)CCNC(=O)c1cc(NC(=O)c2cc(NC(=O)c3ccc4nc(-c5nc(NC(=O)CCCNC(=O)c6cc(NC(=O)c7cc(NC(=O)c8ccc9nc(-c%10nccn%10C)[nH]c9c8O)cn7C)cn6C)cn5C)[nH]c4c3O)cn2C)cn1C]
10. The oligomer of claim 1, wherein said oligomer is
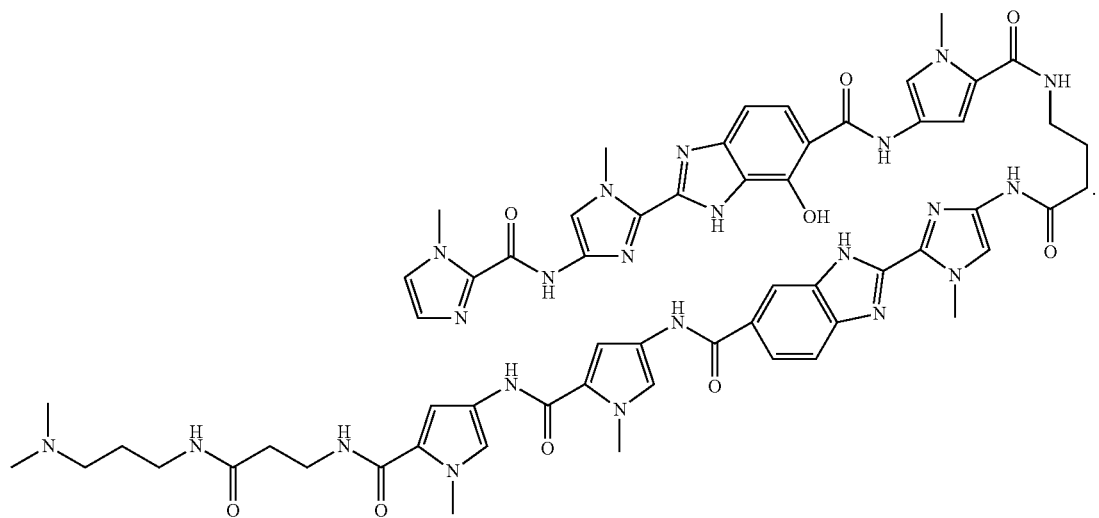 [SMILES: CN(C)CCCNC(=O)CCNC(=O)c1cc(NC(=O)c2cc(NC(=O)c3ccc4nc(-c5nc(NC(=O)CCCNC(=O)c6cc(NC(=O)c7ccc8nc(-c9nc(NC(=O)c%10nccn%10C)cn9C)[nH]c8c7O)cn6C)cn5C)[nH]c4c3)cn2C)cn1C]
11. The oligomer of claim 1, wherein said oligomer is
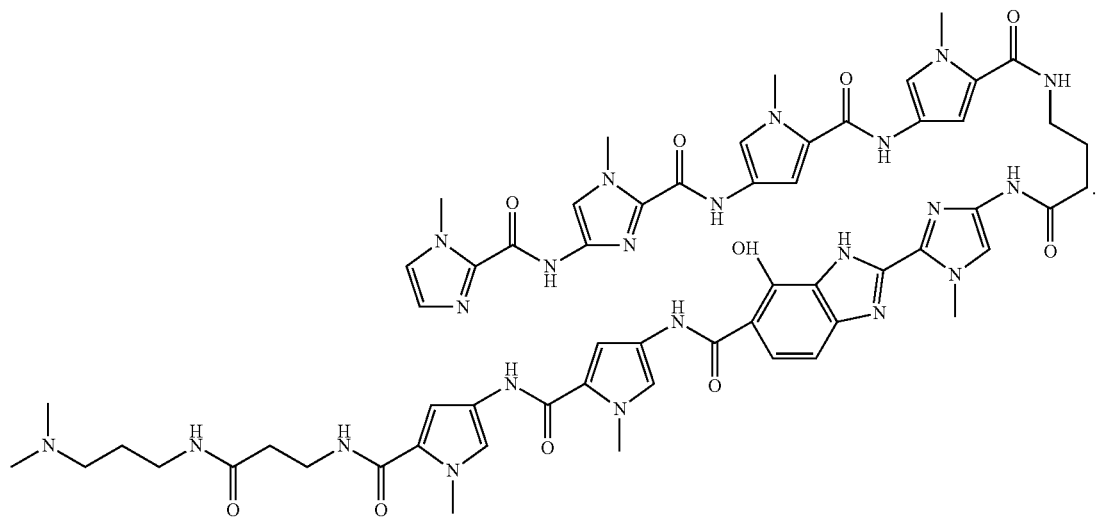 [SMILES: CN(C)CCCNC(=O)CCNC(=O)c1cc(NC(=O)c2cc(NC(=O)c3ccc4nc(-c5nc(NC(=O)CCCNC(=O)c6cc(NC(=O)c7cc(NC(=O)c8nc(NC(=O)c9nccn9C)cn8C)cn7C)cn6C)cn5C)[nH]c4c3O)cn2C)cn1C]

12. The oligomer of claim 1, wherein said oligomer is
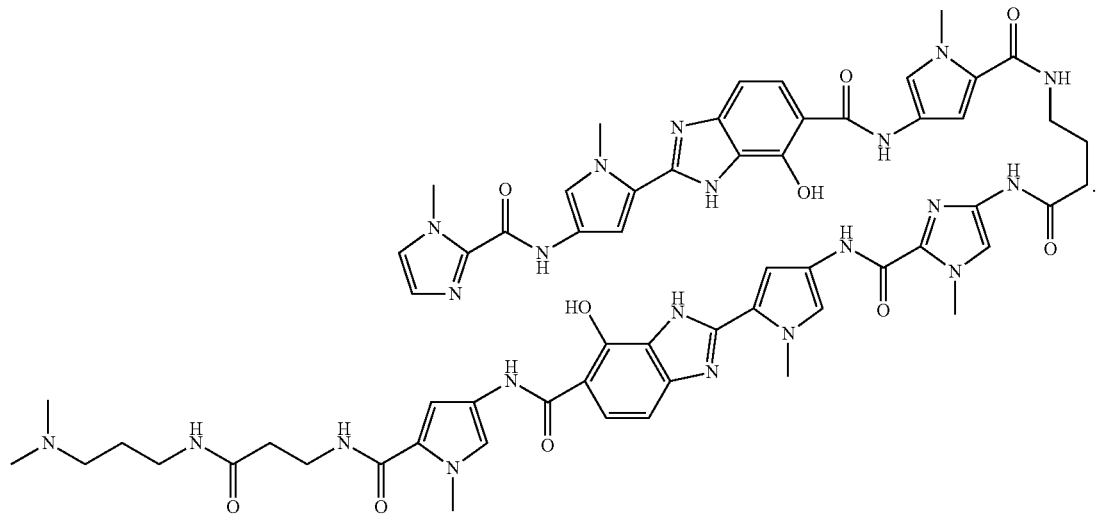 [SMILES: CN(C)CCCNC(=O)CCNC(=O)c1cc(NC(=O)c2ccc3nc(-c4cc(NC(=O)c5nc(NC(=O)CCCNC(=O)c6cc(NC(=O)c7ccc8nc(-c9cc(NC(=O)c%10nccn%10C)cn9C)[nH]c8c7O)cn6C)cn5C)cn4C)[nH]c3c2O)cn1C]
13. The oligomer of claim 1, wherein said oligomer is
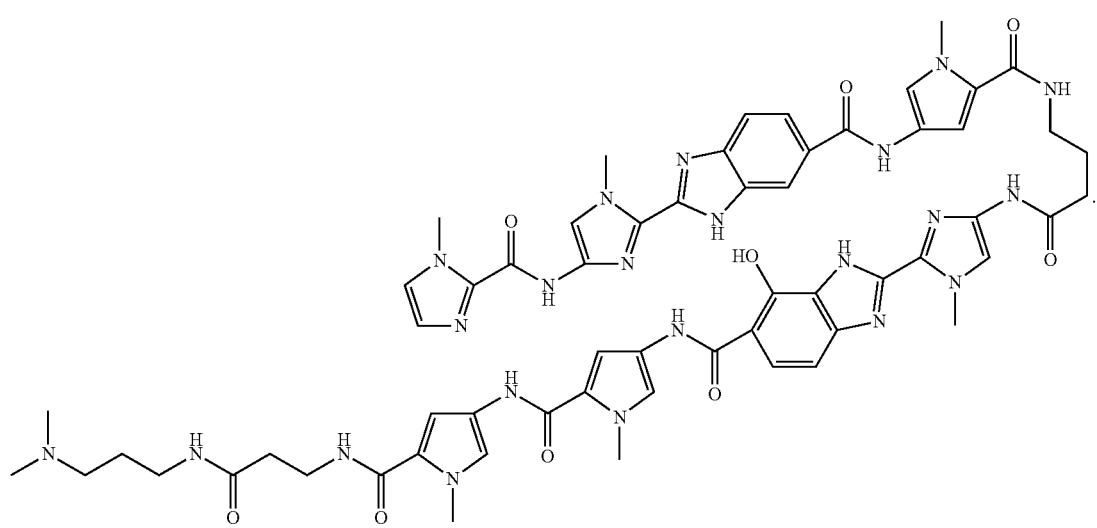 [SMILES: CN(C)CCCNC(=O)CCNC(=O)c1cc(NC(=O)c2cc(NC(=O)c3ccc4nc(-c5nc(NC(=O)CCCNC(=O)c6cc(NC(=O)c7ccc8nc(-c9nc(NC(=O)c%10nccn%10C)cn9C)[nH]c8c7)cn6C)cn5C)[nH]c4c3O)cn2C)cn1C]
* * * * *

UNITED STATES PATENT AND TRADEMARK OFFICE
CERTIFICATE OF CORRECTION

| | | Page 1 of 1 |
|---|---|---|
| PATENT NO. | : 8,524,899 B2 | |
| APPLICATION NO. | : 10/794584 | |
| DATED | : September 3, 2013 | |
| INVENTOR(S) | : Dervan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1039 days.

Signed and Sealed this
Tenth Day of February, 2015

Michelle K. Lee
*Deputy Director of the United States Patent and Trademark Office*

UNITED STATES PATENT AND TRADEMARK OFFICE
CERTIFICATE OF CORRECTION

Page 1 of 2

PATENT NO. : 8,524,899 B2
APPLICATION NO. : 10/794584
DATED : September 3, 2013
INVENTOR(S) : Peter B. Dervan et al.

It is certified that error appears in the above-identified patent and that said Letters Patent is hereby corrected as shown below:

In the Drawings

Figure 1B:
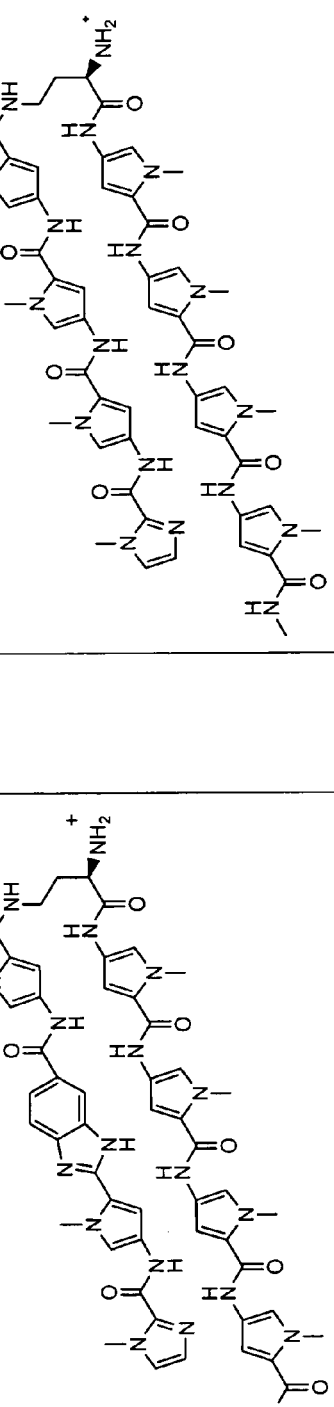

In Fig. 1a-1c, "$NH_2^+$" in the structures of Oligomers A, B, C, D, E, F, N, Q, P, R, S and V should read: -- $NH_3^+$ --

In Fig. 1a, the structure of Oligomer B:

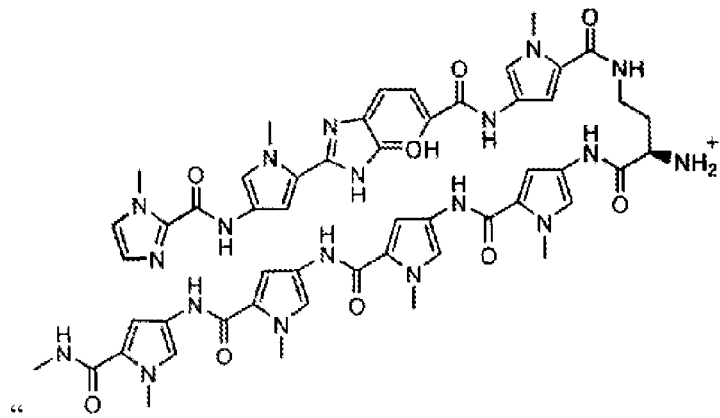

" should read:

Signed and Sealed this
Eighth Day of May, 2018

Andrei Iancu
*Director of the United States Patent and Trademark Office*